US006830893B2

(12) United States Patent
Wang et al.

(10) Patent No.: US 6,830,893 B2
(45) Date of Patent: Dec. 14, 2004

(54) T20/DP178 IS AN ACTIVATOR OF HUMAN PHAGOCYTE FORMYL PEPTIDE RECEPTORS

(75) Inventors: Ji Ming Wang, Frederick, MD (US); Joost J. Oppenheim, Bethesda, MD (US); Shao-Bo Su, Rockville, MD (US); Wang Hua Gong, Frederick, MD (US); Ji-Liang Gao, Frederick, MD (US); Philip M. Murphy, Rockville, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 36 days.

(21) Appl. No.: 10/005,305

(22) Filed: Nov. 2, 2001

(65) Prior Publication Data

US 2003/0203841 A1 Oct. 30, 2003

Related U.S. Application Data

(63) Continuation of application No. PCT/US00/12371, filed on May 5, 2000.
(60) Provisional application No. 60/132,686, filed on May 5, 1999.

(51) Int. Cl.[7] ............................................. G01N 33/50
(52) U.S. Cl. ....................................... 435/7.1; 436/501
(58) Field of Search .............................. 514/2; 435/7.1; 436/501

(56) References Cited

FOREIGN PATENT DOCUMENTS

| WO | WO 96/40191 | 12/1996 |
|---|---|---|
| WO | WO/00/66622 | 11/2000 |
| WO | WO 01/21188 | 3/2001 |
| WO | WO 01/57074 | 8/2001 |

OTHER PUBLICATIONS

Wells, 1990, Biochemistry 29:8509–8517.*
Ngo et al., 1994, The Protein Folding Problem and Tertiary Strauctrure Prediction, Merz et al., eds., Birkhauser, Boston, pp. 492–495.*
Bork, 2000, Genome Research 10:398–400.*
Skolnick et al., 2000, Trends in Biotech 18:34–39.*
Doerks et al., 1998, Trends in genetics 14:248–250.*
Smith et al., 1997, Nature Biotechnology 15:1222–1223.*
Brenner, 1999, Trends in Genetics 15:132–133.*
Bork et al., 1996, Trends in Genetics 12:425–427.*
Brown, L. E., et al. (1995) Synthetic Peptides Representing Sequences Within gp41 of HIV as immunogens for murine T– and B–cell responses. Arch. Virol. 140(4):635–654.
Kilby, J. M., et al. (1998) Potent Suppression of HIV–1 Reptication in Humans by T–20, a Peptide Inhibitor of gp41–mediated Virus Entry. Nature Medicine 4:1302–1307.
Lawless, M. K., et al. (1996) HIV–1 Membrane Fusion Mechanism: Structural Studies of the Interactions between Biologically–Active Peptides from gp41. Biochemistry 35(42):13697–13708.
Su, S. B., et al. (1999) T20/DP178, an Ectodomain Peptide of Human Immunodeficiency Virus Type 1 gp41, Is an Activator of Human Phagocyte N–Formyl Peptide Receptor. Blood 93(11):3885–3892.
Su, S. B., et al. (1999) T20/DP178, an Ectodomain Peptide of Human Immunodeficiency Virus Type 1 gp41, Is a Potent Activator of Human Phagocyte N–Formyl Peptide Receptor. FASEB Journal 13(4):pA293 (Annual Meeting of the Professional Research Scientists for Experimental Biology—Apr. 17–21, 1999).
Su. S. B., et al. (1999) T21/DP107, A Synthetic Zipper–Like Domain of the HIV–1 Envelope gp41, Attracts and Activates Human Phagocytes by Using G–Protein–Coupled Formyl Peptide Receptors. J. Immunology 162(10):5924–30.
Tas, M., et al. (1988) A Monocyle Chemotaxis Inhibiting Factor in Serum of HIV Infected Men Shares Epitopes with the HIV Transmembrane Protein gp41. Clin. Exp. Immunol. 71(1):13–18 (Database Biosis Online, Biosciences Information Service, Philadelphia, PA 1988).
Wang, J. M., et al. (1999) T20/DP178, An Ectodomain Peptide of HIV–1, gp41, Is a Potent Activator of Human Phagocyte N–Formyl Peptide Receptor. AIDS Pathogenesis, Keystone, CO, Jan. 7–13, 1999.

* cited by examiner

Primary Examiner—Elizabeth Kemmerer
(74) Attorney, Agent, or Firm—Knobbe, Martens, Olson & Bear, LLP

(57) ABSTRACT

The present invention relates to the discovery that T20/DP178, T21/DP107, and fragments thereof interact with members of the formyl peptide receptor family and thereby modulate cell migration and activation. Novel biological tools, prophylactics, therapeutics and methods of use of the foregoing for modulating an inflammatory response are disclosed.

5 Claims, 48 Drawing Sheets

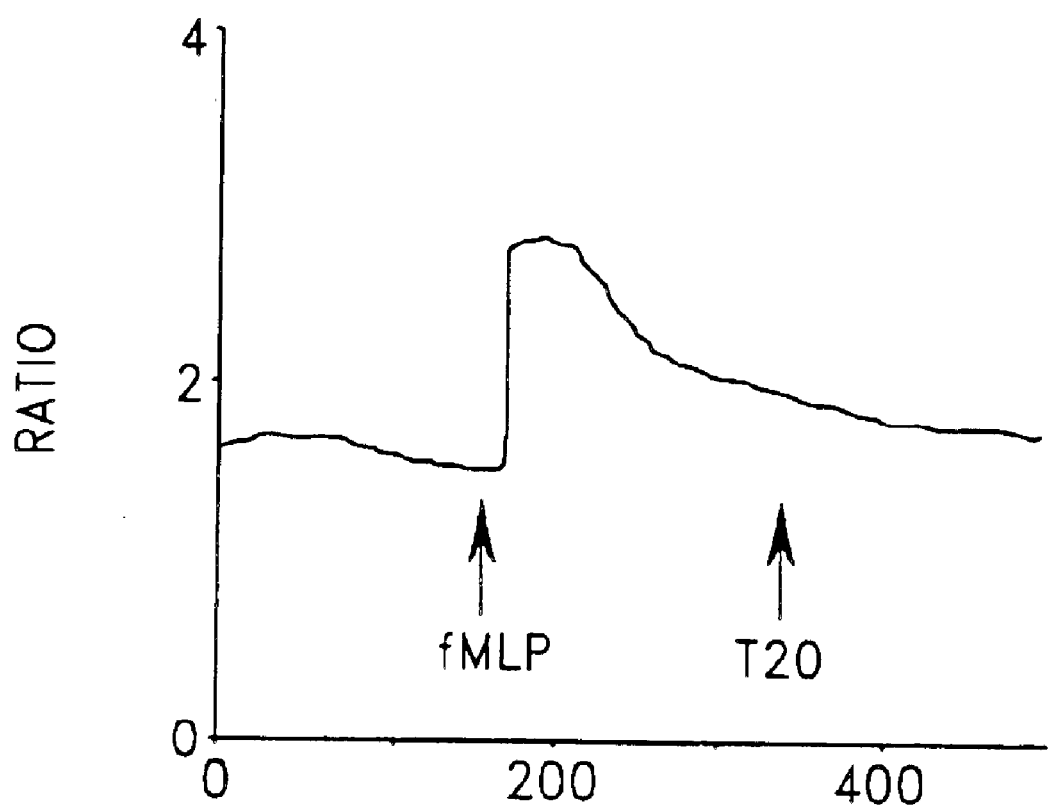
FIG.2C1

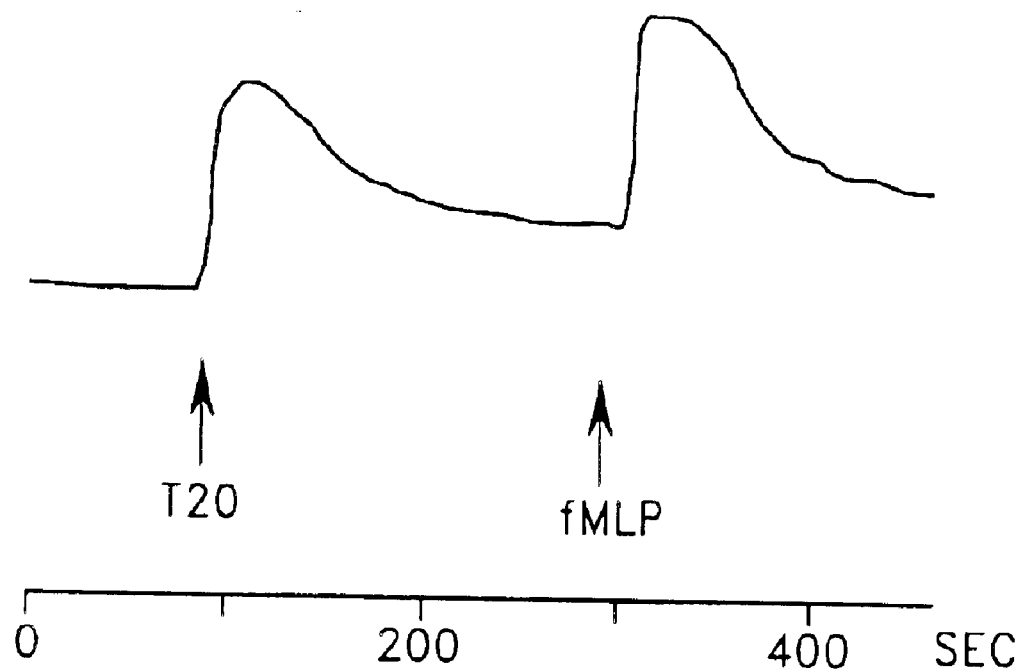
FIG.2C2

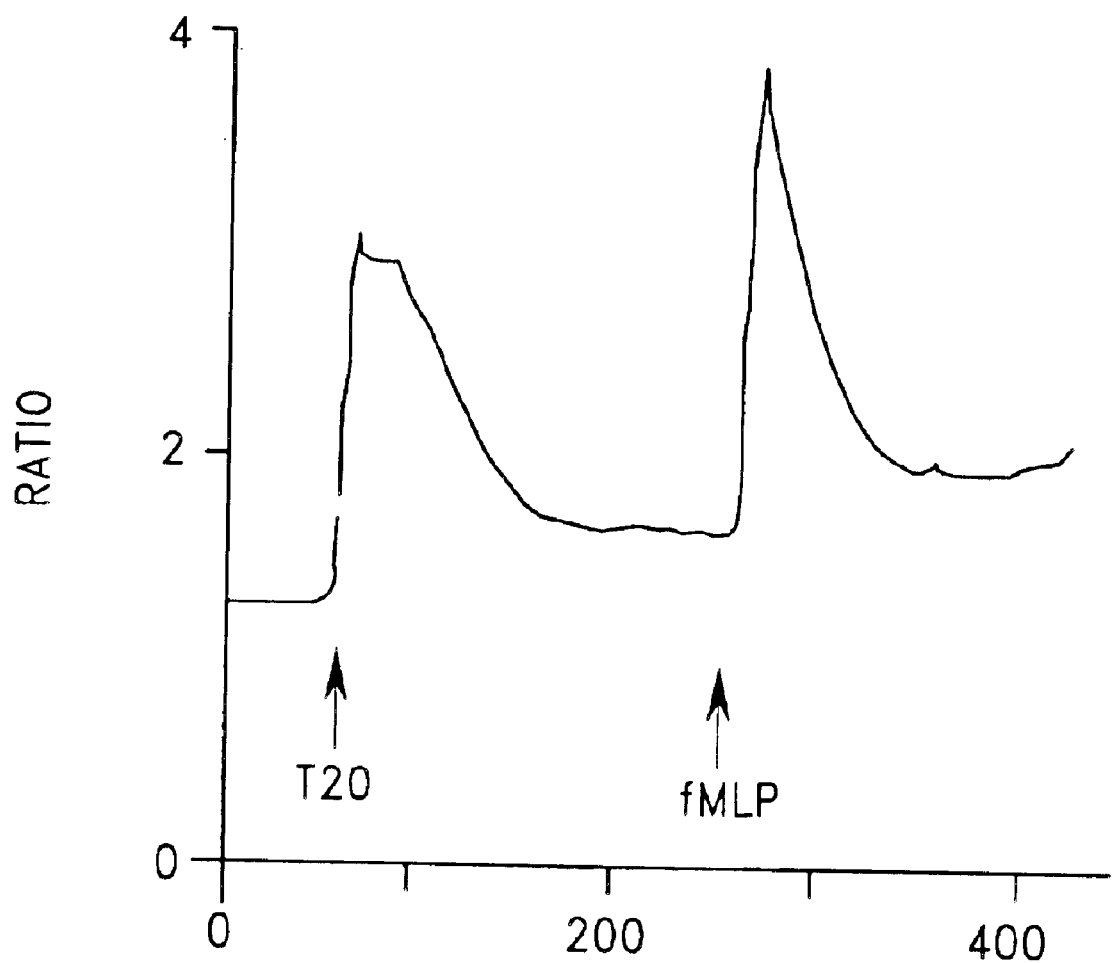
FIG.2C3

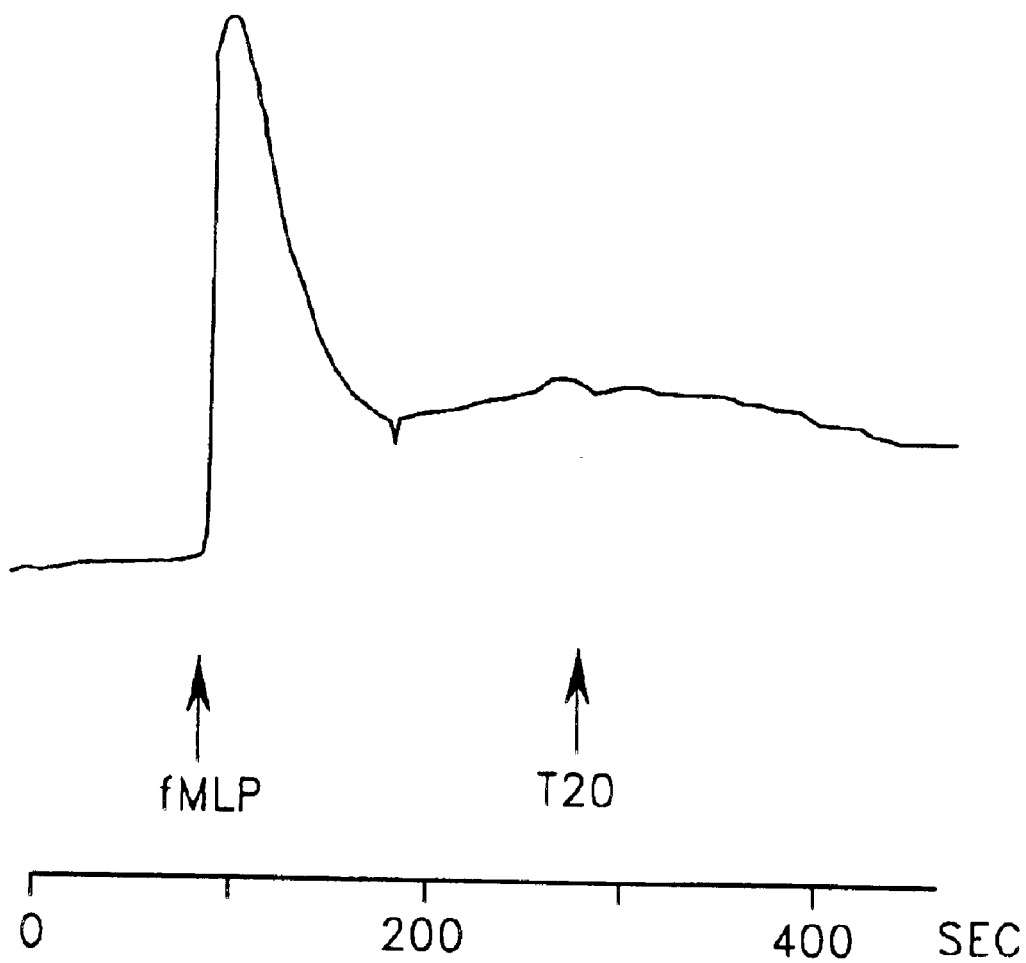
FIG.2C4

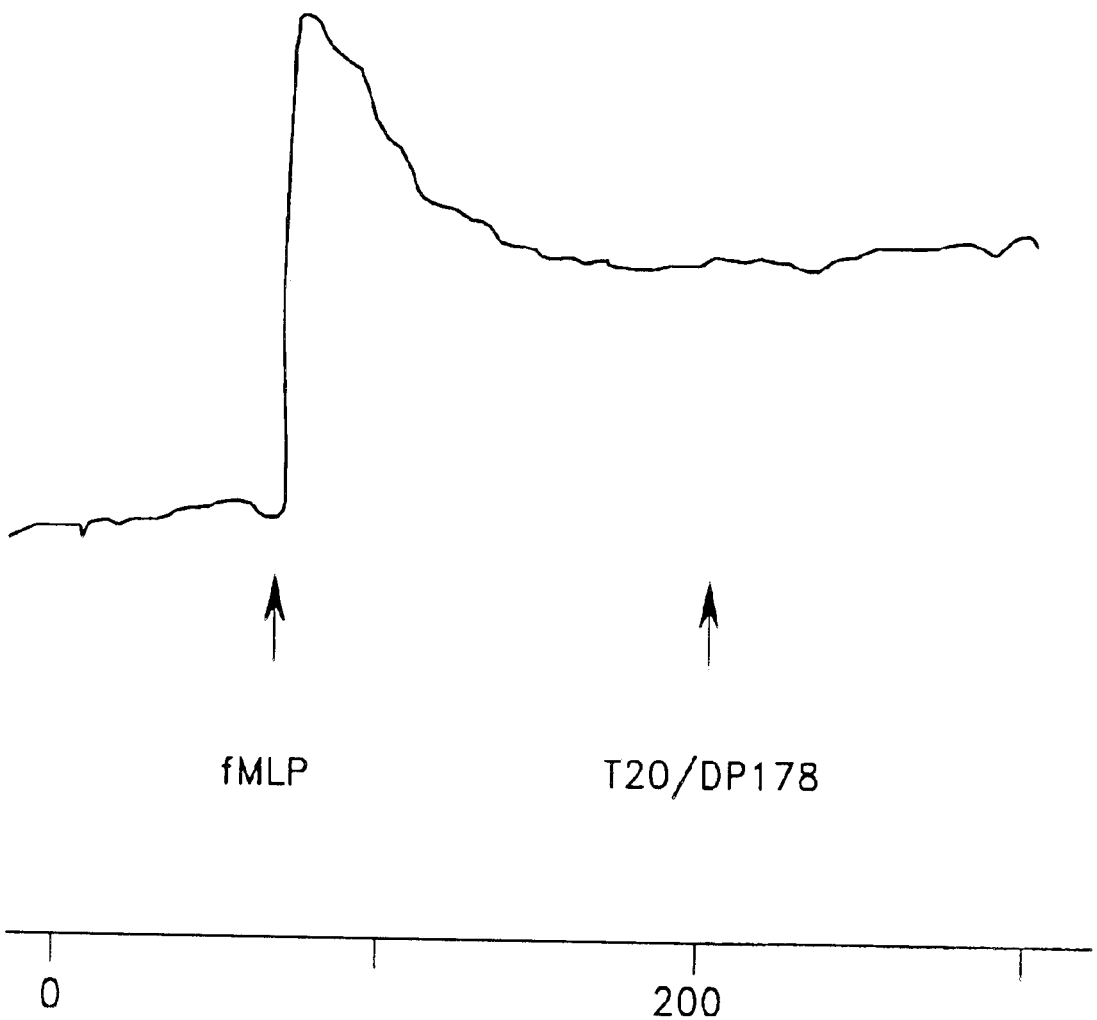
FIG.3B1

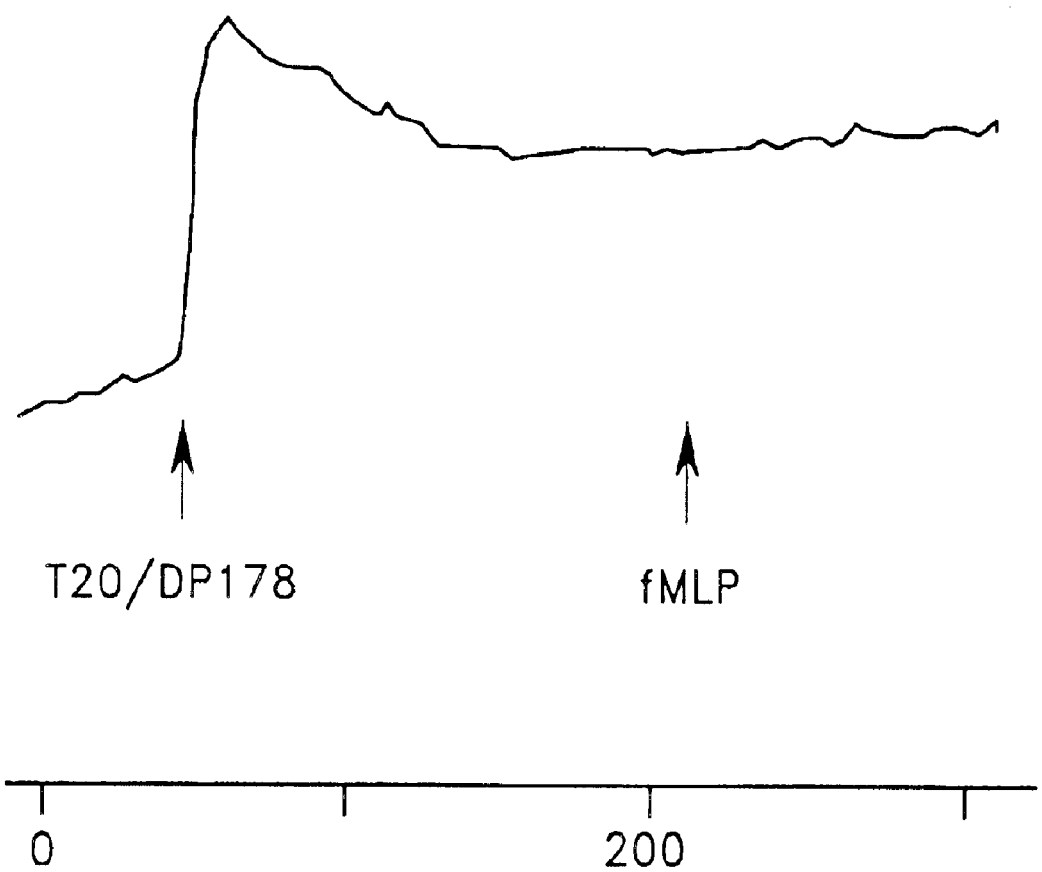
FIG. 3B2

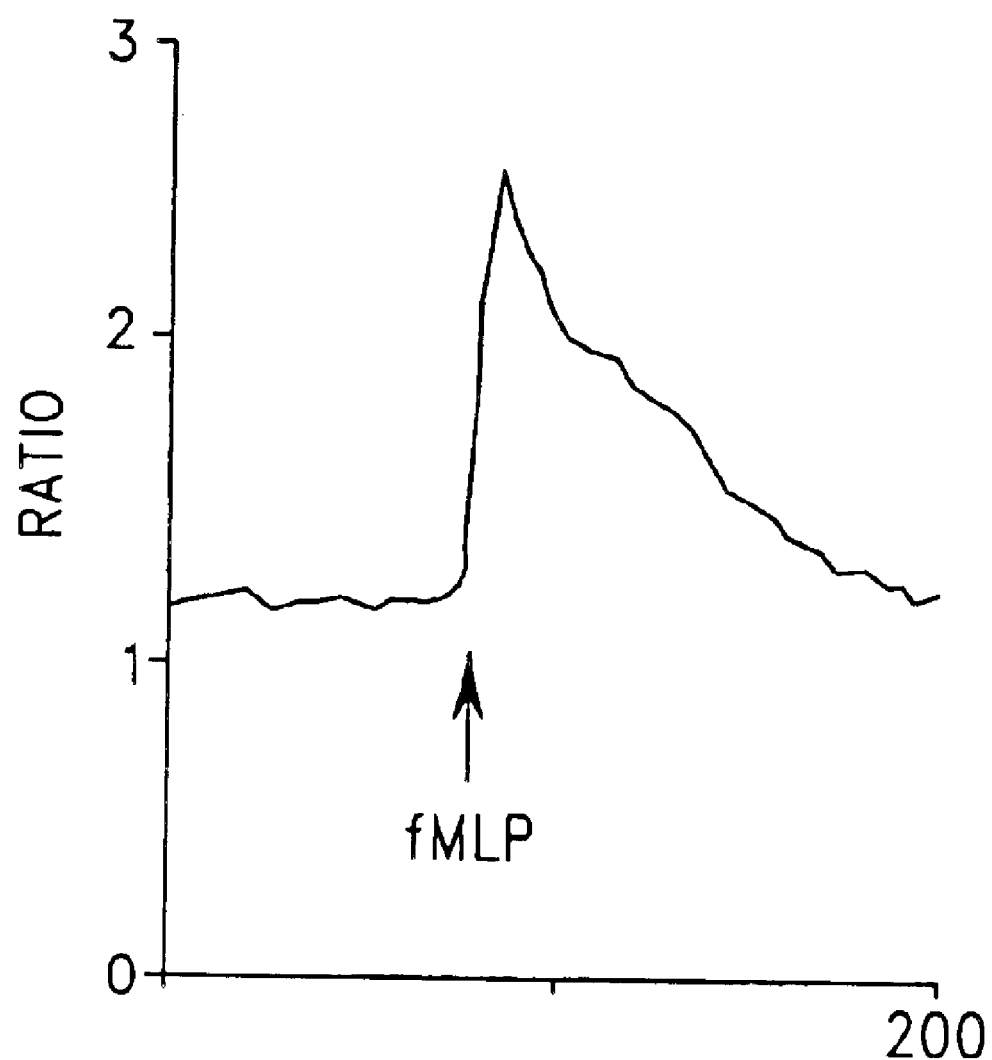
FIG. 4A1

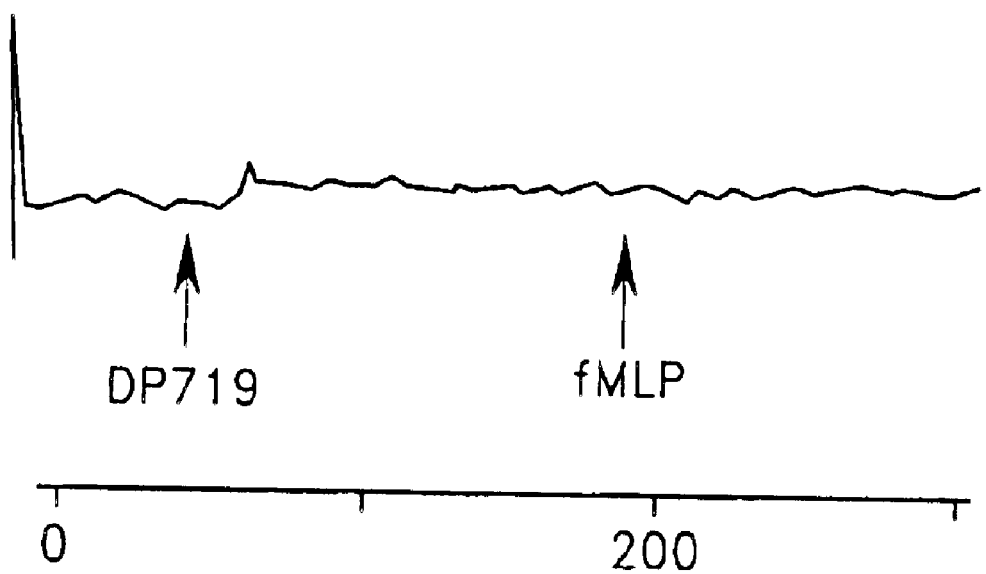
FIG. 4A2

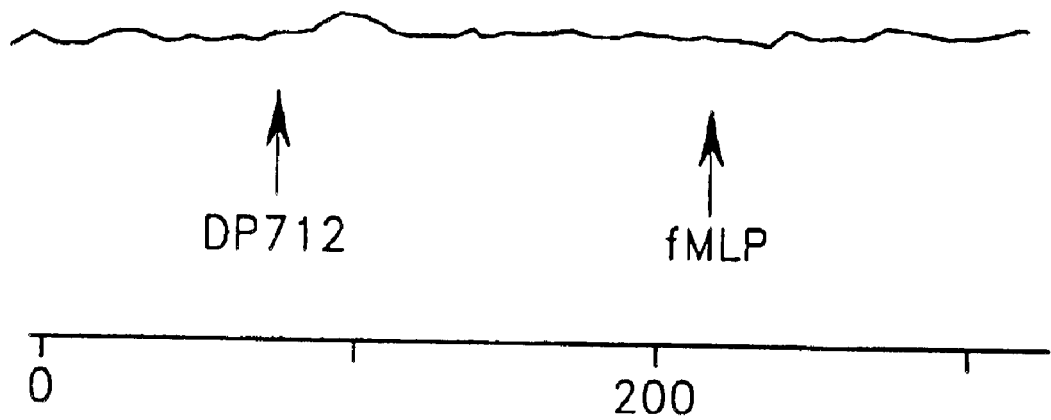
FIG.4A3

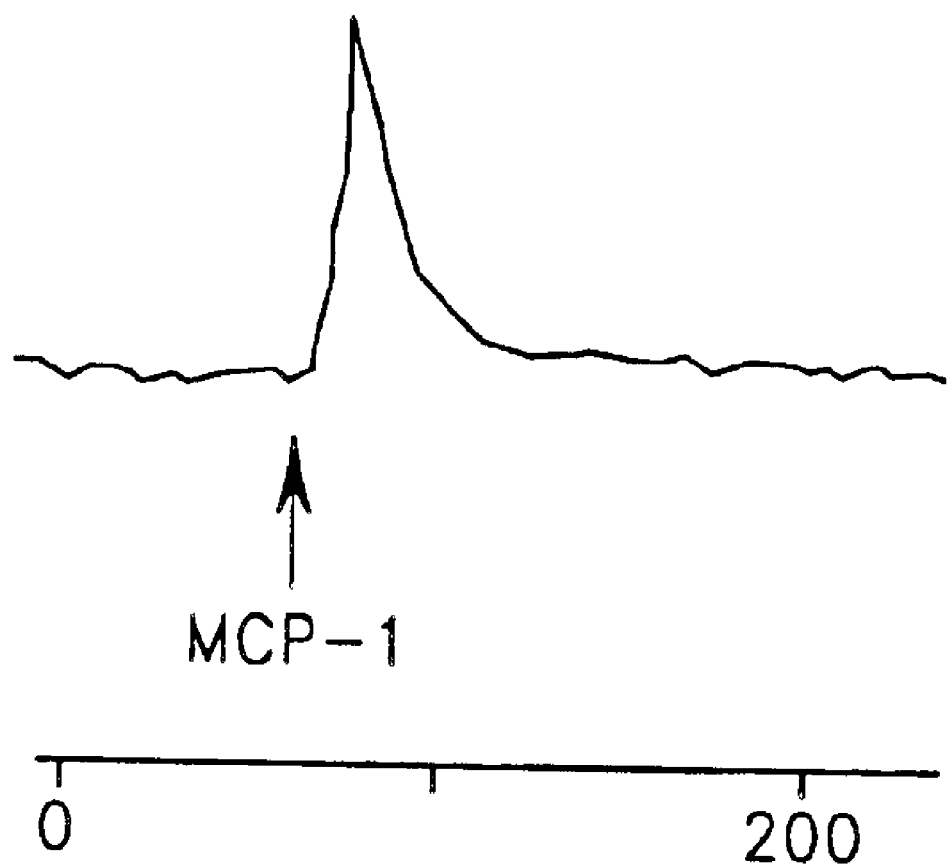
FIG.4A4

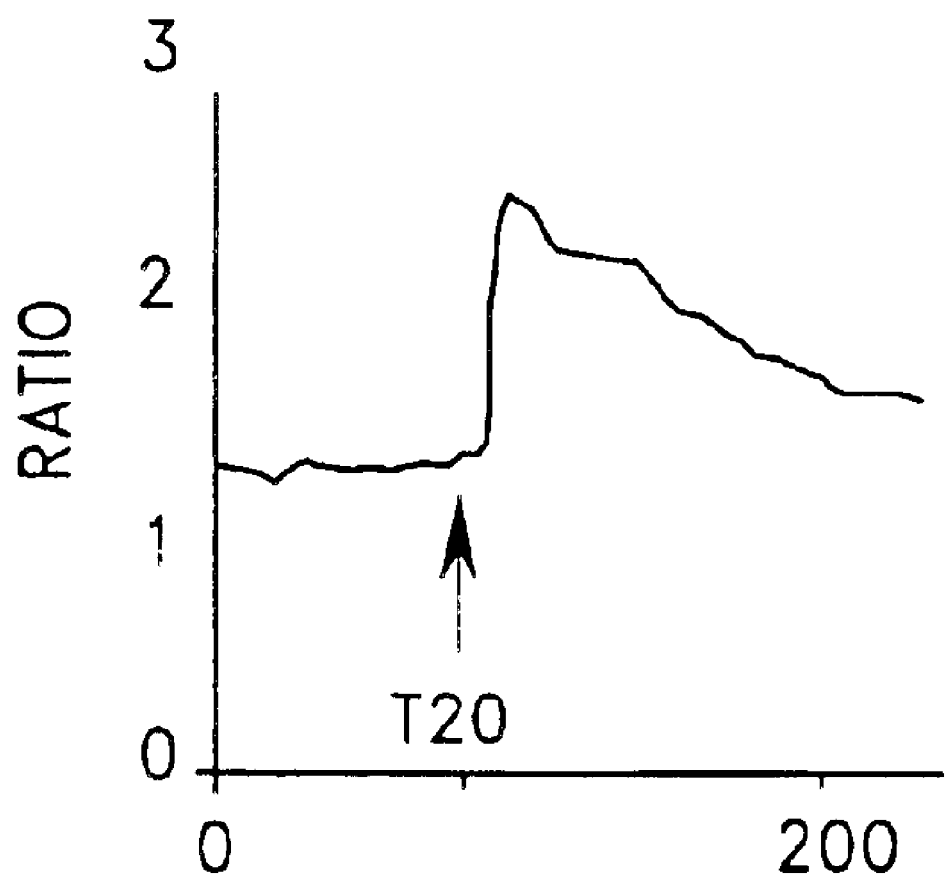
FIG. 4A5

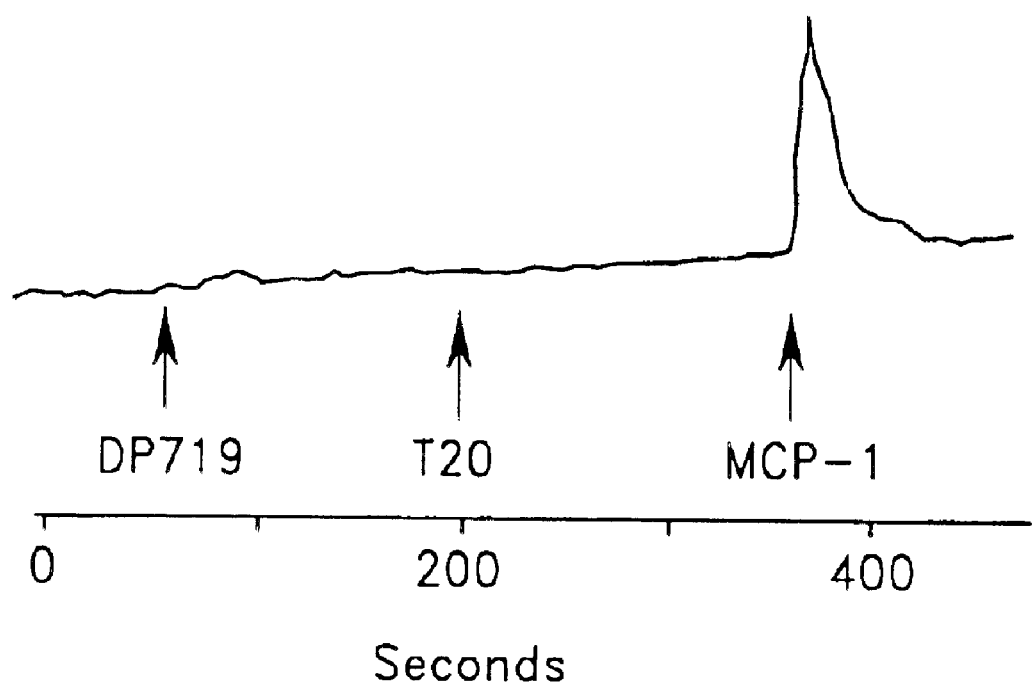
FIG. 4A6

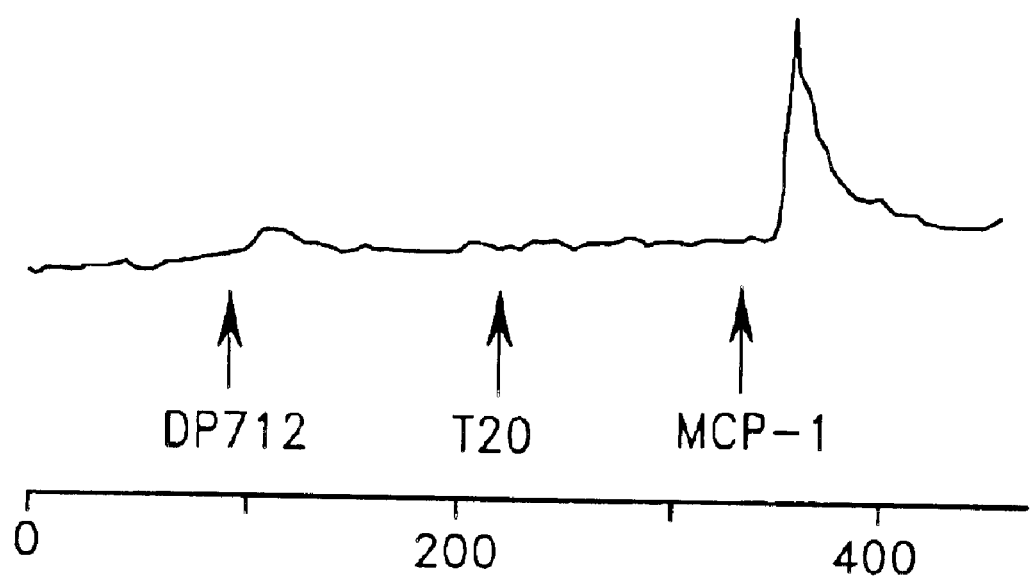
FIG. 4A7

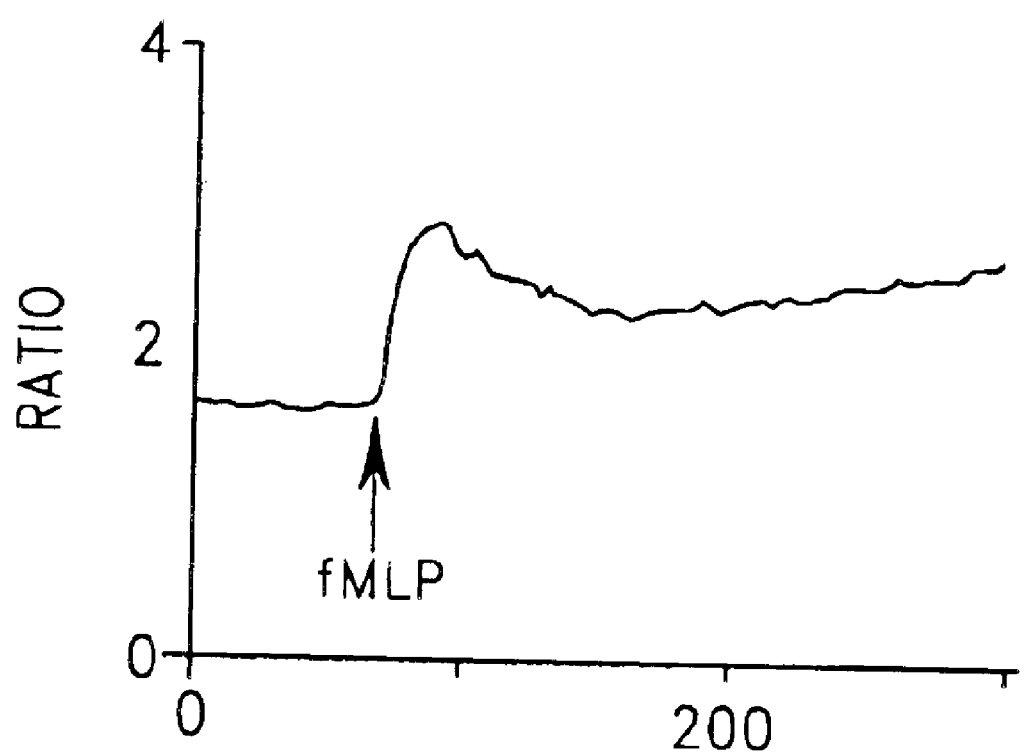
FIG. 4B1

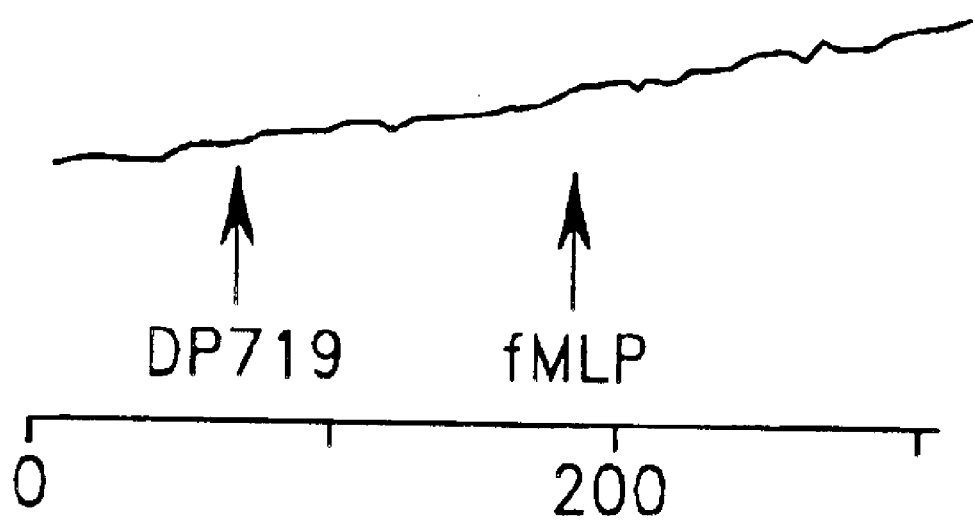
FIG.4B2

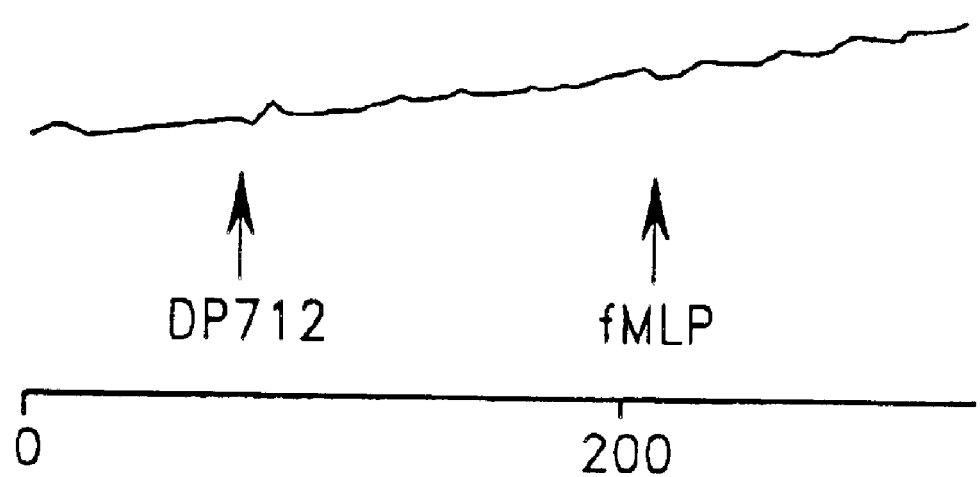
FIG.4B3

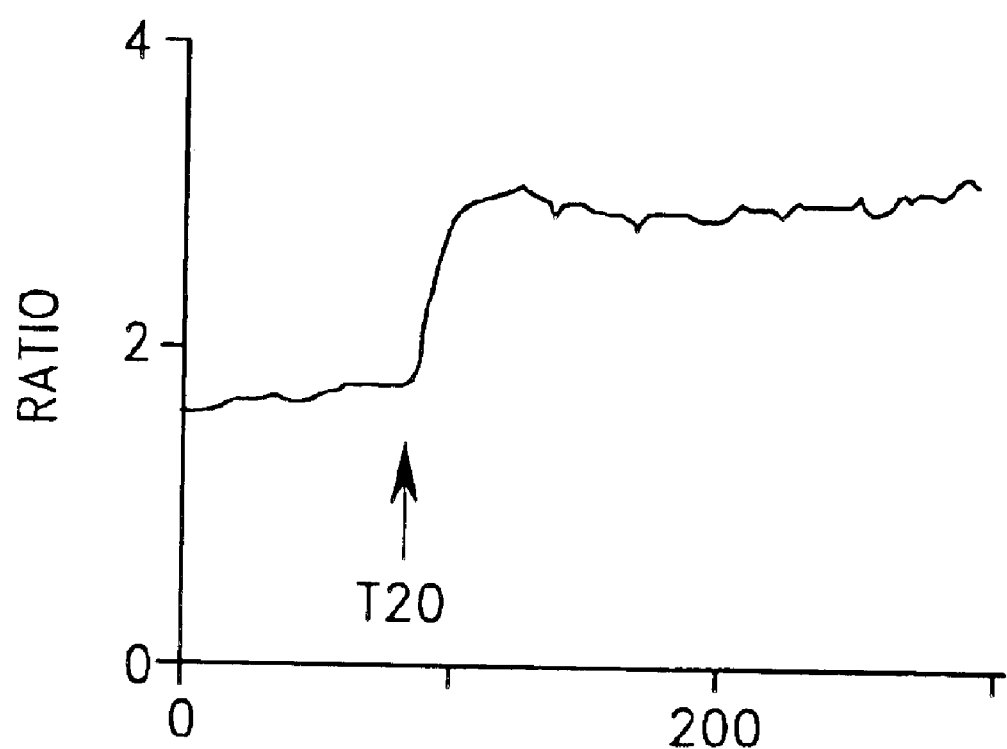
FIG. 4B4

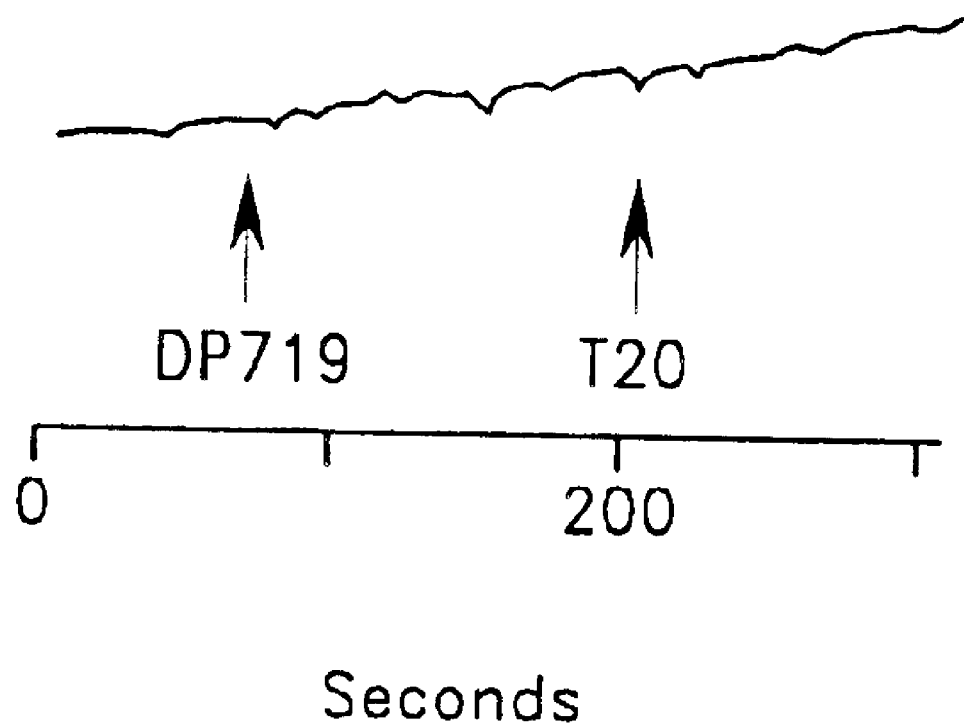
FIG.4B5

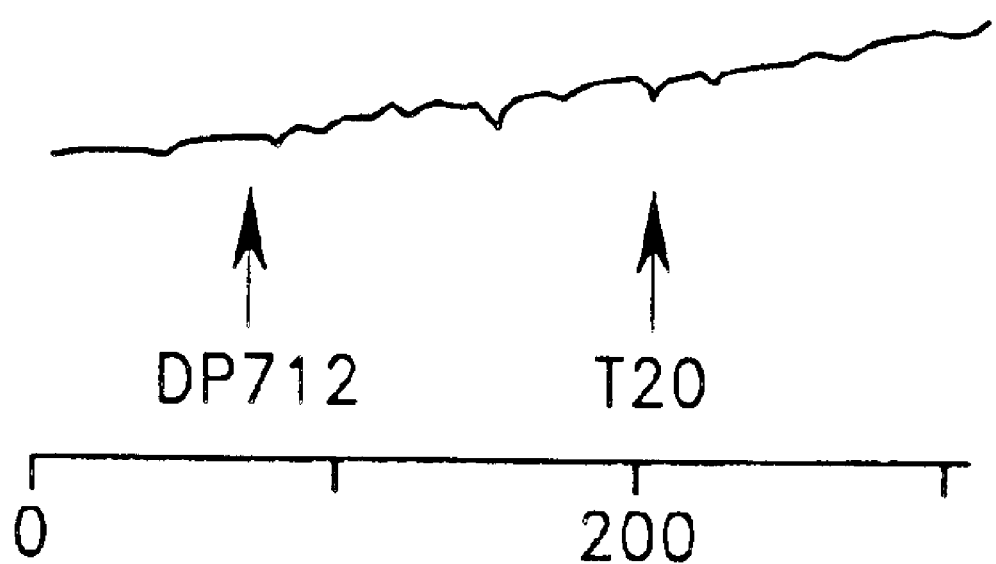
FIG.4B6

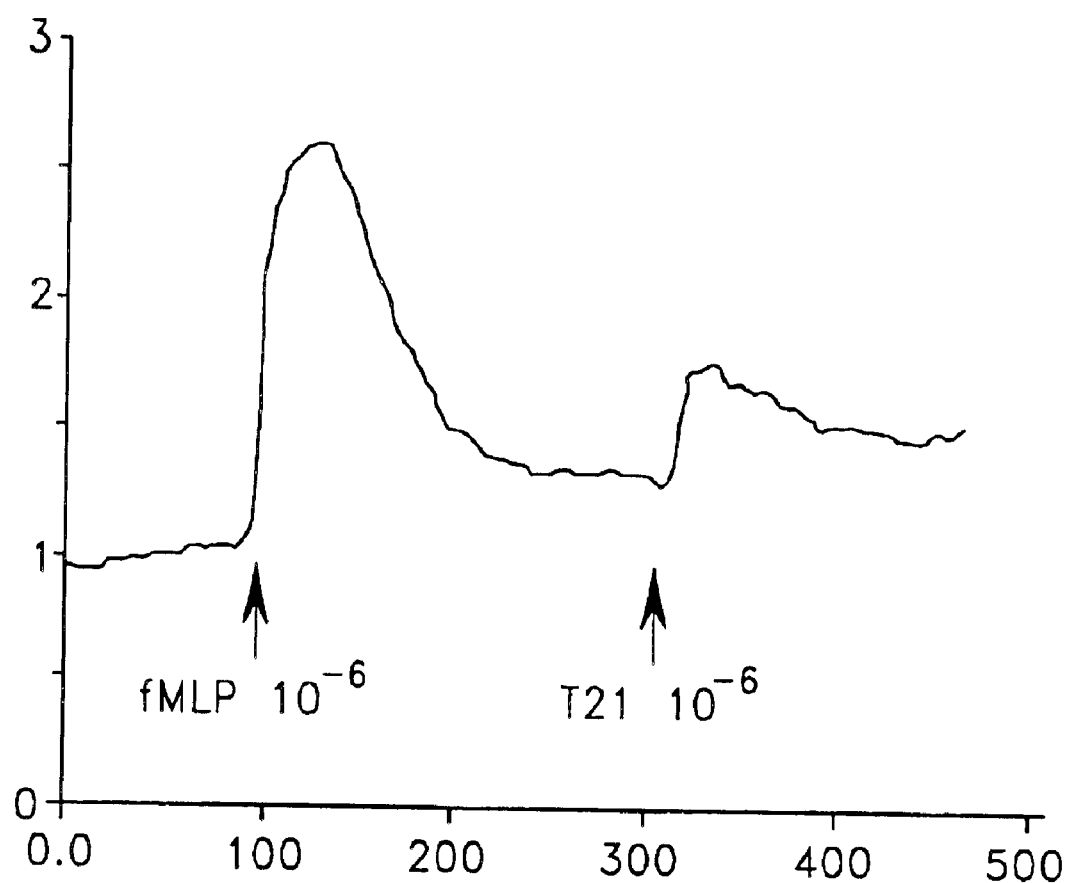
FIG.7B1

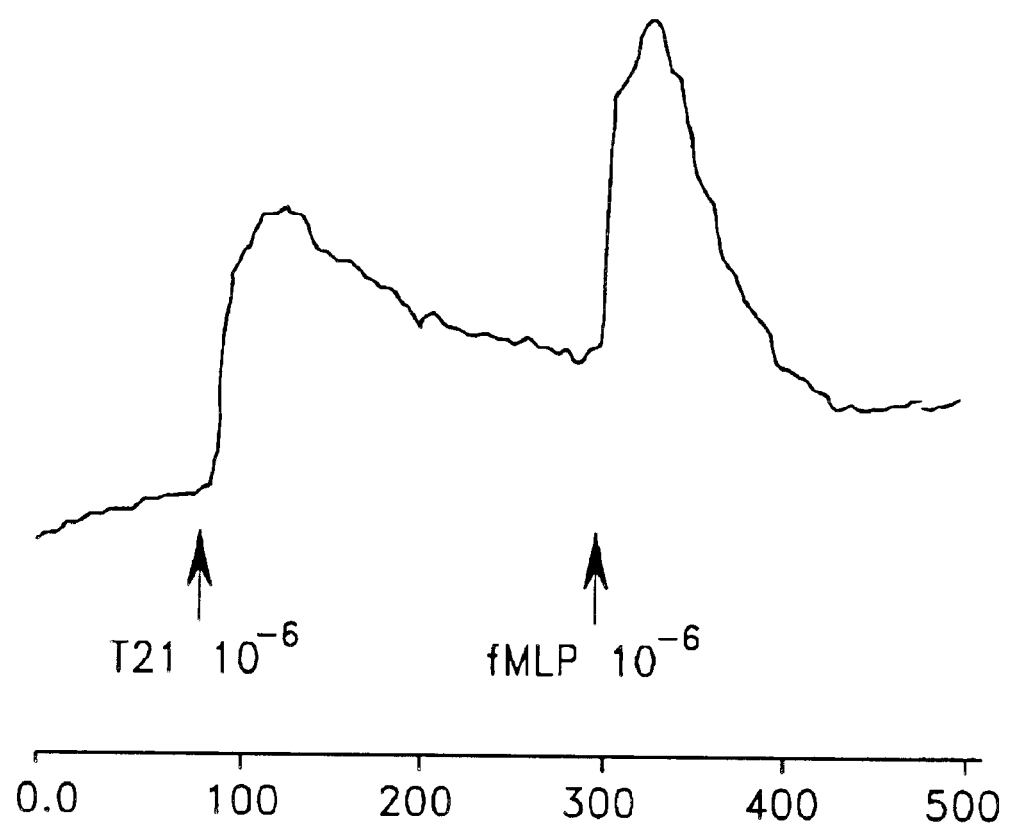
FIG. 7B2

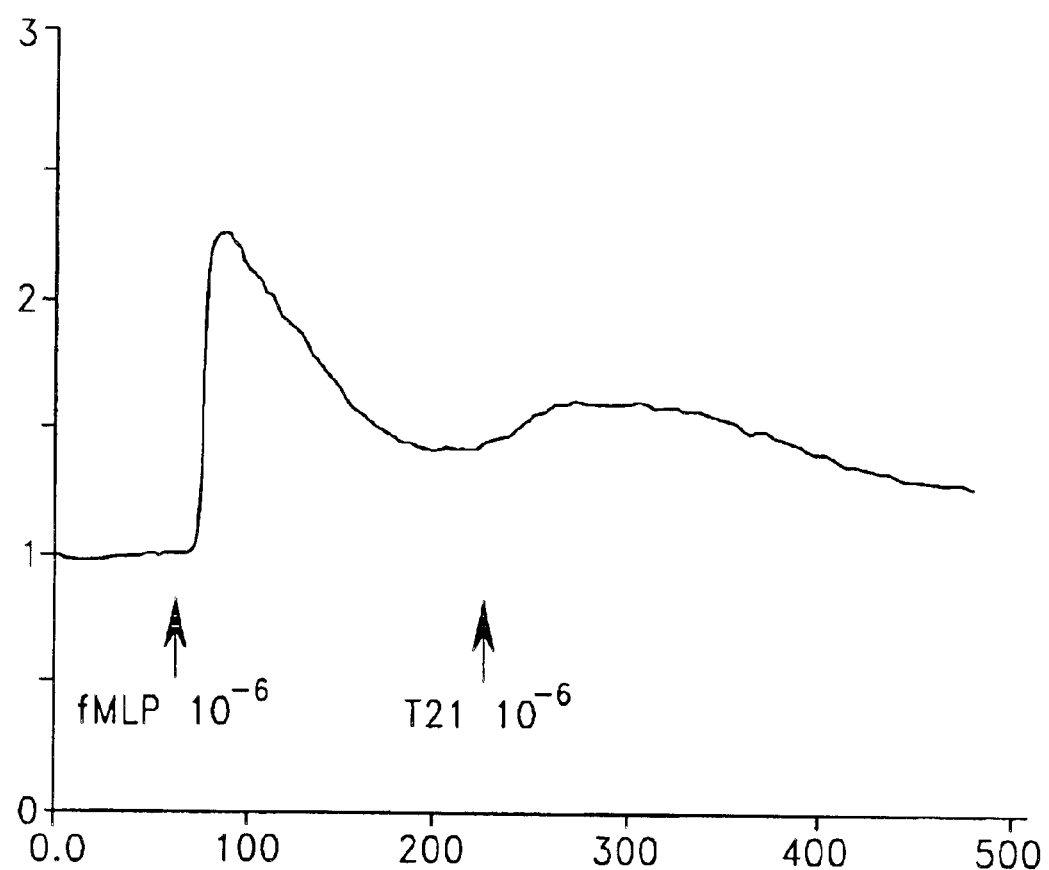
FIG. 7D1

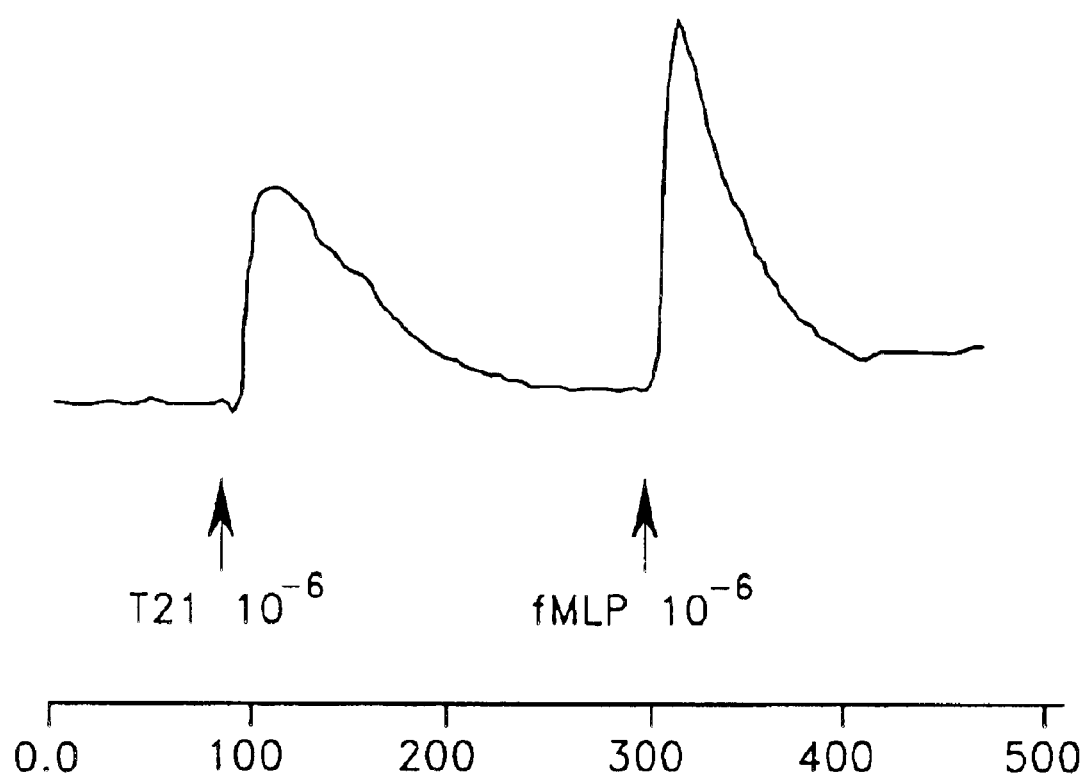
FIG. 7D2

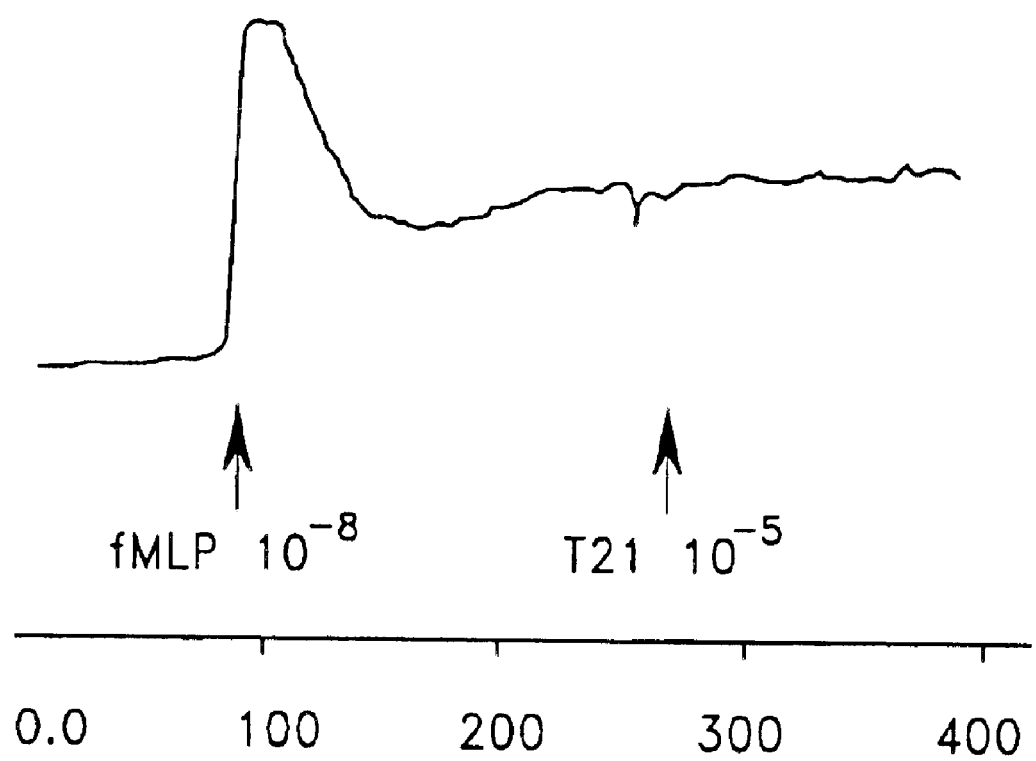
FIG. 8C1

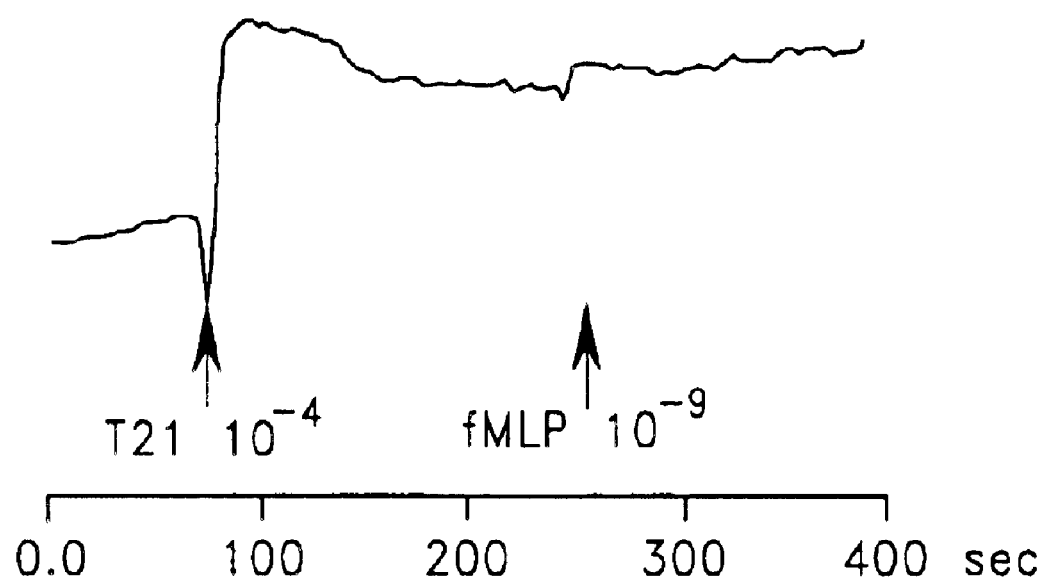
FIG.8C2

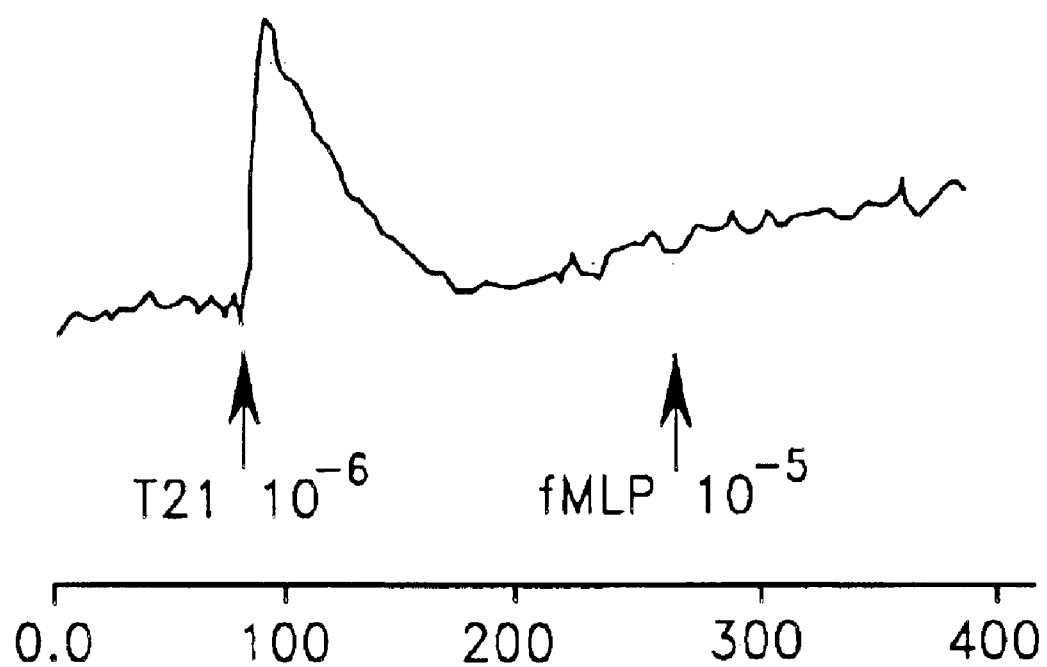
FIG.8F1

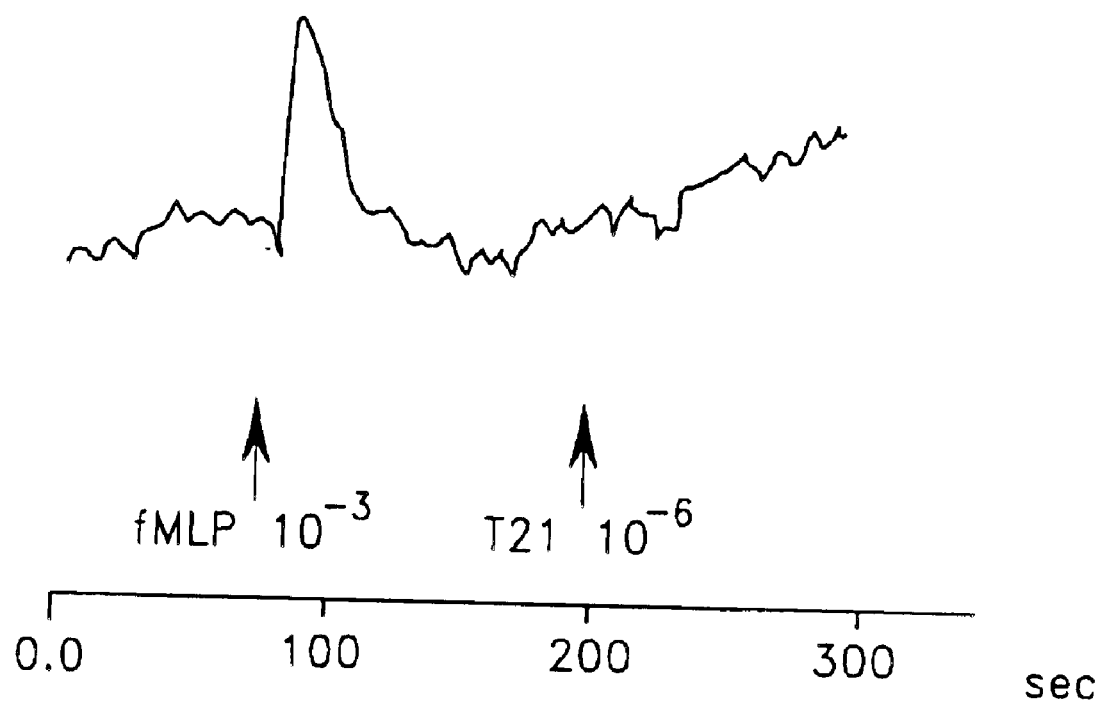
FIG. 8F2

SEQUENCE LISTING

```
<160> NUMBER OF SEQ ID NOS: 203

<210> SEQ ID NO 1
<211> LENGTH: 5
<212> TYPE: PRT
<213> ORGANISM: Artificial Sequence
<220> FEATURE:
<223> OTHER INFORMATION: Artificial Peptide

<400> SEQUENCE: 1

Met Ile Leu Phe Phe
1               5

<210> SEQ ID NO 2
<211> LENGTH: 4
<212> TYPE: PRT
<213> ORGANISM: Artificial Sequence
```

```
<220> FEATURE:
<223> OTHER INFORMATION: Artificial Peptide

<400> SEQUENCE: 2

Tyr Thr Ser Leu
 1

<210> SEQ ID NO 3
<211> LENGTH: 5
<212> TYPE: PRT
<213> ORGANISM: Artificial Sequence
<220> FEATURE:
<223> OTHER INFORMATION: Artificial Peptide

<400> SEQUENCE: 3

Tyr Thr Ser Leu Ile
 1               5

<210> SEQ ID NO 4
<211> LENGTH: 6
<212> TYPE: PRT
<213> ORGANISM: Artificial Sequence
<220> FEATURE:
<223> OTHER INFORMATION: Artificial Peptide

<400> SEQUENCE: 4

Tyr Thr Ser Leu Ile His
 1               5

<210> SEQ ID NO 5
<211> LENGTH: 7
<212> TYPE: PRT
<213> ORGANISM: Artificial Sequence
<220> FEATURE:
<223> OTHER INFORMATION: Artificial Peptide

<400> SEQUENCE: 5

Tyr Thr Ser Leu Ile His Ser
 1               5

<210> SEQ ID NO 6
<211> LENGTH: 8
<212> TYPE: PRT
<213> ORGANISM: Artificial Sequence
<220> FEATURE:
<223> OTHER INFORMATION: Artificial Peptide

<400> SEQUENCE: 6

Tyr Thr Ser Leu Ile His Ser Leu
 1               5

<210> SEQ ID NO 7
<211> LENGTH: 9
<212> TYPE: PRT
<213> ORGANISM: Artificial Sequence
<220> FEATURE:
<223> OTHER INFORMATION: Artificial Peptide

<400> SEQUENCE: 7

Tyr Thr Ser Leu Ile His Ser Leu Ile
 1               5

<210> SEQ ID NO 8
<211> LENGTH: 10
<212> TYPE: PRT
<213> ORGANISM: Artificial Sequence
<220> FEATURE:
```

<223> OTHER INFORMATION: Artificial Peptide

<400> SEQUENCE: 8

Tyr Thr Ser Leu Ile His Ser Leu Ile Glu
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: Artificial Peptide

<400> SEQUENCE: 9

Tyr Thr Ser Leu Ile His Ser Leu Ile Glu Glu
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Artificial Peptide

<400> SEQUENCE: 10

Tyr Thr Ser Leu Ile His Ser Leu Ile Glu Glu Ser
 1               5                  10

<210> SEQ ID NO 11
<211> LENGTH: 13
<212> TYPE: PRT
<213> ORGANISM: Artificial Sequence
<220> FEATURE:
<223> OTHER INFORMATION: Artificial Peptide

<400> SEQUENCE: 11

Tyr Thr Ser Leu Ile His Ser Leu Ile Glu Glu Ser Gln
 1               5                  10

<210> SEQ ID NO 12
<211> LENGTH: 14
<212> TYPE: PRT
<213> ORGANISM: Artificial Sequence
<220> FEATURE:
<223> OTHER INFORMATION: Artificial Peptide

<400> SEQUENCE: 12

Tyr Thr Ser Leu Ile His Ser Leu Ile Glu Glu Ser Gln Asn
 1               5                  10

<210> SEQ ID NO 13
<211> LENGTH: 15
<212> TYPE: PRT
<213> ORGANISM: Artificial Sequence
<220> FEATURE:
<223> OTHER INFORMATION: Artificial Peptide

<400> SEQUENCE: 13

Tyr Thr Ser Leu Ile His Ser Leu Ile Glu Glu Ser Gln Asn Gln
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: Artificial Peptide -continued

<400> SEQUENCE: 14

Tyr Thr Ser Leu Ile His Ser Leu Ile Glu Glu Ser Gln Asn Gln Gln
1               5                   10                  15

<210> SEQ ID NO 15
<211> LENGTH: 17
<212> TYPE: PRT
<213> ORGANISM: Artificial Sequence
<220> FEATURE:
<223> OTHER INFORMATION: Artificial Peptide

<400> SEQUENCE: 15

Tyr Thr Ser Leu Ile His Ser Leu Ile Glu Glu Ser Gln Asn Gln Gln
1               5                   10                  15

Glu

<210> SEQ ID NO 16
<211> LENGTH: 18
<212> TYPE: PRT
<213> ORGANISM: Artificial Sequence
<220> FEATURE:
<223> OTHER INFORMATION: Artificial Peptide

<400> SEQUENCE: 16

Tyr Thr Ser Leu Ile His Ser Leu Ile Glu Glu Ser Gln Asn Gln Gln
1               5                   10                  15

Glu Lys

<210> SEQ ID NO 17
<211> LENGTH: 19
<212> TYPE: PRT
<213> ORGANISM: Artificial Sequence
<220> FEATURE:
<223> OTHER INFORMATION: Artificial Peptide

<400> SEQUENCE: 17

Tyr Thr Ser Leu Ile His Ser Leu Ile Glu Glu Ser Gln Asn Gln Gln
1               5                   10                  15

Glu Lys Asn

<210> SEQ ID NO 18
<211> LENGTH: 20
<212> TYPE: PRT
<213> ORGANISM: Artificial Sequence
<220> FEATURE:
<223> OTHER INFORMATION: Artificial Peptide

<400> SEQUENCE: 18

Tyr Thr Ser Leu Ile His Ser Leu Ile Glu Glu Ser Gln Asn Gln Gln
1               5                   10                  15

Glu Lys Asn Glu
            20

<210> SEQ ID NO 19
<211> LENGTH: 21
<212> TYPE: PRT
<213> ORGANISM: Artificial Sequence
<220> FEATURE:
<223> OTHER INFORMATION: Artificial Peptide

<400> SEQUENCE: 19

Tyr Thr Ser Leu Ile His Ser Leu Ile Glu Glu Ser Gln Asn Gln Gln
1               5                   10                  15

Glu Lys Asn Glu Gln
         20

<210> SEQ ID NO 20
<211> LENGTH: 22
<212> TYPE: PRT
<213> ORGANISM: Artificial Sequence
<220> FEATURE:
<223> OTHER INFORMATION: Artificial Peptide

<400> SEQUENCE: 20

Tyr Thr Ser Leu Ile His Ser Leu Ile Glu Glu Ser Gln Asn Gln Gln
 1               5                  10                  15

Glu Lys Asn Glu Gln Glu
         20

<210> SEQ ID NO 21
<211> LENGTH: 23
<212> TYPE: PRT
<213> ORGANISM: Artificial Sequence
<220> FEATURE:
<223> OTHER INFORMATION: Artificial Peptide

<400> SEQUENCE: 21

Tyr Thr Ser Leu Ile His Ser Leu Ile Glu Glu Ser Gln Asn Gln Gln
 1               5                  10                  15

Glu Lys Asn Glu Gln Glu Leu
         20

<210> SEQ ID NO 22
<211> LENGTH: 24
<212> TYPE: PRT
<213> ORGANISM: Artificial Sequence
<220> FEATURE:
<223> OTHER INFORMATION: Artificial Peptide

<400> SEQUENCE: 22

Tyr Thr Ser Leu Ile His Ser Leu Ile Glu Glu Ser Gln Asn Gln Gln
 1               5                  10                  15

Glu Lys Asn Glu Gln Glu Leu Leu
         20

<210> SEQ ID NO 23
<211> LENGTH: 25
<212> TYPE: PRT
<213> ORGANISM: Artificial Sequence
<220> FEATURE:
<223> OTHER INFORMATION: Artificial Peptide

<400> SEQUENCE: 23

Tyr Thr Ser Leu Ile His Ser Leu Ile Glu Glu Ser Gln Asn Gln Gln
 1               5                  10                  15

Glu Lys Asn Glu Gln Glu Leu Leu Glu
         20                  25

<210> SEQ ID NO 24
<211> LENGTH: 25
<212> TYPE: PRT
<213> ORGANISM: Artificial Sequence
<220> FEATURE:
<223> OTHER INFORMATION: Artificial Peptide

<400> SEQUENCE: 24

Tyr Thr Ser Leu Ile His Ser Leu Ile Glu Glu Ser Gln Asn Gln Gln
 1               5                  10                  15

```
1               5                  10                 15
Glu Lys Asn Glu Gln Glu Leu Leu Glu
            20                  25
```

<210> SEQ ID NO 25
<211> LENGTH: 27
<212> TYPE: PRT
<213> ORGANISM: Artificial Sequence
<220> FEATURE:
<223> OTHER INFORMATION: Artificial Peptide

<400> SEQUENCE: 25

```
Tyr Thr Ser Leu Ile His Ser Leu Ile Glu Glu Ser Gln Asn Gln Gln
 1               5                  10                 15
Glu Lys Asn Glu Gln Glu Leu Leu Glu Leu Asp
            20                  25
```

<210> SEQ ID NO 26
<211> LENGTH: 28
<212> TYPE: PRT
<213> ORGANISM: Artificial Sequence
<220> FEATURE:
<223> OTHER INFORMATION: Artificial Peptide

<400> SEQUENCE: 26

```
Tyr Thr Ser Leu Ile His Ser Leu Ile Glu Glu Ser Gln Asn Gln Gln
 1               5                  10                 15
Glu Lys Asn Glu Gln Glu Leu Leu Glu Leu Asp Lys
            20                  25
```

<210> SEQ ID NO 27
<211> LENGTH: 29
<212> TYPE: PRT
<213> ORGANISM: Artificial Sequence
<220> FEATURE:
<223> OTHER INFORMATION: Artificial Peptide

<400> SEQUENCE: 27

```
Tyr Thr Ser Leu Ile His Ser Leu Ile Glu Glu Ser Gln Asn Gln Gln
 1               5                  10                 15
Glu Lys Asn Glu Gln Glu Leu Leu Glu Leu Asp Lys Trp
            20                  25
```

<210> SEQ ID NO 28
<211> LENGTH: 30
<212> TYPE: PRT
<213> ORGANISM: Artificial Sequence
<220> FEATURE:
<223> OTHER INFORMATION: Artificial Peptide

<400> SEQUENCE: 28

```
Tyr Thr Ser Leu Ile His Ser Leu Ile Glu Glu Ser Gln Asn Gln Gln
 1               5                  10                 15
Glu Lys Asn Glu Gln Glu Leu Leu Glu Leu Asp Lys Trp Ala
            20                  25                 30
```

<210> SEQ ID NO 29
<211> LENGTH: 31
<212> TYPE: PRT
<213> ORGANISM: Artificial Sequence
<220> FEATURE:
<223> OTHER INFORMATION: Artificial Peptide

<400> SEQUENCE: 29

-continued

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Artificial Peptide

<400> SEQUENCE: 30

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

<210> SEQ ID NO 31
<211> LENGTH: 33
<212> TYPE: PRT
<213> ORGANISM: Artificial Sequence
<220> FEATURE:
<223> OTHER INFORMATION: Artificial Peptide

<400> SEQUENCE: 31

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp

<210> SEQ ID NO 32
<211> LENGTH: 34
<212> TYPE: PRT
<213> ORGANISM: Artificial Sequence
<220> FEATURE:
<223> OTHER INFORMATION: Artificial Peptide

<400> SEQUENCE: 32

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn

<210> SEQ ID NO 33
<211> LENGTH: 35
<212> TYPE: PRT
<213> ORGANISM: Artificial Sequence
<220> FEATURE:
<223> OTHER INFORMATION: Artificial Peptide

<400> SEQUENCE: 33

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp
        35

<210> SEQ ID NO 34

<211> LENGTH: 36
<212> TYPE: PRT
<213> ORGANISM: Artificial Sequence
<220> FEATURE:
<223> OTHER INFORMATION: Artificial Peptide

<400> SEQUENCE: 34

Tyr Thr Ser Leu Ile His Ser Leu Ile Glu Glu Ser Gln Asn Gln Gln
 1               5                  10                  15
Glu Lys Asn Glu Gln Glu Leu Leu Glu Leu Asp Lys Trp Ala Ser Leu
            20                  25                  30
Trp Asn Trp Phe
         35

<210> SEQ ID NO 35
<211> LENGTH: 4
<212> TYPE: PRT
<213> ORGANISM: Artificial Sequence
<220> FEATURE:
<223> OTHER INFORMATION: Artificial Peptide

<400> SEQUENCE: 35

Trp Asn Trp Phe
 1

<210> SEQ ID NO 36
<211> LENGTH: 5
<212> TYPE: PRT
<213> ORGANISM: Artificial Sequence
<220> FEATURE:
<223> OTHER INFORMATION: Artificial Peptide

<400> SEQUENCE: 36

Leu Trp Asn Trp Phe
 1               5

<210> SEQ ID NO 37
<211> LENGTH: 6
<212> TYPE: PRT
<213> ORGANISM: Artificial Sequence
<220> FEATURE:
<223> OTHER INFORMATION: Artificial Peptide

<400> SEQUENCE: 37

Ser Leu Trp Asn Trp Phe
 1               5

<210> SEQ ID NO 38
<211> LENGTH: 7
<212> TYPE: PRT
<213> ORGANISM: Artificial Sequence
<220> FEATURE:
<223> OTHER INFORMATION: Artificial Peptide

<400> SEQUENCE: 38

Ala Ser Leu Trp Asn Trp Phe
 1               5

<210> SEQ ID NO 39
<211> LENGTH: 8
<212> TYPE: PRT
<213> ORGANISM: Artificial Sequence
<220> FEATURE:
<223> OTHER INFORMATION: Artificial Peptide

<400> SEQUENCE: 39

```
Trp Ala Ser Leu Trp Asn Trp Phe
1               5
```

<210> SEQ ID NO 40
<211> LENGTH: 9
<212> TYPE: PRT
<213> ORGANISM: Artificial Sequence
<220> FEATURE:
<223> OTHER INFORMATION: Artificial Peptide

<400> SEQUENCE: 40

```
Lys Trp Ala Ser Leu Trp Asn Trp Phe
1               5
```

<210> SEQ ID NO 41
<211> LENGTH: 10
<212> TYPE: PRT
<213> ORGANISM: Artificial Sequence
<220> FEATURE:
<223> OTHER INFORMATION: Artificial Peptide

<400> SEQUENCE: 41

```
Asp Lys Trp Ala Ser Leu Trp Asn Trp Phe
1               5                   10
```

<210> SEQ ID NO 42
<211> LENGTH: 11
<212> TYPE: PRT
<213> ORGANISM: Artificial Sequence
<220> FEATURE:
<223> OTHER INFORMATION: Artificial Peptide

<400> SEQUENCE: 42

```
Leu Asp Lys Trp Ala Ser Leu Trp Asn Trp Phe
1               5                   10
```

<210> SEQ ID NO 43
<211> LENGTH: 12
<212> TYPE: PRT
<213> ORGANISM: Artificial Sequence
<220> FEATURE:
<223> OTHER INFORMATION: Artificial Peptide

<400> SEQUENCE: 43

```
Glu Leu Asp Lys Trp Ala Ser Leu Trp Asn Trp Phe
1               5                   10
```

<210> SEQ ID NO 44
<211> LENGTH: 13
<212> TYPE: PRT
<213> ORGANISM: Artificial Sequence
<220> FEATURE:
<223> OTHER INFORMATION: Artificial Peptide

<400> SEQUENCE: 44

```
Leu Glu Leu Asp Lys Trp Ala Ser Leu Trp Asn Trp Phe
1               5                   10
```

<210> SEQ ID NO 45
<211> LENGTH: 14
<212> TYPE: PRT
<213> ORGANISM: Artificial Sequence
<220> FEATURE:
<223> OTHER INFORMATION: Artificial Peptide

<400> SEQUENCE: 45

```
Leu Leu Glu Leu Asp Lys Trp Ala Ser Leu Trp Asn Trp Phe
```

-continued

<210> SEQ ID NO 46
<211> LENGTH: 15
<212> TYPE: PRT
<213> ORGANISM: Artificial Sequence
<220> FEATURE:
<223> OTHER INFORMATION: Artificial Peptide

<400> SEQUENCE: 46

Glu Leu Leu Glu Leu Asp Lys Trp Ala Ser Leu Trp Asn Trp Phe
 1               5                  10                  15

<210> SEQ ID NO 47
<211> LENGTH: 16
<212> TYPE: PRT
<213> ORGANISM: Artificial Sequence
<220> FEATURE:
<223> OTHER INFORMATION: Artificial Peptide

<400> SEQUENCE: 47

Gln Glu Leu Leu Glu Leu Asp Lys Trp Ala Ser Leu Trp Asn Trp Phe
 1               5                  10                  15

<210> SEQ ID NO 48
<211> LENGTH: 17
<212> TYPE: PRT
<213> ORGANISM: Artificial Sequence
<220> FEATURE:
<223> OTHER INFORMATION: Artificial Peptide

<400> SEQUENCE: 48

Glu Gln Glu Leu Leu Glu Leu Asp Lys Trp Ala Ser Leu Trp Asn Trp
 1               5                  10                  15

Phe

<210> SEQ ID NO 49
<211> LENGTH: 18
<212> TYPE: PRT
<213> ORGANISM: Artificial Sequence
<220> FEATURE:
<223> OTHER INFORMATION: Artificial Peptide

<400> SEQUENCE: 49

Asn Glu Gln Glu Leu Leu Glu Leu Asp Lys Trp Ala Ser Leu Trp Asn
 1               5                  10                  15

Trp Phe

<210> SEQ ID NO 50
<211> LENGTH: 19
<212> TYPE: PRT
<213> ORGANISM: Artificial Sequence
<220> FEATURE:
<223> OTHER INFORMATION: Artificial Peptide

<400> SEQUENCE: 50

Lys Asn Glu Gln Glu Leu Leu Glu Leu Asp Lys Trp Ala Ser Leu Trp
 1               5                  10                  15

Asn Trp Phe

<210> SEQ ID NO 51
<211> LENGTH: 20
<212> TYPE: PRT
<213> ORGANISM: Artificial Sequence
<220> FEATURE:

<223> OTHER INFORMATION: Artificial Peptide

<400> SEQUENCE: 51

Glu Lys Asn Glu Gln Glu Leu Leu Glu Leu Asp Lys Trp Ala Ser Leu
1               5                   10                  15

Trp Asn Trp Phe
            20

<210> SEQ ID NO 52
<211> LENGTH: 21
<212> TYPE: PRT
<213> ORGANISM: Artificial Sequence
<220> FEATURE:
<223> OTHER INFORMATION: Artificial Peptide

<400> SEQUENCE: 52

Gln Glu Lys Asn Glu Gln Glu Leu Leu Glu Leu Asp Lys Trp Ala Ser
1               5                   10                  15

Leu Trp Asn Trp Phe
            20

<210> SEQ ID NO 53
<211> LENGTH: 22
<212> TYPE: PRT
<213> ORGANISM: Artificial Sequence
<220> FEATURE:
<223> OTHER INFORMATION: Artificial Peptide

<400> SEQUENCE: 53

Gln Gln Glu Lys Asn Glu Gln Glu Leu Leu Glu Leu Asp Lys Trp Ala
1               5                   10                  15

Ser Leu Trp Asn Trp Phe
            20

<210> SEQ ID NO 54
<211> LENGTH: 23
<212> TYPE: PRT
<213> ORGANISM: Artificial Sequence
<220> FEATURE:
<223> OTHER INFORMATION: Artificial Peptide

<400> SEQUENCE: 54

Asn Gln Gln Glu Lys Asn Glu Gln Glu Leu Leu Glu Leu Asp Lys Trp
1               5                   10                  15

Ala Ser Leu Trp Asn Trp Phe
            20

<210> SEQ ID NO 55
<211> LENGTH: 24
<212> TYPE: PRT
<213> ORGANISM: Artificial Sequence
<220> FEATURE:
<223> OTHER INFORMATION: Artificial Peptide

<400> SEQUENCE: 55

Gln Asn Gln Gln Glu Lys Asn Glu Gln Glu Leu Leu Glu Leu Asp Lys
1               5                   10                  15

Trp Ala Ser Leu Trp Asn Trp Phe
            20

<210> SEQ ID NO 56
<211> LENGTH: 25
<212> TYPE: PRT
<213> ORGANISM: Artificial Sequence
<220> FEATURE:
<223> OTHER INFORMATION: Artificial Peptide

<400> SEQUENCE: 56

Ser Gln Asn Gln Gln Glu Lys Asn Gln Glu Leu Leu Glu Leu Asp
1               5                   10                  15

Lys Trp Ala Ser Leu Trp Asn Trp Phe
            20                  25

<210> SEQ ID NO 57
<211> LENGTH: 26
<212> TYPE: PRT
<213> ORGANISM: Artificial Sequence
<220> FEATURE:
<223> OTHER INFORMATION: Artificial Peptide

<400> SEQUENCE: 57

Glu Ser Gln Asn Gln Gln Glu Lys Asn Gln Glu Leu Leu Glu Leu
1               5                   10                  15

Asp Lys Trp Ala Ser Leu Trp Asn Trp Phe
            20                  25

<210> SEQ ID NO 58
<211> LENGTH: 27
<212> TYPE: PRT
<213> ORGANISM: Artificial Sequence
<220> FEATURE:
<223> OTHER INFORMATION: Artificial Peptide

<400> SEQUENCE: 58

Glu Glu Ser Gln Asn Gln Gln Glu Lys Asn Gln Glu Leu Leu Glu
1               5                   10                  15

Leu Asp Lys Trp Ala Ser Leu Trp Asn Trp Phe
            20                  25

<210> SEQ ID NO 59
<211> LENGTH: 28
<212> TYPE: PRT
<213> ORGANISM: Artificial Sequence
<220> FEATURE:
<223> OTHER INFORMATION: Artificial Peptide

<400> SEQUENCE: 59

Ile Glu Glu Ser Gln Asn Gln Gln Glu Lys Asn Gln Glu Leu Leu
1               5                   10                  15

Glu Leu Asp Lys Trp Ala Ser Leu Trp Asn Trp Phe
            20                  25

<210> SEQ ID NO 60
<211> LENGTH: 29
<212> TYPE: PRT
<213> ORGANISM: Artificial Sequence
<220> FEATURE:
<223> OTHER INFORMATION: Artificial Peptide

<400> SEQUENCE: 60

Leu Ile Glu Glu Ser Gln Asn Gln Gln Glu Lys Asn Gln Glu Leu
1               5                   10                  15

Leu Glu Leu Asp Lys Trp Ala Ser Leu Trp Asn Trp Phe
            20                  25

<210> SEQ ID NO 61
<211> LENGTH: 30
<212> TYPE: PRT

```
<213> ORGANISM: Artificial Sequence
<220> FEATURE:
<223> OTHER INFORMATION: Artificial Peptide

<400> SEQUENCE: 61

Ser Leu Ile Glu Glu Ser Gln Asn Gln Gln Glu Lys Asn Glu Gln Glu
 1               5                  10                  15

Leu Leu Glu Leu Asp Lys Trp Ala Ser Leu Trp Asn Trp Phe
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: Artificial Peptide

<400> SEQUENCE: 62

His Ser Leu Ile Glu Glu Ser Gln Asn Gln Gln Glu Lys Asn Glu Gln
 1               5                  10                  15

Glu Leu Leu Glu Leu Asp Lys Trp Ala Ser Leu Trp Asn Trp Phe
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Artificial Peptide

<400> SEQUENCE: 63

Ile His Ser Leu Ile Glu Glu Ser Gln Asn Gln Gln Glu Lys Asn Glu
 1               5                  10                  15

Gln Glu Leu Leu Glu Leu Asp Lys Trp Ala Ser Leu Trp Asn Trp Phe
            20                  25                  30

<210> SEQ ID NO 64
<211> LENGTH: 33
<212> TYPE: PRT
<213> ORGANISM: Artificial Sequence
<220> FEATURE:
<223> OTHER INFORMATION: Artificial Peptide

<400> SEQUENCE: 64

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu Trp Asn Trp
            20                  25                  30

Phe

<210> SEQ ID NO 65
<211> LENGTH: 34
<212> TYPE: PRT
<213> ORGANISM: Artificial Sequence
<220> FEATURE:
<223> OTHER INFORMATION: Artificial Peptide

<400> SEQUENCE: 65

Ser Leu Ile His Ser Leu Ile Glu Glu Ser Gln Asn Gln Gln Glu Lys
 1               5                  10                  15

Asn Glu Gln Glu Leu Leu Glu Leu Asp Lys Trp Ala Ser Leu Trp Asn
            20                  25                  30

Trp Phe
```

<210> SEQ ID NO 66
<211> LENGTH: 35
<212> TYPE: PRT
<213> ORGANISM: Artificial Sequence
<220> FEATURE:
<223> OTHER INFORMATION: Artificial Peptide

<400> SEQUENCE: 66

Thr Ser Leu Ile His Ser Leu Ile Glu Glu Ser Gln Asn Gln Gln Glu
1               5                   10                  15

Lys Asn Glu Gln Glu Leu Leu Glu Leu Asp Lys Trp Ala Ser Leu Trp
            20                  25                  30

Asn Trp Phe
        35

<210> SEQ ID NO 67
<211> LENGTH: 36
<212> TYPE: PRT
<213> ORGANISM: Artificial Sequence
<220> FEATURE:
<223> OTHER INFORMATION: Artificial Peptide

<400> SEQUENCE: 67

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 68
<211> LENGTH: 32
<212> TYPE: PRT
<213> ORGANISM: Artificial Sequence
<220> FEATURE:
<223> OTHER INFORMATION: Artificial Peptide

<400> SEQUENCE: 68

Ile His Ser Leu Ile Glu Glu Ser Gln Asn Gln Gln Glu Lys Asn Glu
1               5                   10                  15

Gln Glu Leu Leu Glu Leu Asp Lys Trp Ala Ser Leu Trp Asn Trp Phe
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: Artificial Peptide

<400> SEQUENCE: 69

His Ser Leu Ile Glu Glu Ser Gln Asn Gln Gln Glu Lys Asn Glu Gln
1               5                   10                  15

Glu Leu Leu Glu Leu Asp Lys Trp Ala Ser Leu Trp Asn Trp Phe
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Artificial Peptide -continued

```
<400> SEQUENCE: 70

Ser Leu Ile Glu Glu Ser Gln Asn Gln Gln Glu Lys Asn Glu Gln Glu
 1               5                  10                  15

Leu Leu Glu Leu Asp Lys Trp Ala Ser Leu Trp Asn Trp Phe
            20                  25                  30

<210> SEQ ID NO 71
<211> LENGTH: 29
<212> TYPE: PRT
<213> ORGANISM: Artificial Sequence
<220> FEATURE:
<223> OTHER INFORMATION: Artificial Peptide

<400> SEQUENCE: 71

Leu Ile Glu Glu Ser Gln Asn Gln Gln Glu Lys Asn Glu Gln Glu Leu
 1               5                  10                  15

Leu Glu Leu Asp Lys Trp Ala Ser Leu Trp Asn Trp Phe
            20                  25

<210> SEQ ID NO 72
<211> LENGTH: 28
<212> TYPE: PRT
<213> ORGANISM: Artificial Sequence
<220> FEATURE:
<223> OTHER INFORMATION: Artificial Peptide

<400> SEQUENCE: 72

Ile Glu Glu Ser Gln Asn Gln Gln Glu Lys Asn Glu Gln Glu Leu Leu
 1               5                  10                  15

Glu Leu Asp Lys Trp Ala Ser Leu Trp Asn Trp Phe
            20                  25

<210> SEQ ID NO 73
<211> LENGTH: 27
<212> TYPE: PRT
<213> ORGANISM: Artificial Sequence
<220> FEATURE:
<223> OTHER INFORMATION: Artificial Peptide

<400> SEQUENCE: 73

Glu Glu Ser Gln Asn Gln Gln Glu Lys Asn Glu Gln Glu Leu Leu Glu
 1               5                  10                  15

Leu Asp Lys Trp Ala Ser Leu Trp Asn Trp Phe
            20                  25

<210> SEQ ID NO 74
<211> LENGTH: 26
<212> TYPE: PRT
<213> ORGANISM: Artificial Sequence
<220> FEATURE:
<223> OTHER INFORMATION: Artificial Peptide

<400> SEQUENCE: 74

Glu Ser Gln Asn Gln Gln Glu Lys Asn Glu Gln Glu Leu Leu Glu Leu
 1               5                  10                  15

Asp Lys Trp Ala Ser Leu Trp Asn Trp Phe
            20                  25

<210> SEQ ID NO 75
<211> LENGTH: 25
<212> TYPE: PRT
<213> ORGANISM: Artificial Sequence
<220> FEATURE:
<223> OTHER INFORMATION: Artificial Peptide
```

```
<400> SEQUENCE: 75

Ser Gln Asn Gln Gln Glu Lys Asn Glu Gln Glu Leu Leu Glu Leu Asp
 1               5                  10                  15

Lys Trp Ala Ser Leu Trp Asn Trp Phe
            20                  25

<210> SEQ ID NO 76
<211> LENGTH: 24
<212> TYPE: PRT
<213> ORGANISM: Artificial Sequence
<220> FEATURE:
<223> OTHER INFORMATION: Artificial Peptide

<400> SEQUENCE: 76

Gln Asn Gln Gln Glu Lys Asn Glu Gln Glu Leu Leu Glu Leu Asp Lys
 1               5                  10                  15

Trp Ala Ser Leu Trp Asn Trp Phe
            20

<210> SEQ ID NO 77
<211> LENGTH: 23
<212> TYPE: PRT
<213> ORGANISM: Artificial Sequence
<220> FEATURE:
<223> OTHER INFORMATION: Artificial Peptide

<400> SEQUENCE: 77

Asn Gln Gln Glu Lys Asn Glu Gln Glu Leu Leu Glu Leu Asp Lys Trp
 1               5                  10                  15

Ala Ser Leu Trp Asn Trp Phe
            20

<210> SEQ ID NO 78
<211> LENGTH: 22
<212> TYPE: PRT
<213> ORGANISM: Artificial Sequence
<220> FEATURE:
<223> OTHER INFORMATION: Artificial Peptide

<400> SEQUENCE: 78

Gln Gln Glu Lys Asn Glu Gln Glu Leu Leu Glu Leu Asp Lys Trp Ala
 1               5                  10                  15

Ser Leu Trp Asn Trp Phe
            20

<210> SEQ ID NO 79
<211> LENGTH: 21
<212> TYPE: PRT
<213> ORGANISM: Artificial Sequence
<220> FEATURE:
<223> OTHER INFORMATION: Artificial Peptide

<400> SEQUENCE: 79

Gln Glu Lys Asn Glu Gln Glu Leu Leu Glu Leu Asp Lys Trp Ala Ser
 1               5                  10                  15

Leu Trp Asn Trp Phe
            20

<210> SEQ ID NO 80
<211> LENGTH: 20
<212> TYPE: PRT
<213> ORGANISM: Artificial Sequence
<220> FEATURE:
```

-continued

<223> OTHER INFORMATION: Artificial Peptide

<400> SEQUENCE: 80

Glu Lys Asn Glu Gln Glu Leu Leu Glu Leu Asp Lys Trp Ala Ser Leu
1               5                   10                  15

Trp Asn Trp Phe
            20

<210> SEQ ID NO 81
<211> LENGTH: 19
<212> TYPE: PRT
<213> ORGANISM: Artificial Sequence
<220> FEATURE:
<223> OTHER INFORMATION: Artificial Peptide

<400> SEQUENCE: 81

Lys Asn Glu Gln Glu Leu Leu Glu Leu Asp Lys Trp Ala Ser Leu Trp
1               5                   10                  15

Asn Trp Phe

<210> SEQ ID NO 82
<211> LENGTH: 18
<212> TYPE: PRT
<213> ORGANISM: Artificial Sequence
<220> FEATURE:
<223> OTHER INFORMATION: Artificial Peptide

<400> SEQUENCE: 82

Asn Glu Gln Glu Leu Leu Glu Leu Asp Lys Trp Ala Ser Leu Trp Asn
1               5                   10                  15

Trp Phe

<210> SEQ ID NO 83
<211> LENGTH: 17
<212> TYPE: PRT
<213> ORGANISM: Artificial Sequence
<220> FEATURE:
<223> OTHER INFORMATION: Artificial Peptide

<400> SEQUENCE: 83

Glu Gln Glu Leu Leu Glu Leu Asp Lys Trp Ala Ser Leu Trp Asn Trp
1               5                   10                  15

Phe

<210> SEQ ID NO 84
<211> LENGTH: 16
<212> TYPE: PRT
<213> ORGANISM: Artificial Sequence
<220> FEATURE:
<223> OTHER INFORMATION: Artificial Peptide

<400> SEQUENCE: 84

Gln Glu Leu Leu Glu Leu Asp Lys Trp Ala Ser Leu Trp Asn Trp Phe
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Artificial Peptide

<400> SEQUENCE: 85

Glu Leu Leu Glu Leu Asp Lys Trp Ala Ser Leu Trp Asn Trp Phe

-continued

```
                1               5                  10                  15
```

<210> SEQ ID NO 86
<211> LENGTH: 14
<212> TYPE: PRT
<213> ORGANISM: Artificial Sequence
<220> FEATURE:
<223> OTHER INFORMATION: Artificial Peptide

<400> SEQUENCE: 86

```
Leu Leu Glu Leu Asp Lys Trp Ala Ser Leu Trp Asn Trp Phe
 1               5                  10
```

<210> SEQ ID NO 87
<211> LENGTH: 13
<212> TYPE: PRT
<213> ORGANISM: Artificial Sequence
<220> FEATURE:
<223> OTHER INFORMATION: Artificial Peptide

<400> SEQUENCE: 87

```
Leu Glu Leu Asp Lys Trp Ala Ser Leu Trp Asn Trp Phe
 1               5                  10
```

<210> SEQ ID NO 88
<211> LENGTH: 12
<212> TYPE: PRT
<213> ORGANISM: Artificial Sequence
<220> FEATURE:
<223> OTHER INFORMATION: Artificial Peptide

<400> SEQUENCE: 88

```
Glu Leu Asp Lys Trp Ala Ser Leu Trp Asn Trp Phe
 1               5                  10
```

<210> SEQ ID NO 89
<211> LENGTH: 11
<212> TYPE: PRT
<213> ORGANISM: Artificial Sequence
<220> FEATURE:
<223> OTHER INFORMATION: Artificial Peptide

<400> SEQUENCE: 89

```
Leu Asp Lys Trp Ala Ser Leu Trp Asn Trp Phe
 1               5                  10
```

<210> SEQ ID NO 90
<211> LENGTH: 10
<212> TYPE: PRT
<213> ORGANISM: Artificial Sequence
<220> FEATURE:
<223> OTHER INFORMATION: Artificial Peptide

<400> SEQUENCE: 90

```
Asp Lys Trp Ala Ser Leu Trp Asn Trp Phe
 1               5                  10
```

<210> SEQ ID NO 91
<211> LENGTH: 9
<212> TYPE: PRT
<213> ORGANISM: Artificial Sequence
<220> FEATURE:
<223> OTHER INFORMATION: Artificial Peptide

<400> SEQUENCE: 91

```
Lys Trp Ala Ser Leu Trp Asn Trp Phe
 1               5
```

```
<210> SEQ ID NO 92
<211> LENGTH: 8
<212> TYPE: PRT
<213> ORGANISM: Artificial Sequence
<220> FEATURE:
<223> OTHER INFORMATION: Artificial Peptide

<400> SEQUENCE: 92

Trp Ala Ser Leu Trp Asn Trp Phe
1               5

<210> SEQ ID NO 93
<211> LENGTH: 7
<212> TYPE: PRT
<213> ORGANISM: Artificial Sequence
<220> FEATURE:
<223> OTHER INFORMATION: Artificial Peptide

<400> SEQUENCE: 93

Ala Ser Leu Trp Asn Trp Phe
1               5

<210> SEQ ID NO 94
<211> LENGTH: 6
<212> TYPE: PRT
<213> ORGANISM: Artificial Sequence
<220> FEATURE:
<223> OTHER INFORMATION: Artificial Peptide

<400> SEQUENCE: 94

Ser Leu Trp Asn Trp Phe
1               5

<210> SEQ ID NO 95
<211> LENGTH: 5
<212> TYPE: PRT
<213> ORGANISM: Artificial Sequence
<220> FEATURE:
<223> OTHER INFORMATION: Artificial Peptide

<400> SEQUENCE: 95

Leu Trp Asn Trp Phe
1               5

<210> SEQ ID NO 96
<211> LENGTH: 4
<212> TYPE: PRT
<213> ORGANISM: Artificial Sequence
<220> FEATURE:
<223> OTHER INFORMATION: Artificial Peptide

<400> SEQUENCE: 96

Trp Asn Trp Phe
1

<210> SEQ ID NO 97
<211> LENGTH: 4
<212> TYPE: PRT
<213> ORGANISM: Artificial Sequence
<220> FEATURE:
<223> OTHER INFORMATION: Artificial Peptide

<400> SEQUENCE: 97

Asn Asn Leu Leu
1
```

```
<210> SEQ ID NO 98
<211> LENGTH: 5
<212> TYPE: PRT
<213> ORGANISM: Artificial Sequence
<220> FEATURE:
<223> OTHER INFORMATION: Artificial Peptide

<400> SEQUENCE: 98

Asn Asn Leu Leu Arg
 1               5

<210> SEQ ID NO 99
<211> LENGTH: 6
<212> TYPE: PRT
<213> ORGANISM: Artificial Sequence
<220> FEATURE:
<223> OTHER INFORMATION: Artificial Peptide

<400> SEQUENCE: 99

Asn Asn Leu Leu Arg Ala
 1               5

<210> SEQ ID NO 100
<211> LENGTH: 7
<212> TYPE: PRT
<213> ORGANISM: Artificial Sequence
<220> FEATURE:
<223> OTHER INFORMATION: Artificial Peptide

<400> SEQUENCE: 100

Asn Asn Leu Leu Arg Ala Ile
 1               5

<210> SEQ ID NO 101
<211> LENGTH: 8
<212> TYPE: PRT
<213> ORGANISM: Artificial Sequence
<220> FEATURE:
<223> OTHER INFORMATION: Artificial Peptide

<400> SEQUENCE: 101

Asn Asn Leu Leu Arg Ala Ile Glu
 1               5

<210> SEQ ID NO 102
<211> LENGTH: 9
<212> TYPE: PRT
<213> ORGANISM: Artificial Sequence
<220> FEATURE:
<223> OTHER INFORMATION: Artificial Peptide

<400> SEQUENCE: 102

Asn Asn Leu Leu Arg Ala Ile Glu Ala
 1               5

<210> SEQ ID NO 103
<211> LENGTH: 10
<212> TYPE: PRT
<213> ORGANISM: Artificial Sequence
<220> FEATURE:
<223> OTHER INFORMATION: Artificial Peptide

<400> SEQUENCE: 103

Asn Asn Leu Leu Arg Ala Ile Glu Ala Gln
 1               5                  10
```

```
<210> SEQ ID NO 104
<211> LENGTH: 11
<212> TYPE: PRT
<213> ORGANISM: Artificial Sequence
<220> FEATURE:
<223> OTHER INFORMATION: Artificial Peptide

<400> SEQUENCE: 104

Asn Asn Leu Leu Arg Ala Ile Glu Ala Gln Gln
 1               5                  10

<210> SEQ ID NO 105
<211> LENGTH: 12
<212> TYPE: PRT
<213> ORGANISM: Artificial Sequence
<220> FEATURE:
<223> OTHER INFORMATION: Artificial Peptide

<400> SEQUENCE: 105

Asn Asn Leu Leu Arg Ala Ile Glu Ala Gln Gln His
 1               5                  10

<210> SEQ ID NO 106
<211> LENGTH: 13
<212> TYPE: PRT
<213> ORGANISM: Artificial Sequence
<220> FEATURE:
<223> OTHER INFORMATION: Artificial Peptide

<400> SEQUENCE: 106

Asn Asn Leu Leu Arg Ala Ile Glu Ala Gln Gln His Leu
 1               5                  10

<210> SEQ ID NO 107
<211> LENGTH: 14
<212> TYPE: PRT
<213> ORGANISM: Artificial Sequence
<220> FEATURE:
<223> OTHER INFORMATION: Artificial Peptide

<400> SEQUENCE: 107

Asn Asn Leu Leu Arg Ala Ile Glu Ala Gln Gln His Leu Leu
 1               5                  10

<210> SEQ ID NO 108
<211> LENGTH: 15
<212> TYPE: PRT
<213> ORGANISM: Artificial Sequence
<220> FEATURE:
<223> OTHER INFORMATION: Artificial Peptide

<400> SEQUENCE: 108

Asn Asn Leu Leu Arg Ala Ile Glu Ala Gln Gln His Leu Leu Gln
 1               5                  10                  15

<210> SEQ ID NO 109
<211> LENGTH: 16
<212> TYPE: PRT
<213> ORGANISM: Artificial Sequence
<220> FEATURE:
<223> OTHER INFORMATION: Artificial Peptide

<400> SEQUENCE: 109

Asn Asn Leu Leu Arg Ala Ile Glu Ala Gln Gln His Leu Leu Gln Leu
 1               5                  10                  15

<210> SEQ ID NO 110
```

<211> LENGTH: 17
<212> TYPE: PRT
<213> ORGANISM: Artificial Sequence
<220> FEATURE:
<223> OTHER INFORMATION: Artificial Peptide

<400> SEQUENCE: 110

Asn Asn Leu Leu Arg Ala Ile Glu Ala Gln Gln His Leu Leu Gln Leu
1               5                   10                  15
Thr

<210> SEQ ID NO 111
<211> LENGTH: 18
<212> TYPE: PRT
<213> ORGANISM: Artificial Sequence
<220> FEATURE:
<223> OTHER INFORMATION: Artificial Peptide

<400> SEQUENCE: 111

Asn Asn Leu Leu Arg Ala Ile Glu Ala Gln Gln His Leu Leu Gln Leu
1               5                   10                  15
Thr Val

<210> SEQ ID NO 112
<211> LENGTH: 19
<212> TYPE: PRT
<213> ORGANISM: Artificial Sequence
<220> FEATURE:
<223> OTHER INFORMATION: Artificial Peptide

<400> SEQUENCE: 112

Asn Asn Leu Leu Arg Ala Ile Glu Ala Gln Gln His Leu Leu Gln Leu
1               5                   10                  15
Thr Val Trp

<210> SEQ ID NO 113
<211> LENGTH: 20
<212> TYPE: PRT
<213> ORGANISM: Artificial Sequence
<220> FEATURE:
<223> OTHER INFORMATION: Artificial Peptide

<400> SEQUENCE: 113

Asn Asn Leu Leu Arg Ala Ile Glu Ala Gln Gln His Leu Leu Gln Leu
1               5                   10                  15
Thr Val Trp Gly
            20

<210> SEQ ID NO 114
<211> LENGTH: 21
<212> TYPE: PRT
<213> ORGANISM: Artificial Sequence
<220> FEATURE:
<223> OTHER INFORMATION: Artificial Peptide

<400> SEQUENCE: 114

Asn Asn Leu Leu Arg Ala Ile Glu Ala Gln Gln His Leu Leu Gln Leu
1               5                   10                  15
Thr Val Trp Gly Ile
            20

<210> SEQ ID NO 115
<211> LENGTH: 22
<212> TYPE: PRT

<210> SEQ ID NO 115
<211> LENGTH: 21
<212> TYPE: PRT
<213> ORGANISM: Artificial Sequence
<220> FEATURE:
<223> OTHER INFORMATION: Artificial Peptide

<400> SEQUENCE: 115

Asn Asn Leu Leu Arg Ala Ile Glu Ala Gln Gln His Leu Leu Gln Leu
 1               5                  10                  15
Thr Val Trp Gly Ile Lys
            20

<210> SEQ ID NO 116
<211> LENGTH: 23
<212> TYPE: PRT
<213> ORGANISM: Artificial Sequence
<220> FEATURE:
<223> OTHER INFORMATION: Artificial Peptide

<400> SEQUENCE: 116

Asn Asn Leu Leu Arg Ala Ile Glu Ala Gln Gln His Leu Leu Gln Leu
 1               5                  10                  15
Thr Val Trp Gly Ile Lys Gln
            20

<210> SEQ ID NO 117
<211> LENGTH: 24
<212> TYPE: PRT
<213> ORGANISM: Artificial Sequence
<220> FEATURE:
<223> OTHER INFORMATION: Artificial Peptide

<400> SEQUENCE: 117

Asn Asn Leu Leu Arg Ala Ile Glu Ala Gln Gln His Leu Leu Gln Leu
 1               5                  10                  15
Thr Val Trp Gly Ile Lys Gln Leu
            20

<210> SEQ ID NO 118
<211> LENGTH: 24
<212> TYPE: PRT
<213> ORGANISM: Artificial Sequence
<220> FEATURE:
<223> OTHER INFORMATION: Artificial Peptide

<400> SEQUENCE: 118

Asn Asn Leu Leu Arg Ala Ile Glu Ala Gln Gln His Leu Leu Gln Leu
 1               5                  10                  15
Thr Val Trp Gly Ile Lys Gln Leu
            20

<210> SEQ ID NO 119
<211> LENGTH: 26
<212> TYPE: PRT
<213> ORGANISM: Artificial Sequence
<220> FEATURE:
<223> OTHER INFORMATION: Artificial Peptide

<400> SEQUENCE: 119

Asn Asn Leu Leu Arg Ala Ile Glu Ala Gln Gln His Leu Leu Gln Leu
 1               5                  10                  15
Thr Val Trp Gly Ile Lys Gln Leu Gln Ala
            20                  25

<210> SEQ ID NO 120
<211> LENGTH: 27

```
<212> TYPE: PRT
<213> ORGANISM: Artificial Sequence
<220> FEATURE:
<223> OTHER INFORMATION: Artificial Peptide

<400> SEQUENCE: 120

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg
            20                  25

<210> SEQ ID NO 121
<211> LENGTH: 28
<212> TYPE: PRT
<213> ORGANISM: Artificial Sequence
<220> FEATURE:
<223> OTHER INFORMATION: Artificial Peptide

<400> SEQUENCE: 121

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile
            20                  25

<210> SEQ ID NO 122
<211> LENGTH: 29
<212> TYPE: PRT
<213> ORGANISM: Artificial Sequence
<220> FEATURE:
<223> OTHER INFORMATION: Artificial Peptide

<400> SEQUENCE: 122

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu
            20                  25

<210> SEQ ID NO 123
<211> LENGTH: 30
<212> TYPE: PRT
<213> ORGANISM: Artificial Sequence
<220> FEATURE:
<223> OTHER INFORMATION: Artificial Peptide

<400> SEQUENCE: 123

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala
            20                  25                  30

<210> SEQ ID NO 124
<211> LENGTH: 31
<212> TYPE: PRT
<213> ORGANISM: Artificial Sequence
<220> FEATURE:
<223> OTHER INFORMATION: Artificial Peptide

<400> SEQUENCE: 124

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala Val
            20                  25                  30

<210> SEQ ID NO 125
```

<211> LENGTH: 32
<212> TYPE: PRT
<213> ORGANISM: Artificial Sequence
<220> FEATURE:
<223> OTHER INFORMATION: Artificial Peptide

<400> SEQUENCE: 125

Asn Asn Leu Leu Arg Ala Ile Glu Ala Gln Gln His Leu Leu Gln Leu
 1               5                  10                  15
Thr Val Trp Gly Ile Lys Gln Leu Gln Ala Arg Ile Leu Ala Val Glu
            20                  25                  30

<210> SEQ ID NO 126
<211> LENGTH: 33
<212> TYPE: PRT
<213> ORGANISM: Artificial Sequence
<220> FEATURE:
<223> OTHER INFORMATION: Artificial Peptide

<400> SEQUENCE: 126

Asn Asn Leu Leu Arg Ala Ile Glu Ala Gln Gln His Leu Leu Gln Leu
 1               5                  10                  15
Thr Val Trp Gly Ile Lys Gln Leu Gln Ala Arg Ile Leu Ala Val Glu
            20                  25                  30
Arg

<210> SEQ ID NO 127
<211> LENGTH: 34
<212> TYPE: PRT
<213> ORGANISM: Artificial Sequence
<220> FEATURE:
<223> OTHER INFORMATION: Artificial Peptide

<400> SEQUENCE: 127

Asn Asn Leu Leu Arg Ala Ile Glu Ala Gln Gln His Leu Leu Gln Leu
 1               5                  10                  15
Thr Val Trp Gly Ile Lys Gln Leu Gln Ala Arg Ile Leu Ala Val Glu
            20                  25                  30
Arg Tyr

<210> SEQ ID NO 128
<211> LENGTH: 35
<212> TYPE: PRT
<213> ORGANISM: Artificial Sequence
<220> FEATURE:
<223> OTHER INFORMATION: Artificial Peptide

<400> SEQUENCE: 128

Asn Asn Leu Leu Arg Ala Ile Glu Ala Gln Gln His Leu Leu Gln Leu
 1               5                  10                  15
Thr Val Trp Gly Ile Lys Gln Leu Gln Ala Arg Ile Leu Ala Val Glu
            20                  25                  30
Arg Tyr Leu
        35

<210> SEQ ID NO 129
<211> LENGTH: 36
<212> TYPE: PRT
<213> ORGANISM: Artificial Sequence
<220> FEATURE:
<223> OTHER INFORMATION: Artificial Peptide

<400> SEQUENCE: 129

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys
        35

<210> SEQ ID NO 130
<211> LENGTH: 37
<212> TYPE: PRT
<213> ORGANISM: Artificial Sequence
<220> FEATURE:
<223> OTHER INFORMATION: Artificial Peptide

<400> SEQUENCE: 130

Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp
        35

<210> SEQ ID NO 131
<211> LENGTH: 4
<212> TYPE: PRT
<213> ORGANISM: Artificial Sequence
<220> FEATURE:
<223> OTHER INFORMATION: Artificial Peptide

<400> SEQUENCE: 131

Leu Lys Asp Gln
1

<210> SEQ ID NO 132
<211> LENGTH: 4
<212> TYPE: PRT
<213> ORGANISM: Artificial Sequence
<220> FEATURE:
<223> OTHER INFORMATION: Artificial Peptide

<400> SEQUENCE: 132

Leu Lys Asp Gln
1

<210> SEQ ID NO 133
<211> LENGTH: 6
<212> TYPE: PRT
<213> ORGANISM: Artificial Sequence
<220> FEATURE:
<223> OTHER INFORMATION: Artificial Peptide

<400> SEQUENCE: 133

Arg Tyr Leu Lys Asp Gln
1               5

<210> SEQ ID NO 134
<211> LENGTH: 7
<212> TYPE: PRT
<213> ORGANISM: Artificial Sequence
<220> FEATURE:
<223> OTHER INFORMATION: Artificial Peptide

<400> SEQUENCE: 134

Glu Arg Tyr Leu Lys Asp Gln
1               5

```
<210> SEQ ID NO 135
<211> LENGTH: 8
<212> TYPE: PRT
<213> ORGANISM: Artificial Sequence
<220> FEATURE:
<223> OTHER INFORMATION: Artificial Peptide

<400> SEQUENCE: 135

Val Glu Arg Tyr Leu Lys Asp Gln
 1               5

<210> SEQ ID NO 136
<211> LENGTH: 9
<212> TYPE: PRT
<213> ORGANISM: Artificial Sequence
<220> FEATURE:
<223> OTHER INFORMATION: Artificial Peptide

<400> SEQUENCE: 136

Ala Val Glu Arg Tyr Leu Lys Asp Gln
 1               5

<210> SEQ ID NO 137
<211> LENGTH: 10
<212> TYPE: PRT
<213> ORGANISM: Artificial Sequence
<220> FEATURE:
<223> OTHER INFORMATION: Artificial Peptide

<400> SEQUENCE: 137

Leu Ala Val Glu Arg Tyr Leu Lys Asp Gln
 1               5                  10

<210> SEQ ID NO 138
<211> LENGTH: 11
<212> TYPE: PRT
<213> ORGANISM: Artificial Sequence
<220> FEATURE:
<223> OTHER INFORMATION: Artificial Peptide

<400> SEQUENCE: 138

Ile Leu Ala Val Glu Arg Tyr Leu Lys Asp Gln
 1               5                  10

<210> SEQ ID NO 139
<211> LENGTH: 12
<212> TYPE: PRT
<213> ORGANISM: Artificial Sequence
<220> FEATURE:
<223> OTHER INFORMATION: Artificial Peptide

<400> SEQUENCE: 139

Arg Ile Leu Ala Val Glu Arg Tyr Leu Lys Asp Gln
 1               5                  10

<210> SEQ ID NO 140
<211> LENGTH: 13
<212> TYPE: PRT
<213> ORGANISM: Artificial Sequence
<220> FEATURE:
<223> OTHER INFORMATION: Artificial Peptide

<400> SEQUENCE: 140

Ala Arg Ile Leu Ala Val Glu Arg Tyr Leu Lys Asp Gln
 1               5                  10
```

```
<210> SEQ ID NO 141
<211> LENGTH: 14
<212> TYPE: PRT
<213> ORGANISM: Artificial Sequence
<220> FEATURE:
<223> OTHER INFORMATION: Artificial Peptide

<400> SEQUENCE: 141

Gln Ala Arg Ile Leu Ala Val Glu Arg Tyr Leu Lys Asp Gln
 1               5                  10

<210> SEQ ID NO 142
<211> LENGTH: 15
<212> TYPE: PRT
<213> ORGANISM: Artificial Sequence
<220> FEATURE:
<223> OTHER INFORMATION: Artificial Peptide

<400> SEQUENCE: 142

Leu Gln Ala Arg Ile Leu Ala Val Glu Arg Tyr Leu Lys Asp Gln
 1               5                  10                  15

<210> SEQ ID NO 143
<211> LENGTH: 16
<212> TYPE: PRT
<213> ORGANISM: Artificial Sequence
<220> FEATURE:
<223> OTHER INFORMATION: Artificial Peptide

<400> SEQUENCE: 143

Gln Leu Gln Ala Arg Ile Leu Ala Val Glu Arg Tyr Leu Lys Asp Gln
 1               5                  10                  15

<210> SEQ ID NO 144
<211> LENGTH: 17
<212> TYPE: PRT
<213> ORGANISM: Artificial Sequence
<220> FEATURE:
<223> OTHER INFORMATION: Artificial Peptide

<400> SEQUENCE: 144

Lys Gln Leu Gln Ala Arg Ile Leu Ala Val Glu Arg Tyr Leu Lys Asp
 1               5                  10                  15

Gln

<210> SEQ ID NO 145
<211> LENGTH: 18
<212> TYPE: PRT
<213> ORGANISM: Artificial Sequence
<220> FEATURE:
<223> OTHER INFORMATION: Artificial Peptide

<400> SEQUENCE: 145

Ile Lys Gln Leu Gln Ala Arg Ile Leu Ala Val Glu Arg Tyr Leu Lys
 1               5                  10                  15

Asp Gln

<210> SEQ ID NO 146
<211> LENGTH: 19
<212> TYPE: PRT
<213> ORGANISM: Artificial Sequence
<220> FEATURE:
<223> OTHER INFORMATION: Artificial Peptide

<400> SEQUENCE: 146
```

Gly Ile Lys Gln Leu Gln Ala Arg Ile Leu Ala Val Glu Arg Tyr Leu
1               5                   10                  15

Lys Asp Gln

<210> SEQ ID NO 147
<211> LENGTH: 20
<212> TYPE: PRT
<213> ORGANISM: Artificial Sequence
<220> FEATURE:
<223> OTHER INFORMATION: Artificial Peptide

<400> SEQUENCE: 147

Trp Gly Ile Lys Gln Leu Gln Ala Arg Ile Leu Ala Val Glu Arg Tyr
1               5                   10                  15

Leu Lys Asp Gln
            20

<210> SEQ ID NO 148
<211> LENGTH: 21
<212> TYPE: PRT
<213> ORGANISM: Artificial Sequence
<220> FEATURE:
<223> OTHER INFORMATION: Artificial Peptide

<400> SEQUENCE: 148

Val Trp Gly Ile Lys Gln Leu Gln Ala Arg Ile Leu Ala Val Glu Arg
1               5                   10                  15

Tyr Leu Lys Asp Gln
            20

<210> SEQ ID NO 149
<211> LENGTH: 22
<212> TYPE: PRT
<213> ORGANISM: Artificial Sequence
<220> FEATURE:
<223> OTHER INFORMATION: Artificial Peptide

<400> SEQUENCE: 149

Thr Val Trp Gly Ile Lys Gln Leu Gln Ala Arg Ile Leu Ala Val Glu
1               5                   10                  15

Arg Tyr Leu Lys Asp Gln
            20

<210> SEQ ID NO 150
<211> LENGTH: 23
<212> TYPE: PRT
<213> ORGANISM: Artificial Sequence
<220> FEATURE:
<223> OTHER INFORMATION: Artificial Peptide

<400> SEQUENCE: 150

Leu Thr Val Trp Gly Ile Lys Gln Leu Gln Ala Arg Ile Leu Ala Val
1               5                   10                  15

Glu Arg Tyr Leu Lys Asp Gln
            20

<210> SEQ ID NO 151
<211> LENGTH: 24
<212> TYPE: PRT
<213> ORGANISM: Artificial Sequence
<220> FEATURE:
<223> OTHER INFORMATION: Artificial Peptide

<400> SEQUENCE: 151

Gln Leu Thr Val Trp Gly Ile Lys Gln Leu Gln Ala Arg Ile Leu Ala
1               5                   10                  15

Val Glu Arg Tyr Leu Lys Asp Gln
            20

<210> SEQ ID NO 152
<211> LENGTH: 25
<212> TYPE: PRT
<213> ORGANISM: Artificial Sequence
<220> FEATURE:
<223> OTHER INFORMATION: Artificial Peptide

<400> SEQUENCE: 152

Leu Gln Leu Thr Val Trp Gly Ile Lys Gln Leu Gln Ala Arg Ile Leu
1               5                   10                  15

Ala Val Glu Arg Tyr Leu Lys Asp Gln
            20                  25

<210> SEQ ID NO 153
<211> LENGTH: 26
<212> TYPE: PRT
<213> ORGANISM: Artificial Sequence
<220> FEATURE:
<223> OTHER INFORMATION: Artificial Peptide

<400> SEQUENCE: 153

Leu Leu Gln Leu Thr Val Trp Gly Ile Lys Gln Leu Gln Ala Arg Ile
1               5                   10                  15

Leu Ala Val Glu Arg Tyr Leu Lys Asp Gln
            20                  25

<210> SEQ ID NO 154
<211> LENGTH: 27
<212> TYPE: PRT
<213> ORGANISM: Artificial Sequence
<220> FEATURE:
<223> OTHER INFORMATION: Artificial Peptide

<400> SEQUENCE: 154

His Leu Leu Gln Leu Thr Val Trp Gly Ile Lys Gln Leu Gln Ala Arg
1               5                   10                  15

Ile Leu Ala Val Glu Arg Tyr Leu Lys Asp Gln
            20                  25

<210> SEQ ID NO 155
<211> LENGTH: 28
<212> TYPE: PRT
<213> ORGANISM: Artificial Sequence
<220> FEATURE:
<223> OTHER INFORMATION: Artificial Peptide

<400> SEQUENCE: 155

Gln His Leu Leu Gln Leu Thr Val Trp Gly Ile Lys Gln Leu Gln Ala
1               5                   10                  15

Arg Ile Leu Ala Val Glu Arg Tyr Leu Lys Asp Gln
            20                  25

<210> SEQ ID NO 156
<211> LENGTH: 29
<212> TYPE: PRT
<213> ORGANISM: Artificial Sequence
<220> FEATURE:
<223> OTHER INFORMATION: Artificial Peptide

<400> SEQUENCE: 156

```
Gln Gln His Leu Leu Gln Leu Thr Val Trp Gly Ile Lys Gln Leu Gln
  1               5                  10                  15

Ala Arg Ile Leu Ala Val Glu Arg Tyr Leu Lys Asp Gln
             20                  25
```

<210> SEQ ID NO 157
<211> LENGTH: 30
<212> TYPE: PRT
<213> ORGANISM: Artificial Sequence
<220> FEATURE:
<223> OTHER INFORMATION: Artificial Peptide

<400> SEQUENCE: 157

```
Ala Gln Gln His Leu Leu Gln Leu Thr Val Trp Gly Ile Lys Gln Leu
  1               5                  10                  15

Gln Ala Arg Ile Leu Ala Val Glu Arg Tyr Leu Lys Asp Gln
             20                  25                  30
```

<210> SEQ ID NO 158
<211> LENGTH: 31
<212> TYPE: PRT
<213> ORGANISM: Artificial Sequence
<220> FEATURE:
<223> OTHER INFORMATION: Artificial Peptide

<400> SEQUENCE: 158

```
Glu Ala Gln Gln His Leu Leu Gln Leu Thr Val Trp Gly Ile Lys Gln
  1               5                  10                  15

Leu Gln Ala Arg Ile Leu Ala Val Glu Arg Tyr Leu Lys Asp Gln
             20                  25                  30
```

<210> SEQ ID NO 159
<211> LENGTH: 32
<212> TYPE: PRT
<213> ORGANISM: Artificial Sequence
<220> FEATURE:
<223> OTHER INFORMATION: Artificial Peptide

<400> SEQUENCE: 159

```
Ile Glu Ala Gln Gln His Leu Leu Gln Leu Thr Val Trp Gly Ile Lys
  1               5                  10                  15

Gln Leu Gln Ala Arg Ile Leu Ala Val Glu Arg Tyr Leu Lys Asp Gln
             20                  25                  30
```

<210> SEQ ID NO 160
<211> LENGTH: 33
<212> TYPE: PRT
<213> ORGANISM: Artificial Sequence
<220> FEATURE:
<223> OTHER INFORMATION: Artificial Peptide

<400> SEQUENCE: 160

```
Ala Ile Glu Ala Gln Gln His Leu Leu Gln Leu Thr Val Trp Gly Ile
  1               5                  10                  15

Lys Gln Leu Gln Ala Arg Ile Leu Ala Val Glu Arg Tyr Leu Lys Asp
             20                  25                  30

Gln
```

<210> SEQ ID NO 161
<211> LENGTH: 34
<212> TYPE: PRT
<213> ORGANISM: Artificial Sequence
<220> FEATURE:

<223> OTHER INFORMATION: Artificial Peptide

<400> SEQUENCE: 161

Arg Ala Ile Glu Ala Gln Gln His Leu Leu Gln Leu Thr Val Trp Gly
1               5                   10                  15

Ile Lys Gln Leu Gln Ala Arg Ile Leu Ala Val Glu Arg Tyr Leu Lys
            20                  25                  30

Asp Gln

<210> SEQ ID NO 162
<211> LENGTH: 35
<212> TYPE: PRT
<213> ORGANISM: Artificial Sequence
<220> FEATURE:
<223> OTHER INFORMATION: Artificial Peptide

<400> SEQUENCE: 162

Leu Arg Ala Ile Glu Ala Gln Gln His Leu Leu Gln Leu Thr Val Trp
1               5                   10                  15

Gly Ile Lys Gln Leu Gln Ala Arg Ile Leu Ala Val Glu Arg Tyr Leu
            20                  25                  30

Lys Asp Gln
        35

<210> SEQ ID NO 163
<211> LENGTH: 36
<212> TYPE: PRT
<213> ORGANISM: Artificial Sequence
<220> FEATURE:
<223> OTHER INFORMATION: Artificial Peptide

<400> SEQUENCE: 163

Leu Leu Arg Ala Ile Glu Ala Gln Gln His Leu Leu Gln Leu Thr Val
1               5                   10                  15

Trp Gly Ile Lys Gln Leu Gln Ala Arg Ile Leu Ala Val Glu Arg Tyr
            20                  25                  30

Leu Lys Asp Gln
        35

<210> SEQ ID NO 164
<211> LENGTH: 37
<212> TYPE: PRT
<213> ORGANISM: Artificial Sequence
<220> FEATURE:
<223> OTHER INFORMATION: Artificial Peptide

<400> SEQUENCE: 164

Asn Leu Leu Arg Ala Ile Glu Ala Gln Gln His Leu Leu Gln Leu Thr
1               5                   10                  15

Val Trp Gly Ile Lys Gln Leu Gln Ala Arg Ile Leu Ala Val Glu Arg
            20                  25                  30

Tyr Leu Lys Asp Gln
        35

<210> SEQ ID NO 165
<211> LENGTH: 38
<212> TYPE: PRT
<213> ORGANISM: Artificial Sequence
<220> FEATURE:
<223> OTHER INFORMATION: Artificial Peptide

<400> SEQUENCE: 165

```
Asn Asn Leu Leu Arg Ala Ile Glu Ala Gln Gln His Leu Leu Gln Leu
1               5                   10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 166
<211> LENGTH: 34
<212> TYPE: PRT
<213> ORGANISM: Artificial Sequence
<220> FEATURE:
<223> OTHER INFORMATION: Artificial Peptide

<400> SEQUENCE: 166

Arg Ala Ile Glu Ala Gln Gln His Leu Leu Gln Leu Thr Val Trp Gly
1               5                   10                  15

Ile Lys Gln Leu Gln Ala Arg Ile Leu Ala Val Glu Arg Tyr Leu Lys
            20                  25                  30

Asp Gln

<210> SEQ ID NO 167
<211> LENGTH: 33
<212> TYPE: PRT
<213> ORGANISM: Artificial Sequence
<220> FEATURE:
<223> OTHER INFORMATION: Artificial Peptide

<400> SEQUENCE: 167

Ala Ile Glu Ala Gln Gln His Leu Leu Gln Leu Thr Val Trp Gly Ile
1               5                   10                  15

Lys Gln Leu Gln Ala Arg Ile Leu Ala Val Glu Arg Tyr Leu Lys Asp
            20                  25                  30

Gln

<210> SEQ ID NO 168
<211> LENGTH: 32
<212> TYPE: PRT
<213> ORGANISM: Artificial Sequence
<220> FEATURE:
<223> OTHER INFORMATION: Artificial Peptide

<400> SEQUENCE: 168

Ile Glu Ala Gln Gln His Leu Leu Gln Leu Thr Val Trp Gly Ile Lys
1               5                   10                  15

Gln Leu Gln Ala Arg Ile Leu Ala Val Glu Arg Tyr Leu Lys Asp Gln
            20                  25                  30

<210> SEQ ID NO 169
<211> LENGTH: 31
<212> TYPE: PRT
<213> ORGANISM: Artificial Sequence
<220> FEATURE:
<223> OTHER INFORMATION: Artificial Peptide

<400> SEQUENCE: 169

Glu Ala Gln Gln His Leu Leu Gln Leu Thr Val Trp Gly Ile Lys Gln
1               5                   10                  15

Leu Gln Ala Arg Ile Leu Ala Val Glu Arg Tyr Leu Lys Asp Gln
            20                  25                  30

<210> SEQ ID NO 170
```

```
<211> LENGTH: 30
<212> TYPE: PRT
<213> ORGANISM: Artificial Sequence
<220> FEATURE:
<223> OTHER INFORMATION: Artificial Peptide

<400> SEQUENCE: 170

Ala Gln Gln His Leu Leu Gln Leu Thr Val Trp Gly Ile Lys Gln Leu
 1               5                  10                  15

Gln Ala Arg Ile Leu Ala Val Glu Arg Tyr Leu Lys Asp Gln
             20                  25                  30

<210> SEQ ID NO 171
<211> LENGTH: 29
<212> TYPE: PRT
<213> ORGANISM: Artificial Sequence
<220> FEATURE:
<223> OTHER INFORMATION: Artificial Peptide

<400> SEQUENCE: 171

Gln Gln His Leu Leu Gln Leu Thr Val Trp Gly Ile Lys Gln Leu Gln
 1               5                  10                  15

Ala Arg Ile Leu Ala Val Glu Arg Tyr Leu Lys Asp Gln
             20                  25

<210> SEQ ID NO 172
<211> LENGTH: 28
<212> TYPE: PRT
<213> ORGANISM: Artificial Sequence
<220> FEATURE:
<223> OTHER INFORMATION: Artificial Peptide

<400> SEQUENCE: 172

Gln His Leu Leu Gln Leu Thr Val Trp Gly Ile Lys Gln Leu Gln Ala
 1               5                  10                  15

Arg Ile Leu Ala Val Glu Arg Tyr Leu Lys Asp Gln
             20                  25

<210> SEQ ID NO 173
<211> LENGTH: 27
<212> TYPE: PRT
<213> ORGANISM: Artificial Sequence
<220> FEATURE:
<223> OTHER INFORMATION: Artificial Peptide

<400> SEQUENCE: 173

His Leu Leu Gln Leu Thr Val Trp Gly Ile Lys Gln Leu Gln Ala Arg
 1               5                  10                  15

Ile Leu Ala Val Glu Arg Tyr Leu Lys Asp Gln
             20                  25

<210> SEQ ID NO 174
<211> LENGTH: 26
<212> TYPE: PRT
<213> ORGANISM: Artificial Sequence
<220> FEATURE:
<223> OTHER INFORMATION: Artificial Peptide

<400> SEQUENCE: 174

Leu Leu Gln Leu Thr Val Trp Gly Ile Lys Gln Leu Gln Ala Arg Ile
 1               5                  10                  15

Leu Ala Val Glu Arg Tyr Leu Lys Asp Gln
             20                  25
```

<210> SEQ ID NO 175
<211> LENGTH: 25
<212> TYPE: PRT
<213> ORGANISM: Artificial Sequence
<220> FEATURE:
<223> OTHER INFORMATION: Artificial Peptide

<400> SEQUENCE: 175

Leu Gln Leu Thr Val Trp Gly Ile Lys Gln Leu Gln Ala Arg Ile Leu
 1               5                  10                  15

Ala Val Glu Arg Tyr Leu Lys Asp Gln
            20                  25

<210> SEQ ID NO 176
<211> LENGTH: 24
<212> TYPE: PRT
<213> ORGANISM: Artificial Sequence
<220> FEATURE:
<223> OTHER INFORMATION: Artificial Peptide

<400> SEQUENCE: 176

Gln Leu Thr Val Trp Gly Ile Lys Gln Leu Gln Ala Arg Ile Leu Ala
 1               5                  10                  15

Val Glu Arg Tyr Leu Lys Asp Gln
            20

<210> SEQ ID NO 177
<211> LENGTH: 23
<212> TYPE: PRT
<213> ORGANISM: Artificial Sequence
<220> FEATURE:
<223> OTHER INFORMATION: Artificial Peptide

<400> SEQUENCE: 177

Leu Thr Val Trp Gly Ile Lys Gln Leu Gln Ala Arg Ile Leu Ala Val
 1               5                  10                  15

Glu Arg Tyr Leu Lys Asp Gln
            20

<210> SEQ ID NO 178
<211> LENGTH: 22
<212> TYPE: PRT
<213> ORGANISM: Artificial Sequence
<220> FEATURE:
<223> OTHER INFORMATION: Artificial Peptide

<400> SEQUENCE: 178

Thr Val Trp Gly Ile Lys Gln Leu Gln Ala Arg Ile Leu Ala Val Glu
 1               5                  10                  15

Arg Tyr Leu Lys Asp Gln
            20

<210> SEQ ID NO 179
<211> LENGTH: 21
<212> TYPE: PRT
<213> ORGANISM: Artificial Sequence
<220> FEATURE:
<223> OTHER INFORMATION: Artificial Peptide

<400> SEQUENCE: 179

Val Trp Gly Ile Lys Gln Leu Gln Ala Arg Ile Leu Ala Val Glu Arg
 1               5                  10                  15

Tyr Leu Lys Asp Gln
            20

```
<210> SEQ ID NO 180
<211> LENGTH: 20
<212> TYPE: PRT
<213> ORGANISM: Artificial Sequence
<220> FEATURE:
<223> OTHER INFORMATION: Artificial Peptide

<400> SEQUENCE: 180

Trp Gly Ile Lys Gln Leu Gln Ala Arg Ile Leu Ala Val Glu Arg Tyr
 1               5                  10                  15
Leu Lys Asp Gln
         20

<210> SEQ ID NO 181
<211> LENGTH: 19
<212> TYPE: PRT
<213> ORGANISM: Artificial Sequence
<220> FEATURE:
<223> OTHER INFORMATION: Artificial Peptide

<400> SEQUENCE: 181

Gly Ile Lys Gln Leu Gln Ala Arg Ile Leu Ala Val Glu Arg Tyr Leu
 1               5                  10                  15
Lys Asp Gln

<210> SEQ ID NO 182
<211> LENGTH: 18
<212> TYPE: PRT
<213> ORGANISM: Artificial Sequence
<220> FEATURE:
<223> OTHER INFORMATION: Artificial Peptide

<400> SEQUENCE: 182

Ile Lys Gln Leu Gln Ala Arg Ile Leu Ala Val Glu Arg Tyr Leu Lys
 1               5                  10                  15
Asp Gln

<210> SEQ ID NO 183
<211> LENGTH: 17
<212> TYPE: PRT
<213> ORGANISM: Artificial Sequence
<220> FEATURE:
<223> OTHER INFORMATION: Artificial Peptide

<400> SEQUENCE: 183

Lys Gln Leu Gln Ala Arg Ile Leu Ala Val Glu Arg Tyr Leu Lys Asp
 1               5                  10                  15
Gln

<210> SEQ ID NO 184
<211> LENGTH: 16
<212> TYPE: PRT
<213> ORGANISM: Artificial Sequence
<220> FEATURE:
<223> OTHER INFORMATION: Artificial Peptide

<400> SEQUENCE: 184

Gln Leu Gln Ala Arg Ile Leu Ala Val Glu Arg Tyr Leu Lys Asp Gln
 1               5                  10                  15

<210> SEQ ID NO 185
<211> LENGTH: 15
<212> TYPE: PRT
<213> ORGANISM: Artificial Sequence
```

```
<220> FEATURE:
<223> OTHER INFORMATION: Artificial Peptide

<400> SEQUENCE: 185

Leu Gln Ala Arg Ile Leu Ala Val Glu Arg Tyr Leu Lys Asp Gln
 1               5                  10                  15

<210> SEQ ID NO 186
<211> LENGTH: 14
<212> TYPE: PRT
<213> ORGANISM: Artificial Sequence
<220> FEATURE:
<223> OTHER INFORMATION: Artificial Peptide

<400> SEQUENCE: 186

Gln Ala Arg Ile Leu Ala Val Glu Arg Tyr Leu Lys Asp Gln
 1               5                  10

<210> SEQ ID NO 187
<211> LENGTH: 13
<212> TYPE: PRT
<213> ORGANISM: Artificial Sequence
<220> FEATURE:
<223> OTHER INFORMATION: Artificial Peptide

<400> SEQUENCE: 187

Ala Arg Ile Leu Ala Val Glu Arg Tyr Leu Lys Asp Gln
 1               5                  10

<210> SEQ ID NO 188
<211> LENGTH: 13
<212> TYPE: PRT
<213> ORGANISM: Artificial Sequence
<220> FEATURE:
<223> OTHER INFORMATION: Artificial Peptide

<400> SEQUENCE: 188

Ala Arg Ile Leu Ala Val Glu Arg Tyr Leu Lys Asp Gln
 1               5                  10

<210> SEQ ID NO 189
<211> LENGTH: 12
<212> TYPE: PRT
<213> ORGANISM: Artificial Sequence
<220> FEATURE:
<223> OTHER INFORMATION: Artificial Peptide

<400> SEQUENCE: 189

Arg Ile Leu Ala Val Glu Arg Tyr Leu Lys Asp Gln
 1               5                  10

<210> SEQ ID NO 190
<211> LENGTH: 10
<212> TYPE: PRT
<213> ORGANISM: Artificial Sequence
<220> FEATURE:
<223> OTHER INFORMATION: Artificial Peptide

<400> SEQUENCE: 190

Leu Ala Val Glu Arg Tyr Leu Lys Asp Gln
 1               5                  10

<210> SEQ ID NO 191
<211> LENGTH: 9
<212> TYPE: PRT
<213> ORGANISM: Artificial Sequence
<220> FEATURE:
```

<223> OTHER INFORMATION: Artificial Peptide

<400> SEQUENCE: 191

Ala Val Glu Arg Tyr Leu Lys Asp Gln
 1               5

<210> SEQ ID NO 192
<211> LENGTH: 8
<212> TYPE: PRT
<213> ORGANISM: Artificial Sequence
<220> FEATURE:
<223> OTHER INFORMATION: Artificial Peptide

<400> SEQUENCE: 192

Val Glu Arg Tyr Leu Lys Asp Gln
 1               5

<210> SEQ ID NO 193
<211> LENGTH: 7
<212> TYPE: PRT
<213> ORGANISM: Artificial Sequence
<220> FEATURE:
<223> OTHER INFORMATION: Artificial Peptide

<400> SEQUENCE: 193

Glu Arg Tyr Leu Lys Asp Gln
 1               5

<210> SEQ ID NO 194
<211> LENGTH: 6
<212> TYPE: PRT
<213> ORGANISM: Artificial Sequence
<220> FEATURE:
<223> OTHER INFORMATION: Artificial Peptide

<400> SEQUENCE: 194

Arg Tyr Leu Lys Asp Gln
 1               5

<210> SEQ ID NO 195
<211> LENGTH: 5
<212> TYPE: PRT
<213> ORGANISM: Artificial Sequence
<220> FEATURE:
<223> OTHER INFORMATION: Artificial Peptide

<400> SEQUENCE: 195

Tyr Leu Lys Asp Gln
 1               5

<210> SEQ ID NO 196
<211> LENGTH: 4
<212> TYPE: PRT
<213> ORGANISM: Artificial Sequence
<220> FEATURE:
<223> OTHER INFORMATION: Artificial Peptide

<400> SEQUENCE: 196

Leu Lys Asp Gln
 1

<210> SEQ ID NO 197
<211> LENGTH: 36
<212> TYPE: PRT
<213> ORGANISM: Artificial Sequence
<220> FEATURE:
<223> OTHER INFORMATION: Artificial Peptide -continued

<400> SEQUENCE: 197

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 198
<211> LENGTH: 33
<212> TYPE: PRT
<213> ORGANISM: Artificial Sequence
<220> FEATURE:
<223> OTHER INFORMATION: Artificial Peptide

<400> SEQUENCE: 198

Leu Ile His Ser Leu Ile Glu Glu Ser Gln Asn Gln Gln Glu Lys Asn
1               5                   10                  15

Glu Gln Glu Leu Leu Glu Leu Asp Lys Trp Ala Ser Leu Trp Asn Trp
            20                  25                  30

Phe

<210> SEQ ID NO 199
<211> LENGTH: 31
<212> TYPE: PRT
<213> ORGANISM: Artificial Sequence
<220> FEATURE:
<223> OTHER INFORMATION: Artificial Peptide

<400> SEQUENCE: 199

His Ser Leu Ile Glu Glu Ser Gln Asn Gln Gln Glu Lys Asn Glu Gln
1               5                   10                  15

Glu Leu Leu Glu Leu Asp Lys Trp Ala Ser Leu Trp Asn Trp Phe
            20                  25                  30

<210> SEQ ID NO 200
<211> LENGTH: 29
<212> TYPE: PRT
<213> ORGANISM: Artificial Sequence
<220> FEATURE:
<223> OTHER INFORMATION: Artificial Peptide

<400> SEQUENCE: 200

Leu Ile Glu Glu Ser Gln Asn Gln Gln Glu Lys Asn Glu Gln Glu Leu
1               5                   10                  15

Leu Glu Leu Asp Lys Trp Ala Ser Leu Trp Asn Trp Phe
            20                  25

<210> SEQ ID NO 201
<211> LENGTH: 24
<212> TYPE: PRT
<213> ORGANISM: Artificial Sequence
<220> FEATURE:
<223> OTHER INFORMATION: Artificial Peptide

<400> SEQUENCE: 201

Gln Asn Gln Gln Glu Lys Asn Glu Gln Glu Leu Leu Glu Leu Asp Lys
1               5                   10                  15

Trp Ala Ser Leu Trp Asn Trp Phe
            20

```
<210> SEQ ID NO 202
<211> LENGTH: 38
<212> TYPE: PRT
<213> ORGANISM: Artificial Sequence
<220> FEATURE:
<223> OTHER INFORMATION: Artificial Peptide

<400> SEQUENCE: 202

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala Val Glu
            20                  25                  30

Arg Tyr Leu Lys Asp Gln
        35

<210> SEQ ID NO 203
<211> LENGTH: 38
<212> TYPE: PRT
<213> ORGANISM: Artificial Sequence
<220> FEATURE:
<223> OTHER INFORMATION: Artificial Peptide

<400> SEQUENCE: 203

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala Val Glu
            20                  25                  30

Arg Tyr Leu Lys Asp Gln
        35
```

T20/DP178 IS AN ACTIVATOR OF HUMAN PHAGOCYTE FORMYL PEPTIDE RECEPTORS

CROSS-REFERENCE TO RELATED APPLICATIONS

This application is a continuation of international application number PCT/US00/12371, and claims the benefit of priority of international application number PCT/US00/12371 having international filing date of May 5, 2000, designating the United States of America and published in English, which claims the benefit of priority of U.S. provisional patent application No. 60/132,686, filed May 5, 1999; both of which are hereby expressly incorporated by reference in their entireties.

FIELD OF THE INVENTION

The present invention relates to the discovery that T20/DP178, T21/DP107, and fragments thereof interact with members of the formyl peptide receptor family and thereby modulate cell migration and activation. Novel biological tools, prophylactics, therapeutics and methods of use of the foregoing for modulating an inflammatory response are disclosed.

BACKGROUND OF THE INVENTION

The envelope proteins of human immunodeficiency virus type 1 (HIV-1) are synthesized in the form of a precursor, gp160, which is subsequently cleaved by proteinases to yield mature proteins gp120 and gp41. (Kowalski et al., *Science* 237: 1351 (1987)). Gp120 is noncovalently bound to the extracellular domain of gp41 and mediates viral binding to host cells through high affinity interaction with CD4 receptors, followed by interaction with chemokine receptors which have recently been identified as HIV-1 fusion co-factors. (Dimitrov and Broder, *HIV and Membrane Receptors, HIV and membrane fusion*. Medical Intelligence Unit, Landes Bioscience, Austin, Tex. (1997); and Berger, *AIDS* 11, Suppl A: S3 (1997)). The viral envelope gp41 plays a critical role in fusion of HIV-1 and host cell membranes. (Dimitrov and Broder, *HIV and Membrane Receptors, HIV and membrane fusion*. Medical Intelligence Unit, Landes Bioscience, Austin, Tex. (1997); and Berger, *AIDS* 11, Suppl A: S3 (1997)).

Structural analysis predicts the gp41 ectodomain to contain two segments as extended helices. (Chan et al., *Cell* 89: 263 (1997)). One segment, termed T21/DP107 in the $NH_2$-terminus has a leucine zipper like motif, whereas another segment T20/DP178 is located in the carboxyl terminus of the gp41 ectodomain. In the absence of gp120 and the N-terminal fusion domain, the ectodomain of gp41 forms a soluble α-helical rodlike oligomer. (Chan et al., *Cell* 89: 263 (1997) and Lawless et al., *Biochemistry* 35: 13697 (1996)). The peptide segment T20/DP178, located in the C-terminus of the ectodomain of gp41, interacts with the N-terminal leucine zipper-like domain on gp41 to establish the fusogenic conformation of the virus. Synthetic analogues of both T21/DP107 and T20/DP178 have been shown to inhibit virus-mediated cell-cell fusion and to reduce the infectious titer of cell-free virus. (Lawless et al., *Biochemistry* 35: 13697 (1996); Lawless et al., *Biochemistry* 35: 13697 (1996); Kazmierski et al., *J. Med. Chem.* 39: 2681 (1996); Chen et al., *J. Virol.* 69: 3771 (1995); Sabatier et al., *Virology* 223: 406 (1996); Kliger et al., *J. Biol. Chem.* 272: 13496 (1997); and Munoz-Barroso et al., *J. Cell. Biol.* 140: 315 (1998)). Although T21/DP107 and T20/DP178 peptides have been shown to inhibit HIV-1-fusion, other biological and biochemical interactions involving these peptides or fragments thereof have not been identified.

BRIEF SUMMARY OF THE INVENTION

Patients suffering with AIDS have monocytes which exhibit a reduced migratory response when stimulated with a variety of chemoattractants in vitro. (Smith et al., *J. Clin. Invest.* 74: 2121 (1984)). Exposure of human monocytes to either HIV-1 envelope proteins gp120 or gp41, inhibits their chemotactic responses to a wide variety of chemoattractants including the bacterial chemotactic peptide N-formyl-methionyl-leucyl-phenylalanine (fMLP) and a number of recently defined chemokines through a mechanism resembling heterologous "desensitization". (Wang et al., *J. Immunol.* 161: 4309 (1998); and Ueda et al., *J. Clin. Invest.* 102: 804 (1998)). In order to further define the structural basis for the capacity of HIV-1 envelope proteins to "desensitize" host cells, we have evaluated the effects of selected peptide segments of gp41 on human immune cells.

In the disclosure that follows, we report our discovery that T20/DP178 and T21/DP107 interact with members of the formyl peptide receptor family (collectively referred to as "FPR class" or "FPR members") and thereby up-regulate an inflammatory response. The FPR class includes members such as the N-formyl peptide receptor (FPR) and the N-formyl peptide receptor-like 1 (FPRL1) molecules and more family members may be identified in the future, for example, by comparing regions of homology which are readily identified in the sequence of FPR and FPRL1. By interacting with an FPR member, T20/DP178 and T21/DP107 act as both potent chemoattractants and activators of human peripheral blood phagocytes (monocytes and neutrophils) but not T lymphocytes. Our discovery that T20/DP178 and T21/DP107 induce cell migration and calcium mobilization in cells by interacting with an FPR member is based on several experiments using cells transfected to express these proteins. In the experiments and discussion presented below, we demonstrate that the T20/DP178- and T21/DP107-induced activation of phagocytes is pertussis toxin sensitive and that fMLP does not induce significant chemotaxis of FPRL1 expressing cells at concentrations as high as 50 μM. Further, we show that a lipid metabolite, lipoxin A4 (a high affinity ligand for FPRL1), is not able to induce $Ca^{++}$ mobilization or chemotaxis in FPRL1 expressing cells.

Additionally, we have discovered that synthetic T20/DP178 analogs which lack N-terminal amino acids interact with an FPR member and thereby down-regulate an inflammatory response. Accordingly, T20/DP178 truncated variants are antagonists for FPR member-mediated chemoattraction and activation. Novel biological tools, prophylactics, and therapeutics comprising T20/DP178, T21/DP107 and fragments thereof, as well as, methods of use of the foregoing for modulating an inflammatory response are disclosed.

BRIEF DESCRIPTION OF THE DRAWINGS

FIG. 2C1 shows that fMLP (100 nM) desensitizes calcium ($Ca^{++}$) mobilization in human monocytes loaded with Fura-2 and stimulated with T20/DP178 (100 nM); the ratio of fluorescence at 340 nm and 380 nm wave length was recorded and calculated using the FLWinLab program.

FIG. 2C2 shows that T20/DP178 (100 nM) desensitizes calcium ($Ca^{++}$) mobilization in human monocytes loaded with Fura-2 and stimulated with fMLP (100 nM); the ratio of fluorescence at 340 nm and 380 nm wave length was recorded and calculated using the FLWinLab program.

FIG. 2C3 shows that T20/DP178 (100 nM) desensitizes calcium ($Ca^{++}$) mobilization in neutrophils loaded with Fura-2 and stimulated with fMLP (100 nM); the ratio of fluorescence at 340 nm and 380 nm wave length was recorded and calculated using the FLWinLab program.

FIG. 2C4 shows that fMLP (100 nM) desensitizes calcium ($Ca^{++}$) mobilization in neutrophils loaded with Fura-2 and stimulated with T20/DP178 (100 nM); the ratio of fluorescence at 340 nm and 380 nm wave length was recorded and calculated using the FLWinLab program.

FIG. 3B1 shows that fMLP (100 nM) desensitizes $Ca^{++}$ mobilization in ETFR cells transfected to express FPR and stimulated with T20/DP178 (1 $\mu$M).

FIG. 3B2 shows that T20/DP178 (1 $\mu$M) desensitizes $Ca^{++}$ mobilization in ETFR cells transfected to express FPR and stimulated with fMLP (100 nM).

FIG. 4A1 shows the induction of calcium ($Ca^{++}$) mobilization in human monocytes loaded with Fura-2 and stimulated with fMLP (100 nM).

FIG. 4A2 shows the induction of calcium ($Ca^{++}$) mobilization in human monocytes loaded with Fura-2 and sequentially stimulated with DP719 (50 $\mu$M) (a T20/DP178 analog) followed by fMLP (100 nM).

FIG. 4A3 shows the induction of calcium ($Ca^{++}$) mobilization in human monocytes loaded with Fura-2 and sequentially stimulated with DP712 (50 $\mu$M) (aT20/DP178 analog) followed by fMLP (100 nM).

FIG. 4A4 shows the induction of calcium ($Ca^{++}$) mobilization in human monocytes loaded with Fura-2 and stimulated with MCP-1 (100 nM), a chemokine that was used as a control to verify the specificity of DP719 and DP712.

FIG. 4A5 shows the induction of calcium ($Ca^{++}$) mobilization in human monocytes loaded with Fura-2 and stimulated with T20/DP178 (100 nM).

FIG. 4A6 shows the induction of calcium ($Ca^{++}$) mobilization in human monocytes loaded with Fura-2 and sequentially stimulated with DP719 (50 $\mu$M), followed by T20/DP178 (100 nM), and stimulated with MCP-1 (100 nM) to verify the specificity of DP719.

FIG. 4A7 shows the induction of calcium ($Ca^{++}$) mobilization in human monocytes loaded with Fura-2 and sequentially stimulated with DP712 (50 $\mu$M), followed by T20/DP178 (100 nM), and stimulated with MCP-1 (100 nM) to verify the specificity of DP712.

FIG. 4B1 shows the induction of calcium ($Ca^{++}$) mobilization in ETFR cells transfected to express FPR, loaded with Fura-2, and stimulated with fMLP (100 nM).

FIG. 4B2 shows the induction of calcium ($Ca^{++}$) mobilization in ETFR cells transfected to express FPR, loaded with Fura-2, and sequentially stimulated with DP719 (50 $\mu$M) (aT20/DP178 analog) followed by fMLP (100 nM).

FIG. 4B3 shows the induction of calcium ($Ca^{++}$) mobilization in ETFR cells transfected to express FPR, loaded with Fura-2, and sequentially stimulated with DP712 (50 $\mu$M) (aT20/DP178 analog) followed by fMLP (100 nM).

FIG. 4B4 shows the induction of calcium ($Ca^{++}$) mobilization in ETFR cells transfected to express FPR, loaded with Fura-2, and stimulated with T20/DP178 (100 nM).

FIG. 4B5 shows the induction of calcium ($Ca^{++}$) mobilization in human monocytes loaded with Fura-2 and sequentially stimulated with DP719 (50 $\mu$M) and followed by T20/DP178 (100 nM).

FIG. 4B6 shows the induction of calcium ($Ca^{++}$) mobilization in human monocytes loaded with Fura-2 and sequentially stimulated with DP712 (50 $\mu$M) and followed by T20/DP178 (100 nM).

FIG. 7B1 shows that fMLP (1 $\mu$M) desensitizes calcium ($Ca^{++}$) mobilization in human monocytes loaded with Fura-2 and stimulated with T21/DP107 (1 $\mu$M).

FIG. 7B2 shows that T21/DP107 (1 $\mu$M) desensitizes calcium ($Ca^{++}$) mobilization in human monocytes loaded with Fura-2 and stimulated with fMLP (1 $\mu$M).

FIG. 7D1 shows that fMLP (1 $\mu$M) desensitizes calcium ($Ca^{++}$) mobilization in neutrophils loaded with Fura-2 and stimulated with T21/DP107 (1M).

FIG. 7D2 shows that T21/DP107 (1 $\mu$M) desensitizes calcium ($Ca^{++}$) mobilization in neutrophils loaded with Fura-2 and stimulated with fMLP (1 $\mu$M).

FIG. 8C1 shows that fMLP desensitizes calcium (Ca$^{++}$ mobilization in ETFR cells transfected to express FPR, loaded with Fura-2, and stimulated with T21/DP107.

FIG. 8C2 shows that T21/DP107 desensitizes calcium (Ca$^{++}$) mobilization in ETFR cells transfected to express FPR, loaded with Fura-2, and stimulated with fMLP.

FIG. 8F1 shows that T21/DP107 desensitizes calcium (Ca$^{++}$) mobilization in 293 cells transfected to express FPRL1, loaded with Fura-2, and stimulated with fMLP.

FIG. 8F2 shows that fMLP desensitizes calcium (Ca$^{++}$) mobilization in 293 cells transfected to express FPRL1, loaded with Fura-2, and stimulated with T21/DP107.

DETAILED DESCRIPTION OF THE INVENTION

Figure 1A:
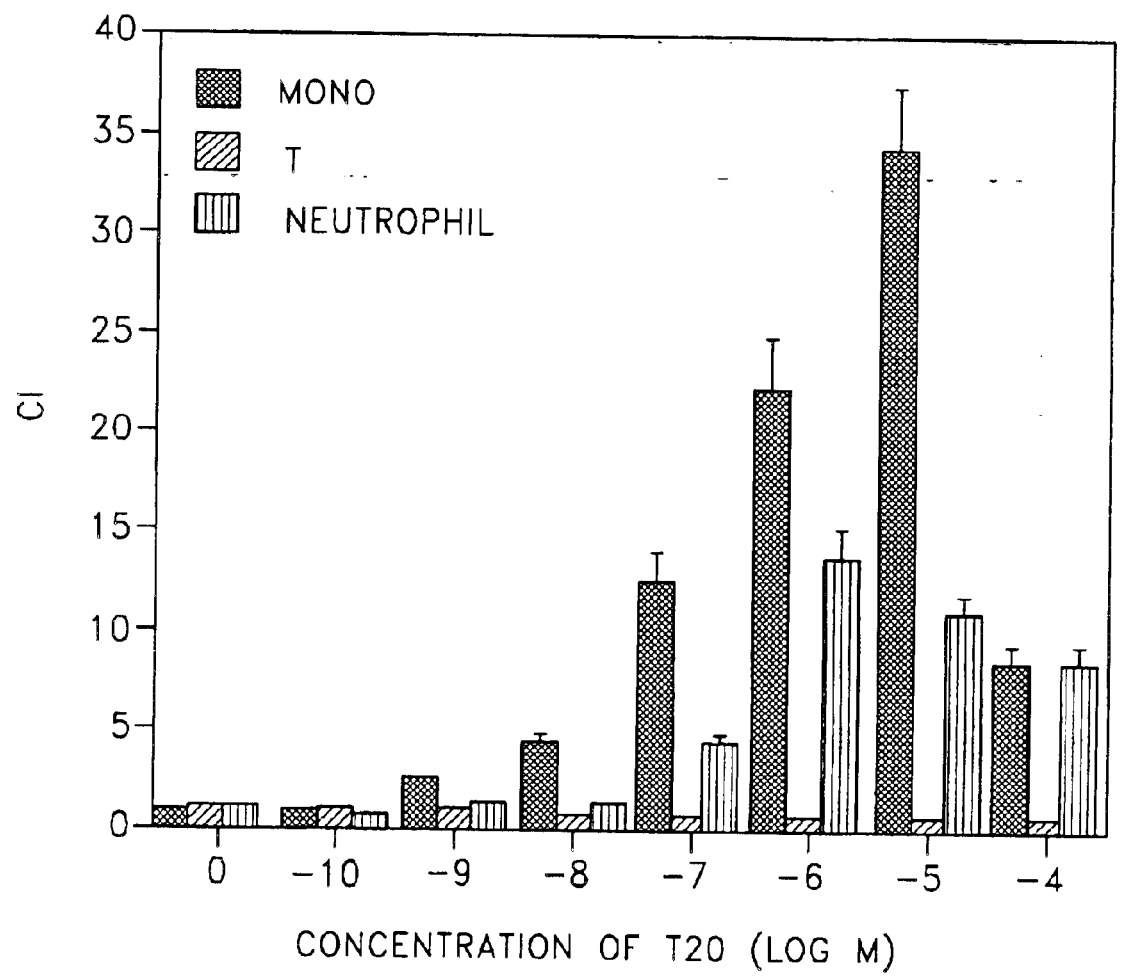
FIG. 1A shows the fold increase of leukocyte migration in response to T20/DP178 over control medium (the CI or chemotaxis index).

In the disclosure below, we teach that several ligands interact with FPR members including, but not limited to, T20/DP178, T21/DP107, and fragments thereof. We have discovered that a novel complex comprising T20/DP178, T21/DP107, or a fragment thereof joined to an FPR member up-regulates or down-regulates an inflammatory response, as marked by chemoattraction and cell activation. We contemplate that the sequence of T20/DP178, T21/DP107, and fragments thereof, as well as, protein models of T20/DP178, T21/DP107, and fragments thereof can be used to identify many more ligands which interact with an FPR member and thereby induce a desired inflammatory response. Thus, many more novel FPR member-ligand complexes can be identified. Several embodiments of the present invention, therefore, include T20/DP178, T21/DP107, and fragments thereof in biotechnological tools for use in discovering a new class of anti-inflammatory agents or agents which modulate an inflammatory response. Other embodiments include therapeutic and prophylactic agents which comprise T20/DP178, T21/DP107, and fragments thereof for use in the treatment and/or prevention of conditions associated with either an impotent inflammatory response or a potent inflammatory response.

The N-formyl peptide receptor (FPR) and its variant FPR-like 1 (FPRL1), are members of a family of receptors referred to as "FPR class" or "FPR members". The FPR class are G-protein-coupled receptors which have seven transmembrane domains. FPR members are typically found on human phagocytic cells but they have also been identified on hepatocytes, and cytokine stimulated epithelial cells. Many other cell types may have FPR members. FPR members interact with chemotactic N-formyl peptides. (Prossnitz and Ye, Pharmacol. Ther. 74: 73 (1997); Murphy, The N-formyl peptide chemotactic receptors, Chemoattractant ligands and their receptors. CRC Press, Boca Raton, p. 269 (1996)). FPR and FPRL1 are expressed by monocytes and neutrophils and are clustered on human chromosome 19q13. (Bao et al., Genomics 13: 437 (1992); and Durstin et al., Biochem. Biophys. Res. Commun. 201: 174 (1994), herein both references are expressly incorporated by reference). FPRL1 was identified and molecularly cloned from human phagocytic cells by low stringency hybridization of the cDNA library with the FPR sequence and was initially defined as an orphan receptor. (Gao and M. Murphy, J. Biol. Chem. 268: 25395 (1993); Murphy et al., J. Biol. Chem. 267: 7637 (1992); Ye et al., Biochem. Biophys. Res. Commun. 184: 582 (1992) and Nomura et al., Int. Immunol. 5: 1239 (1993), herein all references are expressly incorporated by reference). The cloning of the same receptor termed FPRH2 from a genomic library was also described. (Bao et al., Genomics 13: 437 (1992), herein expressly incorporated by reference). FPRL1 possesses 69% identity at the amino acid level to FPR. (Prossnitz and Ye, Pharmacol. Ther. 74: 73 (1997); and Murphy, The N-formyl peptide chemotactic receptors, Chemoattractant ligands and their receptors. CRC Press, Boca Raton, p. 269 (1996), herein both references are expressly incorporated by reference). Many more FPR members may be present and can be rapidly identified by using the cloning methods detailed in the references cited above and the functional assays described herein.

In the following, we disclose our discovery that T20/DP 178 is a chemoattractant and activator of monocytes and neutrophils.

T20/DP178 is a Chemoattractant and Activator of Monocytes and Neutrophils

The synthetic T20/DP178 exhibited potent inhibition on fusion of both T lymphocyte tropic and monocyte tropic HIV-1, as reported previously. (Lawless et al., Biochemistry 35: 13697 (1996)). Its analog T716, T719, T712 showed significant but progressively reduced anti-HIV-1 activity, whereas T914 was ineffective on HIV-1 fusion. (Lawless et al., Biochemistry 35: 13697 (1996)). The biological effects of T20/DP178 was first investigated for its ability to induce human leukocyte migration, a crucial step for cell homing and accumulation at sites of inflammation or injury. This was measured by testing the migratory response of the cells to concentration gradients of the peptide placed in the bottom wells of a micro-chemotaxis chamber. Accordingly, different concentrations of T20/DP178 were placed in the lower wells of a chemotaxis chamber and cell suspension was placed in the upper wells. The upper and lower wells were separated by polycarbonate filters. After incubation, the cells that migrated across the filters were stained and counted. Microscopy (at 200× magnification) revealed significant migration of neutrophils and monocytes across the filters in response to 100 nM T20/DP178 or fMLP. The fold increase of leukocyte migration in response to T20/DP178 over control medium (the chemotactic index or "CI") was also determined. As shown in FIG. 1A, human peripheral blood monocytes and neutrophils, but not CD3$^+$ T lymphocytes, migrated in a dose-dependent manner in response to T20/DP178. The dose-response curve was bell-shaped, a typical pattern shown by known leukocyte chemoattractants, including fMLP and chemokines. (Prossnitz et al., Pharmacol Ther 74:73 (1997); Murphy, Annu. Rev. Immuno. 12: 593 (1994); Oppenheim et al., Annu. Rev. Immunol. 9: 617 (1991); and Murphy, The N-formyl peptide chemotactic receptors, Chemoattractant ligands and their receptors. CRC Press, Boca Raton, p. 269 (1996)).

Figure 1B:
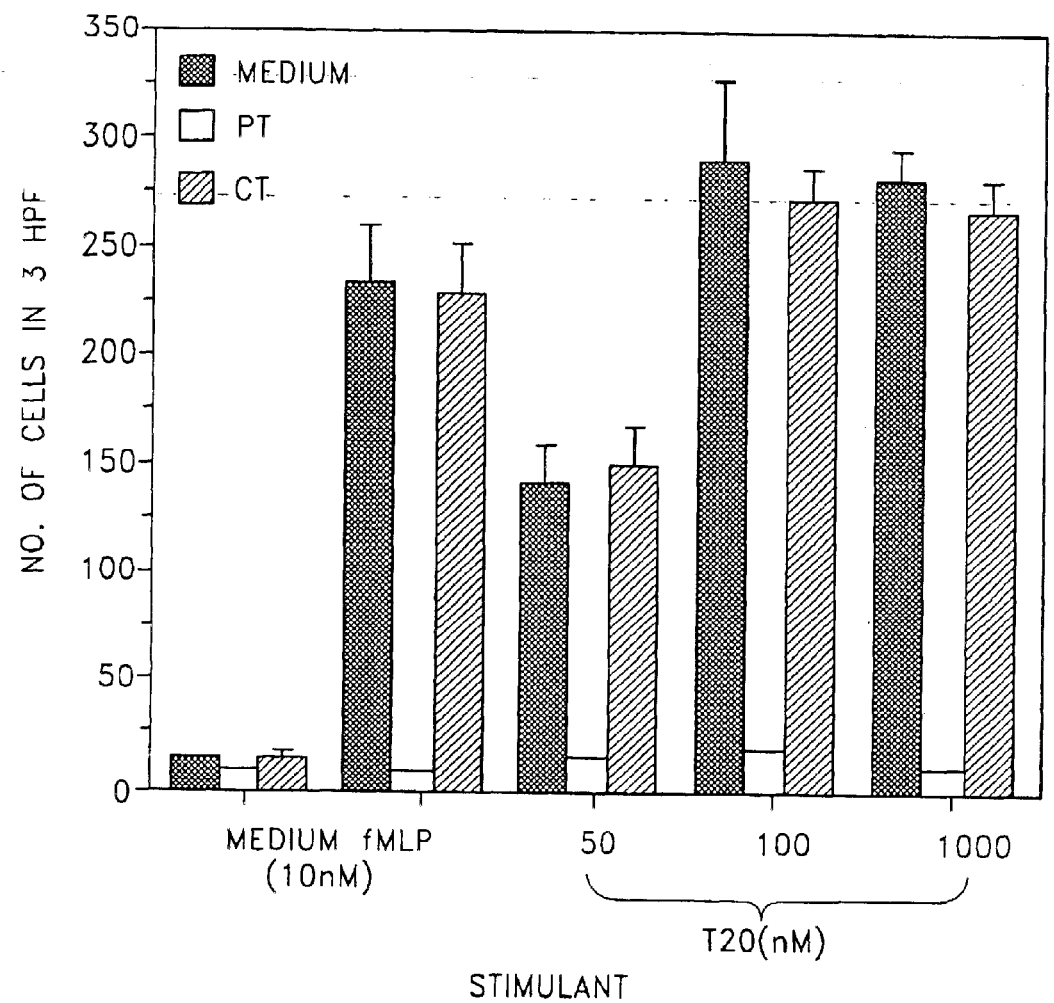
FIG. 1B shows that the induction of monocyte migration mediated by T20/DP178 is inhibited by pretreatment of cells with pertussis toxin ("PT") at 100 ng/ml for 30 min at 37° C. but not cholera toxin ("CT").

We next examined whether the T20/DP178-induced monocyte and neutrophil migration was due to activation of specific receptors. The migration of monocytes and neutrophils in response to T20/DP178 was completely inhibited by pretreatment of the cells with pertussis toxin, but not cholera toxin or herbimycin A (FIG. 1B), demonstrating that a G-protein of the Gi type coupled receptor was involved. (Prossnitz et al., *Pharmacol Ther* 74:73 (1997); Murphy, *Annu. Rev. Immuno.* 12: 593 (1994); Oppenheim et al., *Annu. Rev. Immunol.* 9: 617 (1991); and Murphy, *The N-formyl peptide chemotactic receptors, Chemoattractant ligands and their receptors*. CRC Press, Boca Raton, p. 269 (1996)).

Figure 2A:
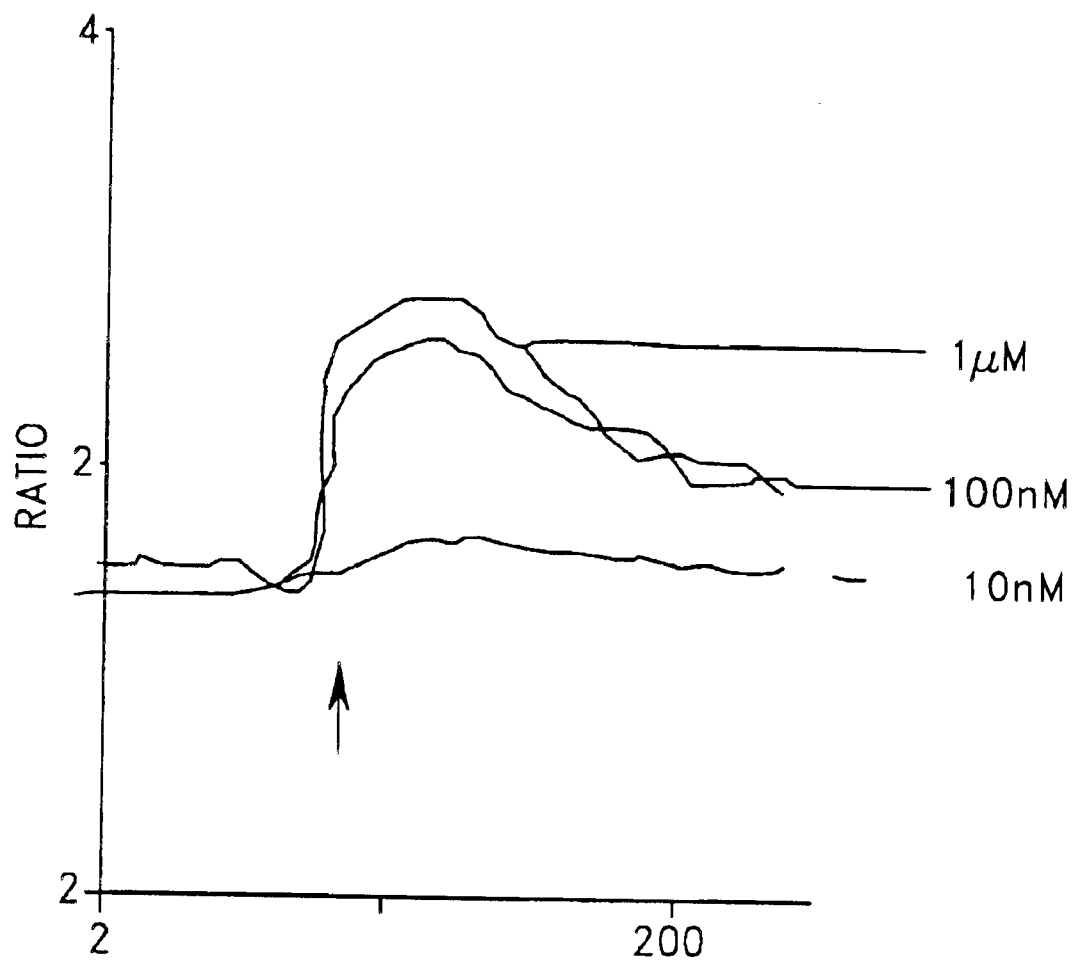
FIG. 2A shows the induction of calcium ($Ca^{++}$) mobilization in human monocytes loaded with Fura-2 and stimulated with different concentrations of T20/DP178; the ratio of fluorescence at 340 nm and 380 nm wave length was recorded and calculated using the FLWinLab program.
Figure 2B:
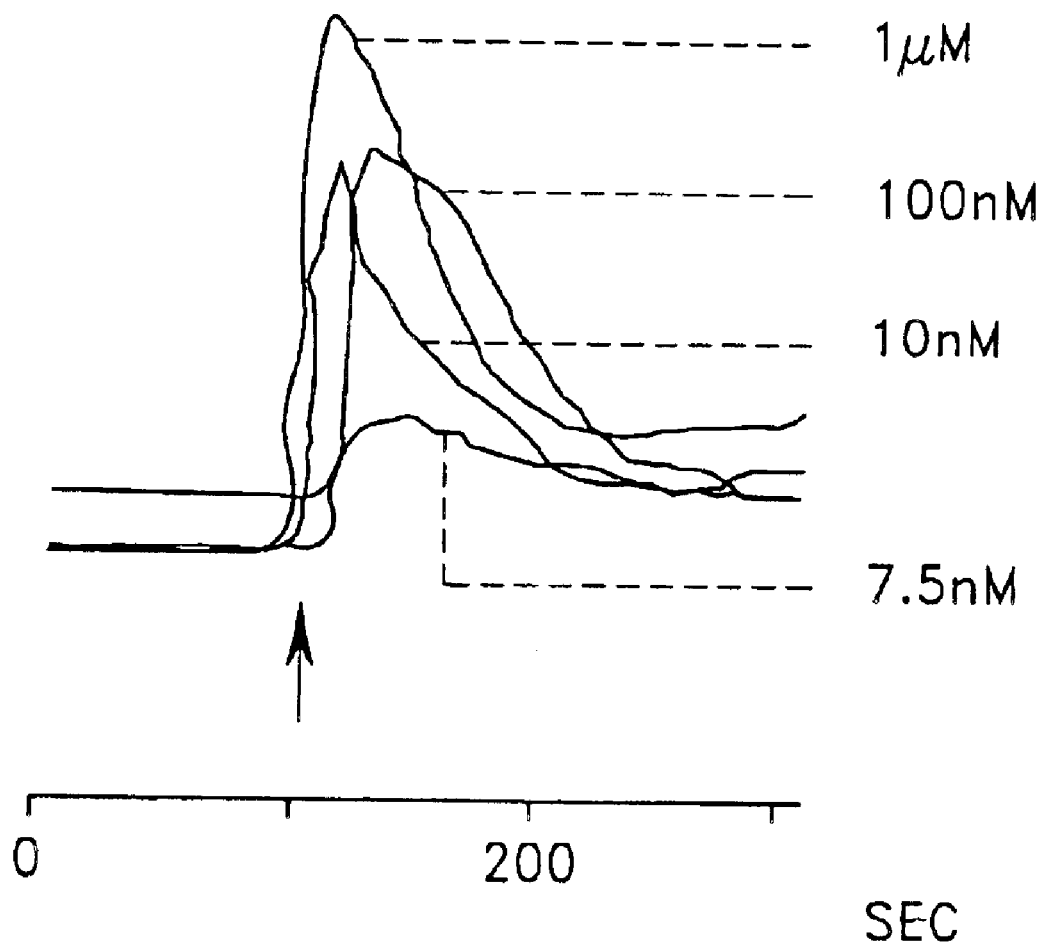
FIG. 2B shows the induction of calcium ($Ca^{++}$) mobilization in neutrophils loaded with Fura-2 and stimulated with different concentrations of T20/DP178; the ratio of fluorescence at 340 nm and 380 nm wave length was recorded and calculated using the FLWinLab program.

The finding above was also supported by the induction of a dose-dependent, and pertussis toxin sensitive, calcium ($Ca^{++}$) mobilization in monocytes and neutrophils by T20/DP178. (FIGS. 2A–2B). Human monocytes or neutrophils were loaded with Fura-2 and then were stimulated with T20/DP178. The ratio of fluorescence at 340 nm and 380 nm wave length was recorded and calculated using the FLWin-Lab program.

The capacity of T20/DP178 to desensitize cell response to subsequent stimulation with other chemoattractants was then tested to determine whether this peptide shared G-protein-coupled receptor(s) with other chemoattractants (FIGS. 2C1–2C4). T20/DP178 did not cross-desensitize the $Ca^{++}$ flux induced by a number of chemokines including IL-8, MCP-1 (monocyte chemotactic protein-1), RANTES, MCP-3 (monocyte chemotactic protein-3), or MIP-1α (macrophage inflammatory protein-1α), thus, T20/DP178 does not share a receptor with any of these chemokines. On the other hand, the bacterial chemotactic peptide fMLP had a marked desensitizing effect on T20/DP178-induced $Ca^{++}$ mobilization in both monocytes (FIGS. 2C1 and 2C2) and neutrophils. (FIGS. 2C3 and 2C4). The desensitization of $Ca^{++}$ flux between fMLP and T20/DP178 was unidirectional when both agonists were used at same concentration (100 nM), since T20/DP178 had negligible effect on subsequent fMLP stimulation. These results unequivocally demonstrate that T20/DP178 interacts with an FPR member and thereby mediates cell migration and cell activation. In the following, we discuss our discovery that T20/DP178 is a functional ligand for FPR members on phagocytic cells.

T20/DP178 is a Functional Ligand for FPR Members on Phagocytic Cells

Figure 3A:
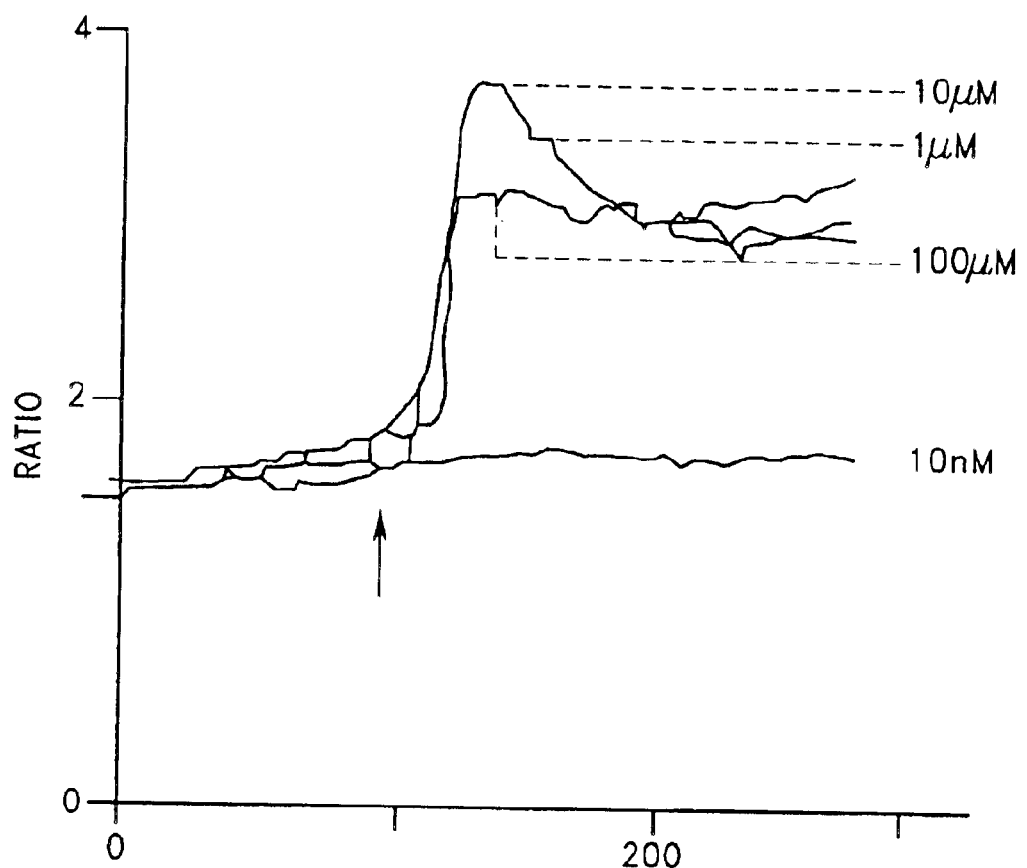
FIG. 3A shows that different concentrations of T20/DP178 can induce $Ca^{++}$ mobilization in a rat basophil cell line (ETFR) that was transfected to express FPR.
Figure 3C:
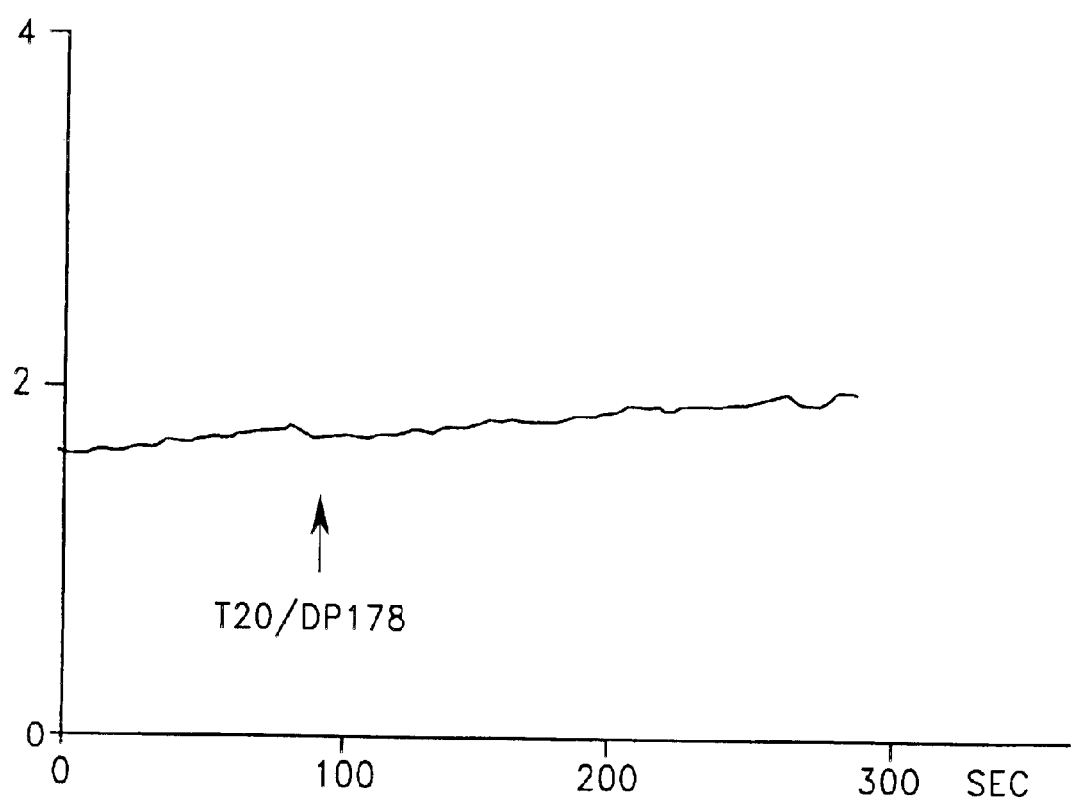
FIG. 3C shows that T20/DP178 did not induce $Ca^{++}$ mobilization in mock-transfected parental cells.

In order to verify whether T20/DP178 binds to one of the fMLP receptors, we tested the effect of T20/DP178 on a rat basophil leukemia cell line transfected with a cDNA encoding an epitope-tagged FPR, the first of the cloned seven transmembrane, G-protein-coupled receptors for fMLP. (Ali et al., *J. Biol. Chem.* 268: 24247 (1993); Ali et al., *J. Biol. Chem.* 271: 3200 (1996); Prossnitz et al., *Pharmacol Ther* 74:73 (1997); Murphy and McDermott, *J. Biol. Chem.* 266: 12560 (1991); and Oppenheim et al., *Ann. Rev. Immunol.* 9:617 (1991). T20/DP178 induced a dose-dependent $Ca^{++}$ mobilization in ETFR cells transfected to express FPR with maximal stimulation at 1 µM concentration. (FIG. 3A). Sequential stimulation of the FPR expressing ETFR cells with fMLP and T20/DP178 or vice versa resulted in bi-directional desensitization, with fMLP being more efficacious, since a higher dose of T20/DP178 was required to completely abolish the cell response to fMLP. (FIGS. 3B1 and 3B2). Neither peptide stimulated $Ca^{++}$ flux in parental cells or mock-transfected cells proving that the response was indeed mediated by FPR in the transfected ETFR cells and that this receptor played a major role in the unidirectional desensitization between fMLP and T20/DP178 in phagocytes. (FIG. 3C).

Figure 3D:
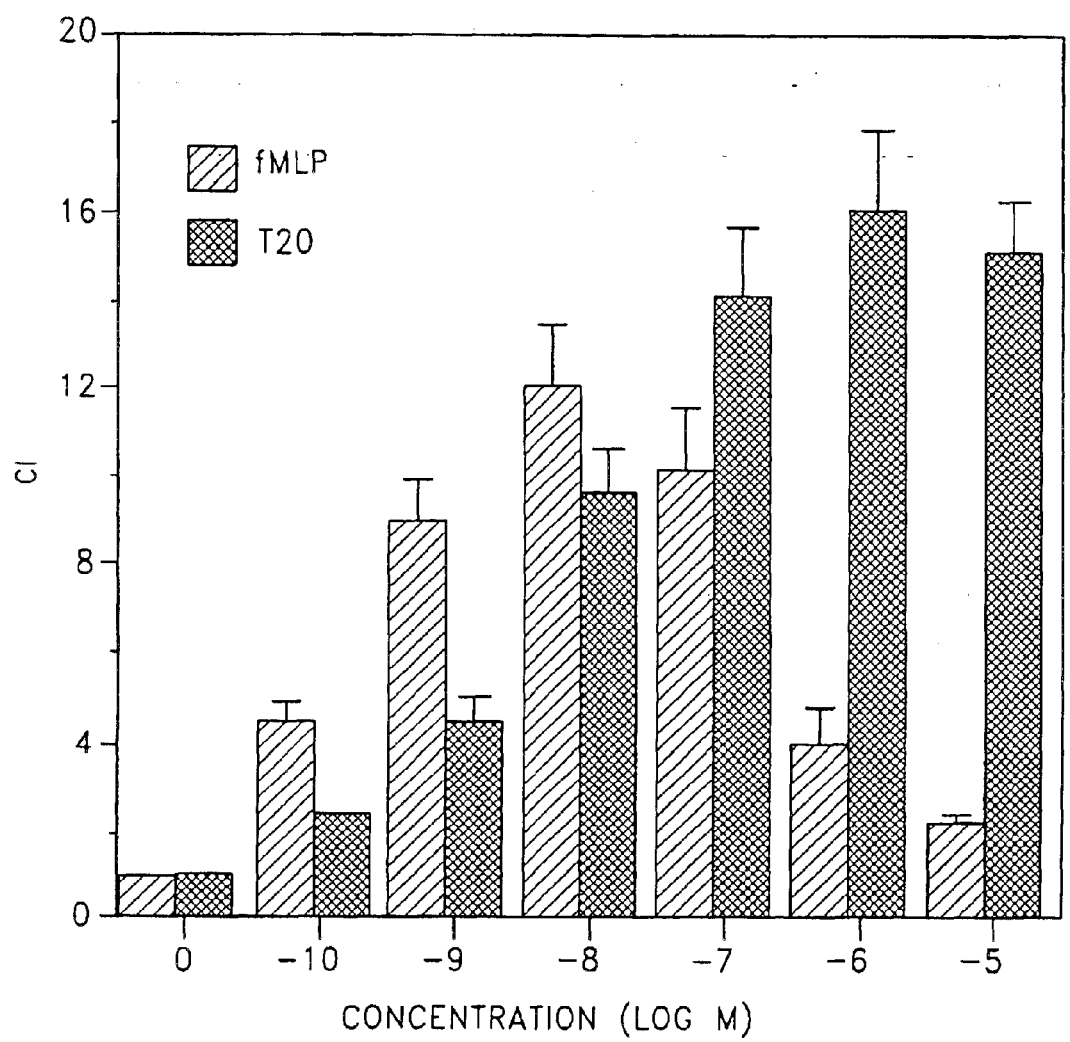
FIG. 3D shows the induction of migration of ETFR cells that were transfected to express FPR by T20/DP178 and fMLP over a range of concentrations (the CI or chemotaxis index).
Figure 3E:
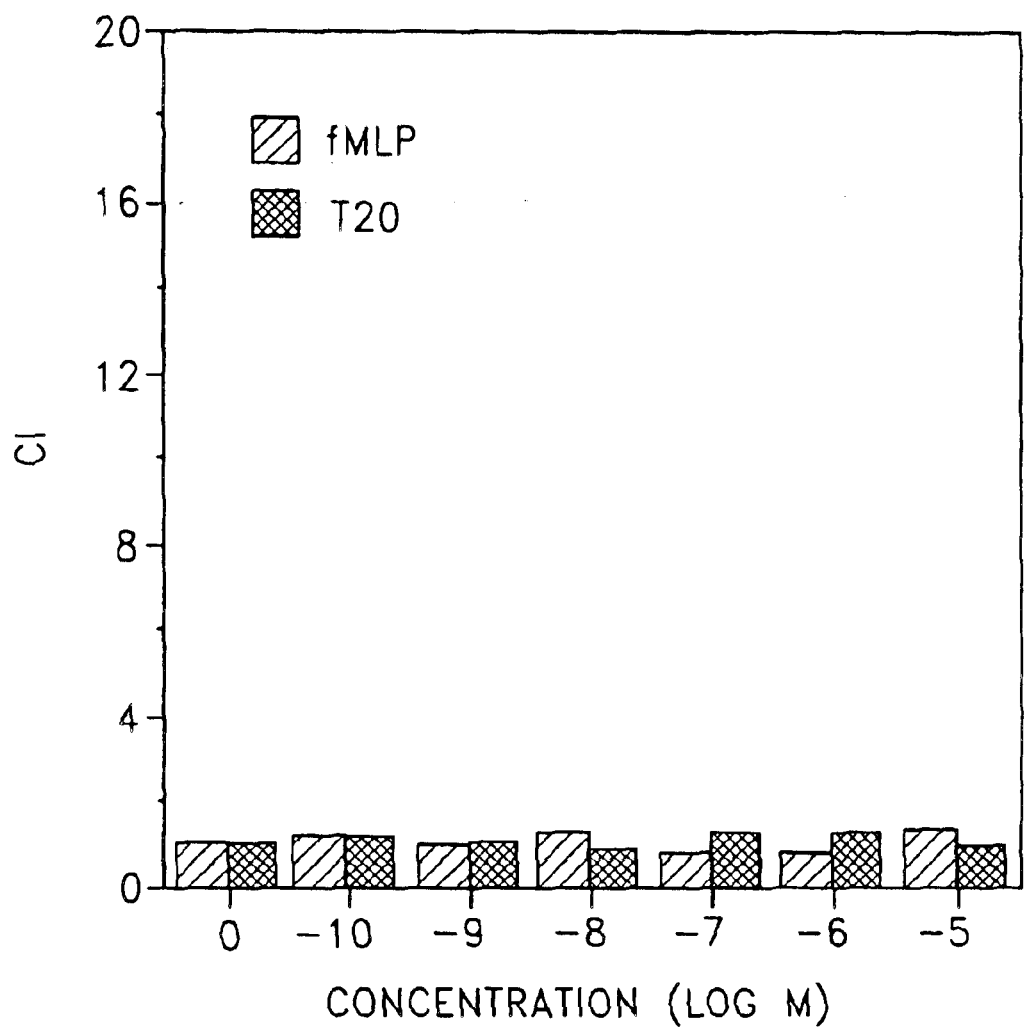
FIG. 3E shows the induction of migration of mock-transfected ETFR cell by T20/DP178 and fMLP over a range of concentrations (the CI or chemotaxis index).

Chemotaxis assays were then used as another sensitive biological parameter to assess the function of the FPR in FPR expressing ETFR cells, as in our previous studies with chemokine receptors. (Gong et al., *J. Biol. Chem.* 273: 4289 (1998); Gong et al., *J. Biol. Chem.* 272: 11682 (1997); and Ben-Baruch et al., *J. Biol. Chem.* 270: 22123 (1995)). ETFR cells were induced by fMLP to migrate across polycarbonate filters coated with extracellular matrix protein, collagen type I, with an $EC_{50}$ of about 500 pM, while T20/DP178 induced a more pronounced migration of the ETFR cells, although with lower potency (EC50 5 nM) than fMLP. (FIG. 3D). In contrast, T20/DP178 or fMLP did not induce migration of mock-transfected cells. (FIG. 3E).

Figure 3F:
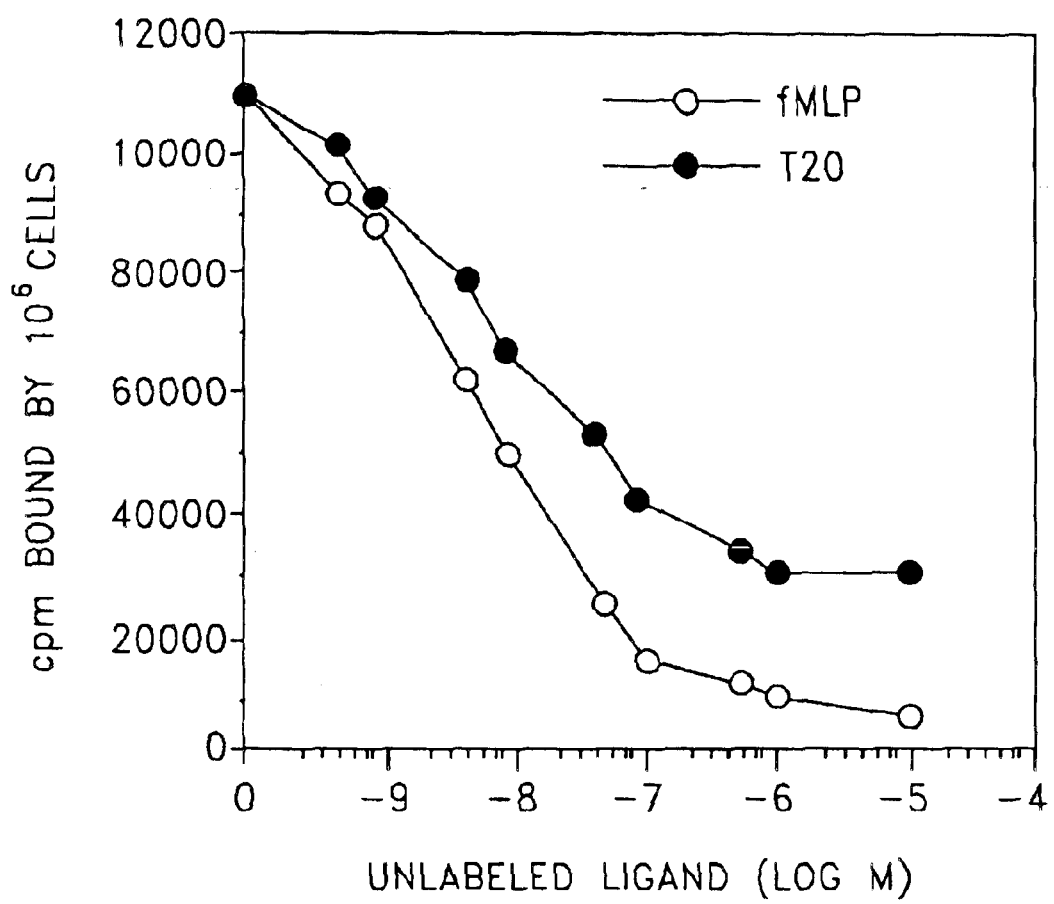
FIG. 3F shows that T20/DP178 can displace $^3$H-fMLP binding to ETFR cells.

In order to confirm that T20/DP178 is acting at FPR, we used ligand binding competition experiments with $^3$H-labeled fMLP. T20/DP178 effectively competed with $^3$H-fMLP for binding to FPR expressing ETFR cells, although with a less potency compared with unlabeled fMLP. (FIG. 3F). The $IC_{50}$ for T20/DP178 was about 5 nM and the $IC_{50}$ for fMLP was about 1 nM, in agreement with the chemotactic and $Ca^{++}$ mobilizing activity of both agonists for the FPR expressing ETFR cells.

Evidence that T20/DP178 is an FPR agonist was also provided by the detection of a rapid phosphorylation of FPR following stimulation of FPR expressing ETFR cells with T20/DP178. Phosphorylation of FPR was measured by incubating [$^{32}$P]-orthophosphate labeled ETFR cells with medium alone or T20/DP178 at 37° C. for 15 min and an equivalent amount of cell lysate for each treatment was immunoprecipitated with an anti-epitope (anti-HA) antibody. Immunoprecipitates were separated on a gel and a 65 kDa phosphorylated protein species was detected. This protein was identical to the phospho-protein detected in immunoprecipitates of fMLP treated cells.

It was also determined that T20/DP178 induced a time- and dose-dependent activation of mitogen activated protein kinase (MAPK) in human monocytes, a signaling event that can be initiated by fMLP. (Krump et al., *J Biol Chem* 272:937 (1997); and Torres and Ye, *J Biol Chem* 271:13244 (1996)). MAPK activation was examined in human monocytes by treating the cells with different concentrations of T20/DP178 at various time intervals followed by immunoprecipitation of cell lysates with an anti-p38 MAPK antibody. The immunoprecipitates were then separated on a gel and immunoblotted with a mouse anti-phosphotyrosine antibody. The immunoblot revealed that T20/DP178 induced phosphorylation of MAPK. These results clearly established that T20/DP178 was interacting with an FPR member and that this interaction induced $Ca^{++}$ mobilization, signal transduction, and chemotaxis. In the disclosure below, we provide evidence that fragments of T20/DP178 are antagonists of FPR members.

Analogs of T20/DP178 are Antagonists of FPR Members

A number of FPR agonistic peptides have been reported. (Prossnitz et al., *Pharmacol Ther* 74:73 (1997); Murphy and McDermott, *J. Biol. Chem.* 266: 12560 (1991); Murphy, *Annu. Rev. Immuno.* 12: 593 (1994); Murphy, *The N-formyl peptide chemotactic receptors, Chemoattractant ligands and their receptors*. CRC Press, Boca Raton, p. 269 (1996); and Gao et al., *J. Exp. Med.* 180: 2191 (1994)). However, T20/DP178 derived from HIV-1 gp41 does not bear any substantial sequence identity with the reported FPR agonistic peptides including the absence of an N-formyl group. By way of explanation only and not to limit any aspect of our present invention, we believe that it is the conformation of T20/DP178, rather than the primary sequence, that determines its activity. Thus, in several embodiments, we contemplate using FPR models and methods of rational drug design, preferably using "fuzzy functional forms" (FFF)—a three-dimensional descriptor of the active site of a protein, to identify many more ligands which interact with FPR members. (See the discussion below and Fetrow et al., *J. Mol. Biol.* 282:703–711 (1998) and Fetrow and Skolnick, *J. Mol. Biol.* 281: 949–968 (1998), herein incorporated by reference).

In addition to T20/DP178, we tested 4 synthetic T20/DP178 analogs that lack 3 (T716), 5 (T719), 7 (T712), and 12 (T914) amino acids respectively at the N-terminus of T20/DP178. (FIGS. 4A1–A7 and 4B1–B6). Accordingly, monocytes or FPR-expressing ETFR cells were loaded with Fura-2 and then were sequentially stimulated with T20/DP178 analogs D719 or D712 (50 µM) and fMLP (100 nM) or T20/DP178 (100 nM). The chemokine MCP-1 (100 nM) was used as a control to indicate the specificity of D719 or D712. All the analogs failed to induce significant $Ca^{++}$ mobilization in monocytes or the FPR-expressing ETFR cells. Instead, they abolished $Ca^{++}$ mobilization in response to subsequent T20/DP178 or fMLP stimulation in both types of phagocytic leukocytes and FPR-expressing ETFR cells but they did not affect monocyte response to chemokines such as MCP-1.

Figure 5A:
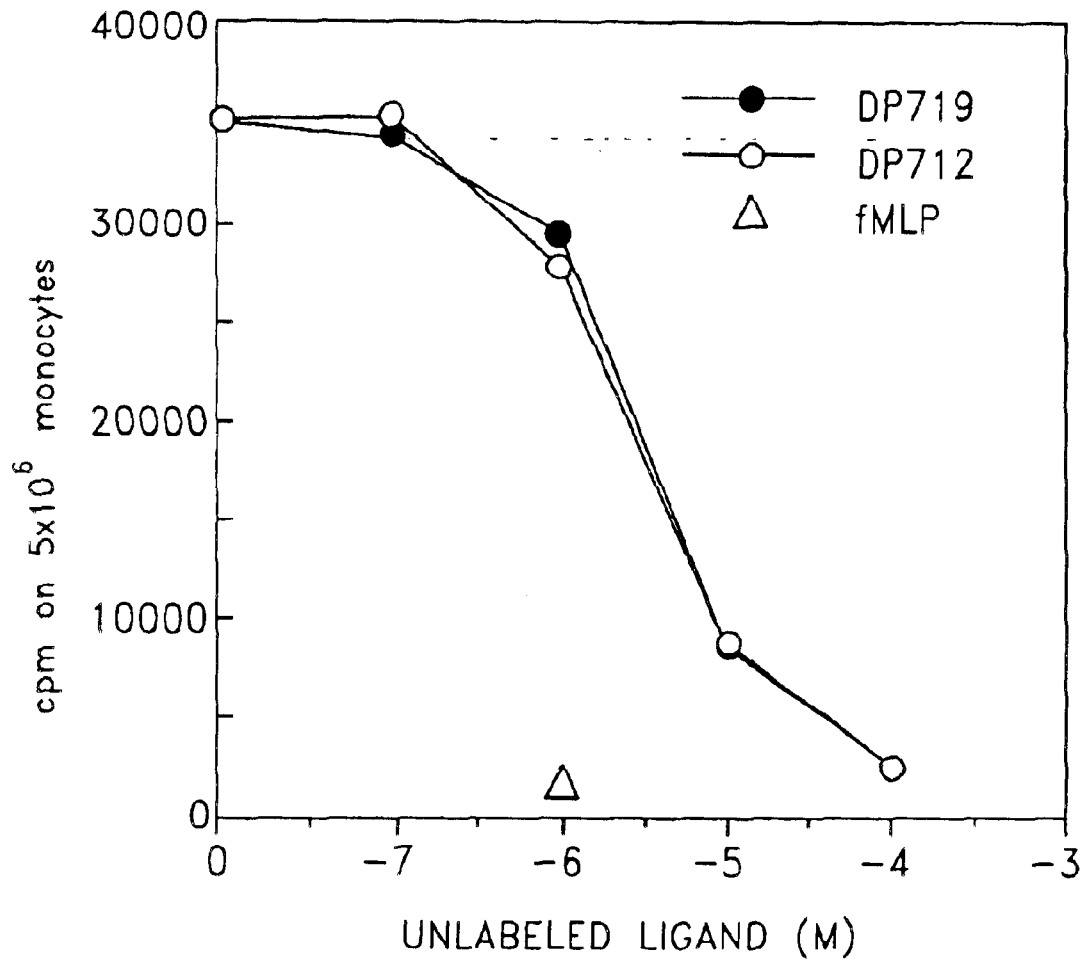
FIG. 5A shows that an increase in the concentration of DP719 or DP712 results in an increase in the inhibition of binding of a constant concentration $^3$H-fMLP to human monocytes.
Figure 5B:
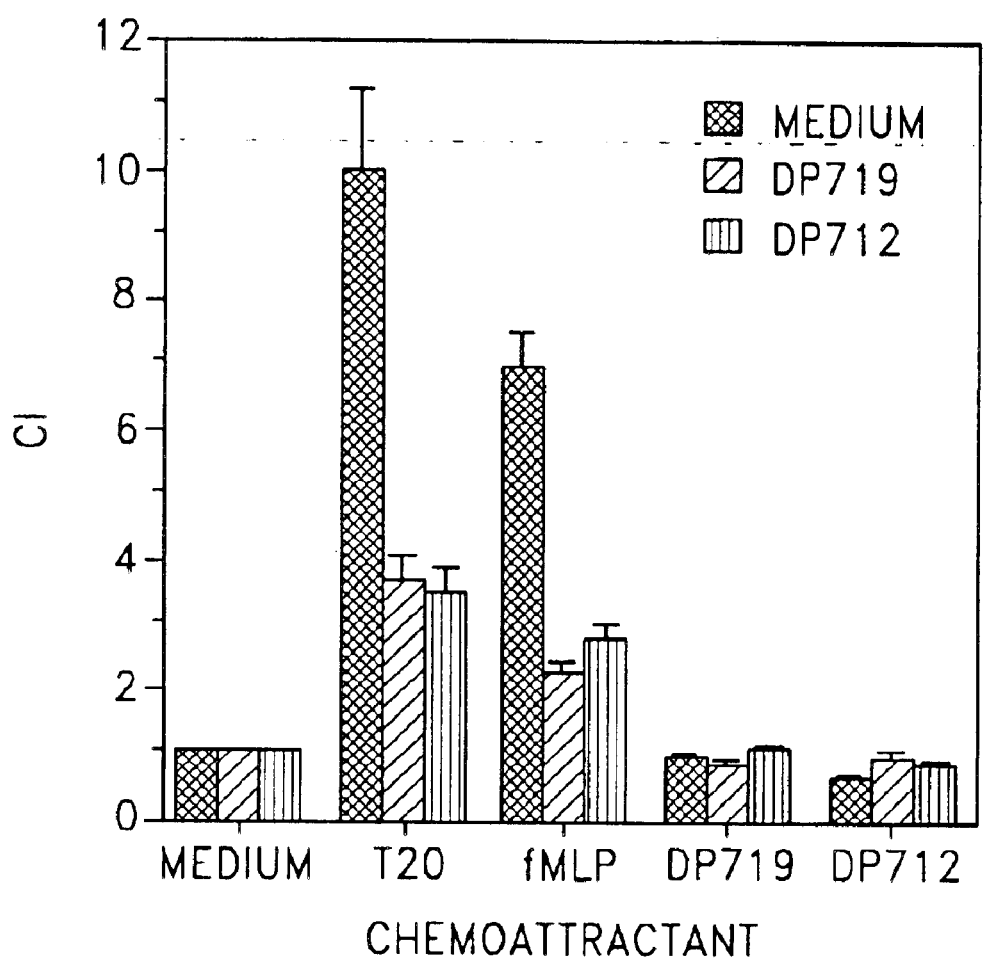
FIG. 5B shows that the presence of DP719 or DP712 results in an decrease in T20/DP178 or fMLP-mediated cell migration of ETFR cells that were transfected to express FPR (the CI or chemotaxis index).

The synthetic T20/DP178 truncated analogs also specifically inhibited $^3$H-fMLP binding and significantly attenuated migration of FPR-expressing ETFR cells that were induced by T20/DP178 and fMLP. (FIGS. 5A and 5B). In the binding study, different concentrations of DP719 or DP712 were added to aliquots of human monocytes containing a constant concentration of $^3$H-fMLP. After incubation at 37° C. for 20 min, the cells were harvested and measured for β-emission. Unlabeled fMLP at 1 µM was used as a positive control. The cell migration analysis was conducted by placing T20/DP178 (1 µM) or fMLP (100 nM) in the lower wells of a chemotaxis chamber and FPR expressing ETFR cells at 1×10$^6$/ml in the upper wells of the chamber in the presence or absence of 50 µM DP917 or DP912. After incubation, the cells that migrated across the filters were counted. The chemotactic index (CI), which determines the fold increase of migration over the medium (control) was calculated. *P<0.01 (Student's t test) compared with the migration of cells incubated with medium alone. The migration experiments revealed that DP917 or DP912 did not affect the cell migration in response to medium alone nor did DP917 or DP912 induce ETFR cell migration. These results provided evidence that deletion of 3–12 amino acids from the N-terminus of T20/DP178 produced FPR antagonists. In the following section, we describe our finding that the peptide T21/DP107 is a chemoattractant and activator of monocytes and neutrophils.

T21/DP107 is a Chemoattractant and Activator of Monocytes and Neutrophils

Figure 6A:
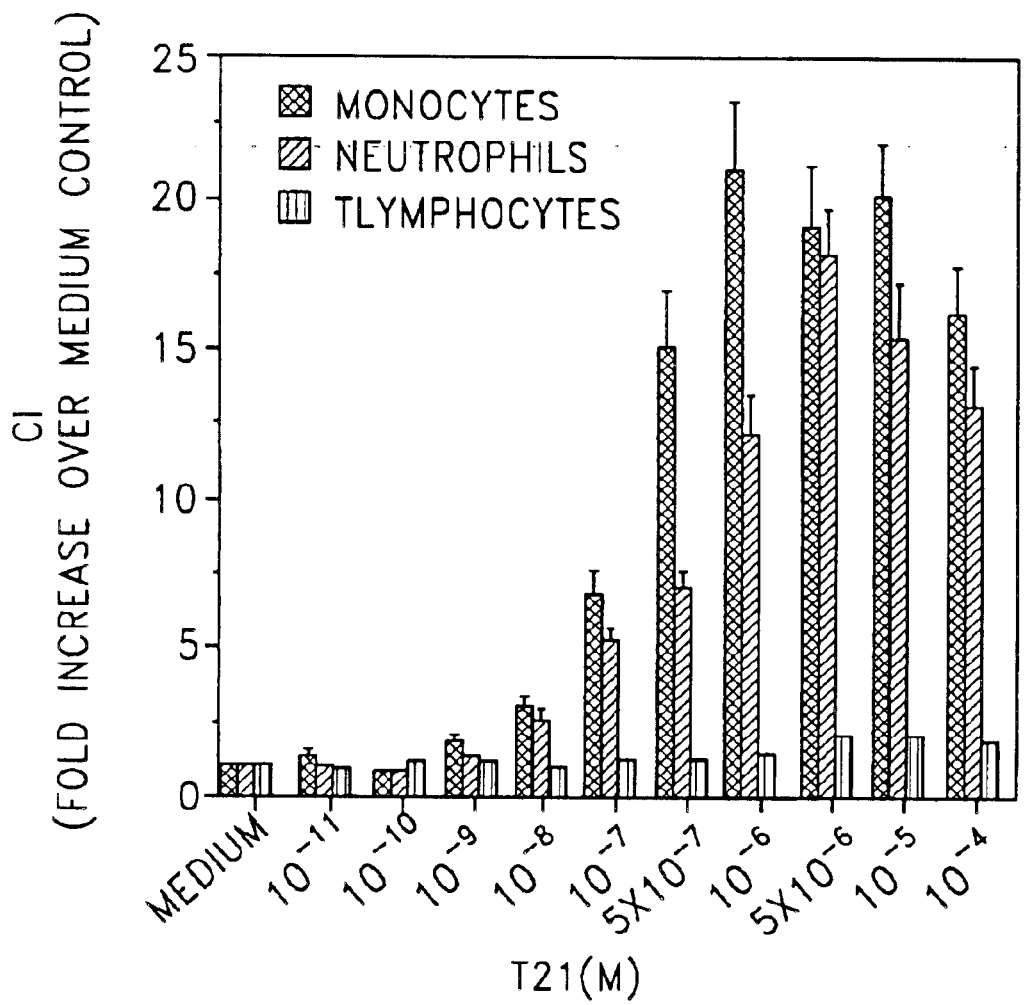
FIG. 6A shows the fold increase of leukocyte migration in response to T21/DP107 over control medium (the CI or chemotaxis index).

Initially, we tested whether synthetic T21/DP107 could induce human leukocyte migration, a crucial step for cell homing and accumulation at sites of inflammation or injury. Different concentrations of T21/DP107 (1 µM for microscopy experiments) were placed in the lower wells of a chemotaxis chamber and a cell suspension was placed in the upper wells. fMLP (100 nM) was used as a control. The upper and lower wells were separated by polycarbonate filters. After incubation, the cells that migrated across the filters were stained and counted. Microscopy of stained cells revealed that both human peripheral blood monocytes and neutrophils migrated in response to 1 µM T21/DP107. The chemotaxis analysis also revealed that monocytes and neutrophils migrate in a dose-dependent manner in response to a varying concentrations of T21/DP107. The fold increase of leukocyte migration in response to T21/DP107 over control medium (the CI index) was calculated and is shown in FIG. 6A. The chemotactic activity of T21/DP107 was significant at nM concentrations for both monocytes and neutrophils and the cell response remained high with only slight reduction when T21/DP107 was used at $10^{-5}$–$10^{-4}$ M. In contrast, human CD3+ T lymphocytes showed a marginally significant migration (CI=2) in response to high concentrations ($5\times10^{-6}$ M and higher), proving that the effect of T21/DP107 was mainly on phagocytic cells. The analysis showed that monocytes migrated when higher concentrations of T21/DP107 were present in the lower wells of the chemotaxis chamber (TABLE 1).

TABLE 1

Checkerboard analysis of monocyte migration in response to T21/DP107[a]

| T21 in lower wells (M) | Number of migrated cells in 1HPF (mean ± SE) T21 in upper wells (M) | | | |
|---|---|---|---|---|
| | Medium | $10^{-8}$ | $10^{-7}$ | $10^{-6}$ |
| Medium | 20 ± 1 | 11 ± 2 | 7 ± 1 | 9 ± 2 |
| $10^{-8}$ | 40 ± 4[b] | 28 ± 3 | 7 ± 2 | 10 ± 3 |
| $10^{-7}$ | 64 ± 3[b] | 43 ± 2[b] | 25 ± 4 | 26 ± 3 |
| $10^{-6}$ | 132 ± 6[b] | 110 ± 3[b] | 89 ± 6[b] | 57 ± 4[b] |

[a]Different concentrations of T21/DP107 were placed in the upper and/or lower wells of the chemotaxis chamber, monocytes at 2 × 10$^6$/ml were placed in the upper wells. The upper and lower wells were separated by a polycarbonate filter. After incubation, the non-migrating cells were removed and the filter was fixed, stained and the cells migrated across the filter were counted in three high powered fields (HPF, 400 x). The results are expressed as the mean value (± SE) of the cells 1 HPF. Similar results were obtained in two separate experiments.
[b]P < 0.01 compared with migration in the presence of medium alone in both upper and lower wells as determined by Student's test.

Enhanced cell migration was not observed when higher concentrations of T21/DP107 were present in the upper wells. With equal concentrations of T21/DP107 in both upper and lower wells, a slightly increased monocyte migration was observed. These results prove that the cell migration induced by T21/DP107 resulted from a chemotactic effect, albeit chemokinesis contributed slightly.

Figure 6B:
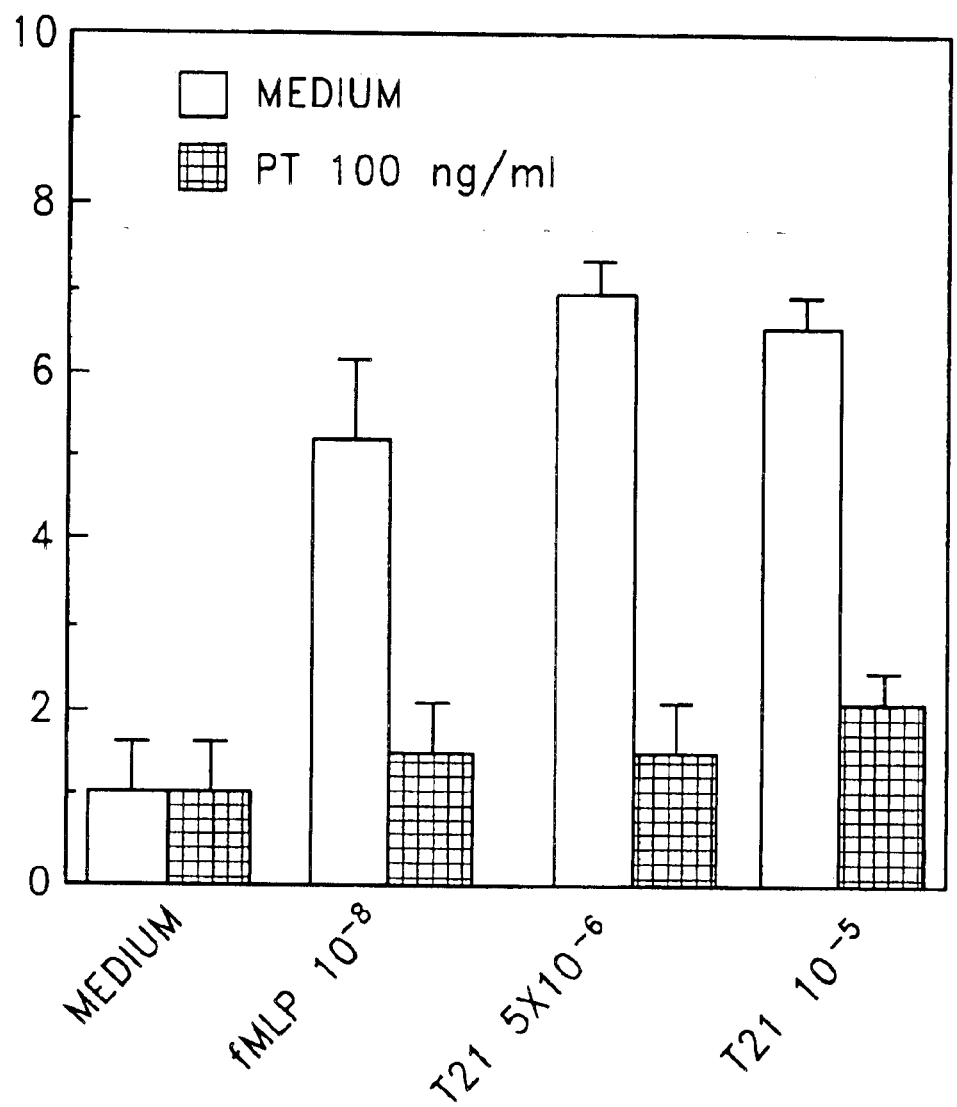
FIG. 6B shows the inhibition of monocyte migration in response to T21/DP107 by pretreatment of the cells with pertussis toxin ("PT") at 100 ng/ml for 30 min at 37° C. (the CI or chemotaxis index).
Figure 7A:
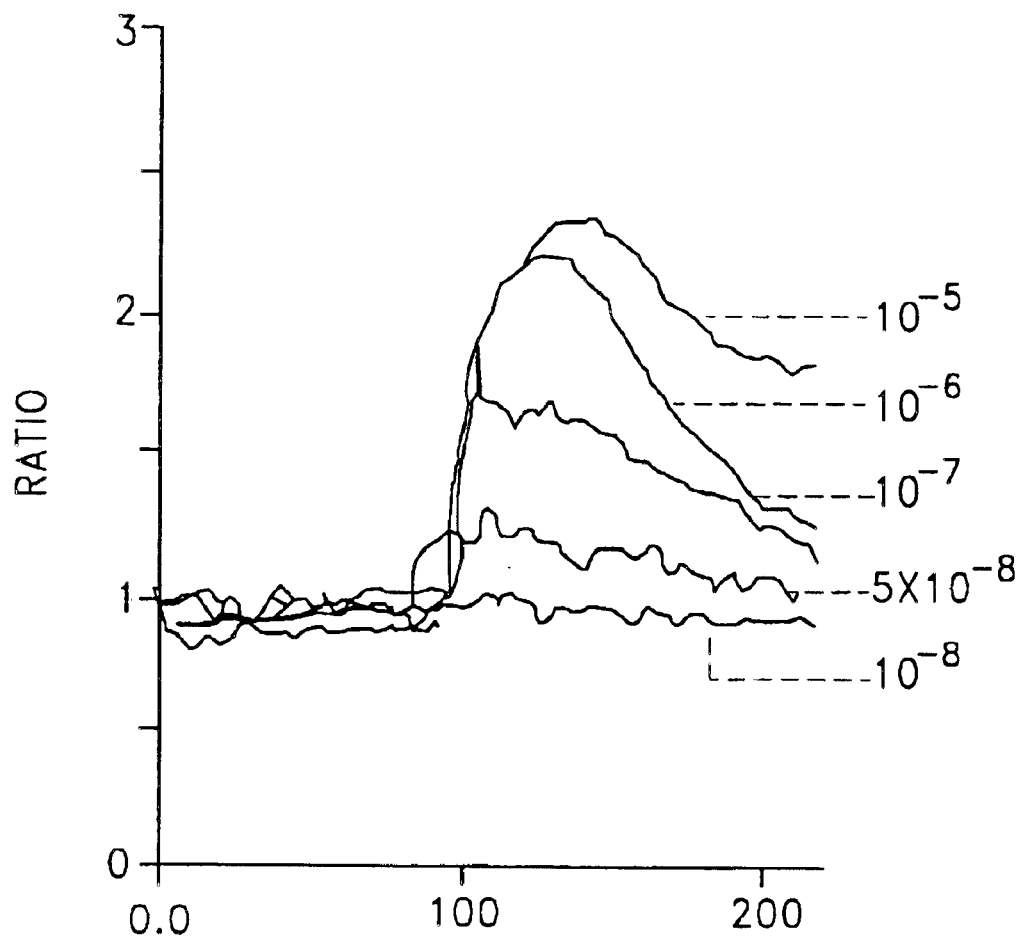
FIG. 7A shows the induction of calcium ($Ca^{++}$) mobilization in human monocytes loaded with Fura-2 and stimulated with different concentrations of T21/DP107.
Figure 7C:
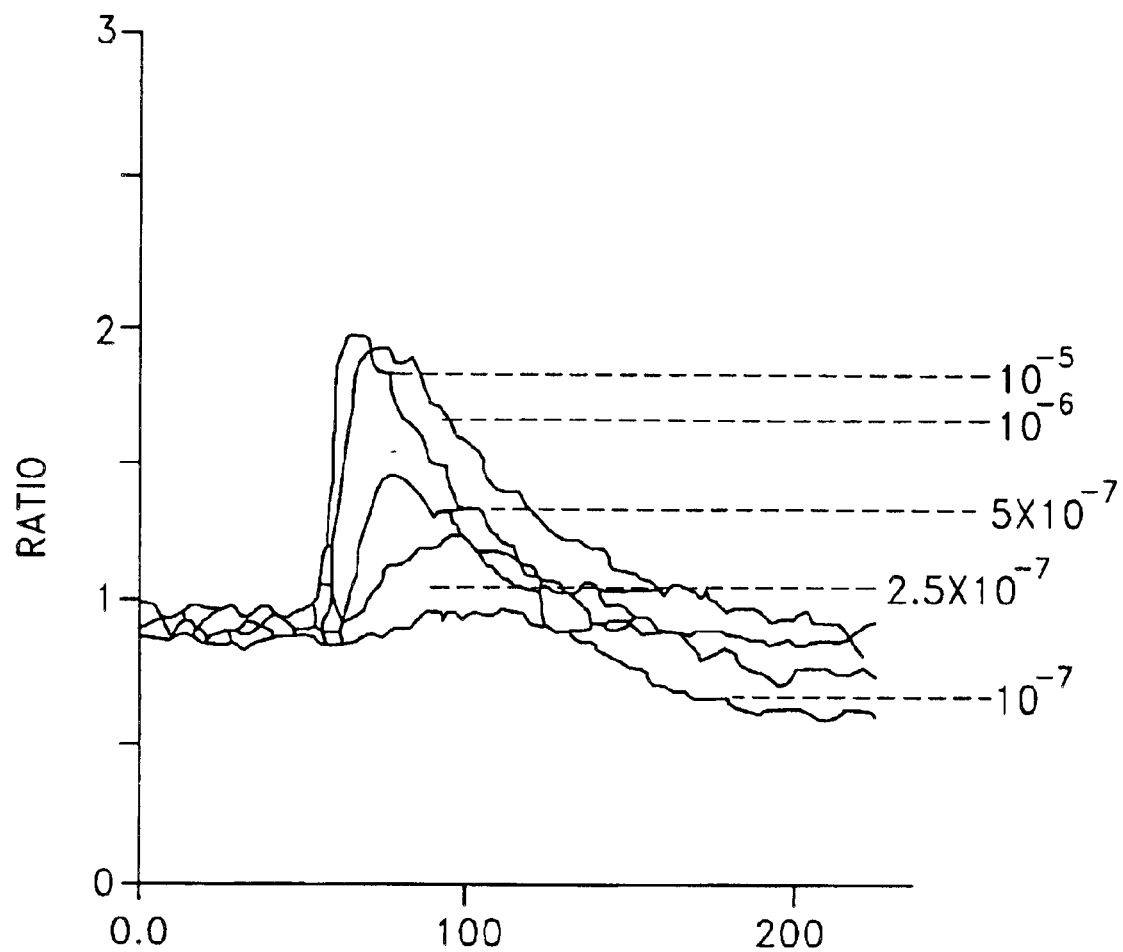
FIG. 7C shows the induction of calcium ($Ca^{++}$) mobilization in neutrophils loaded with Fura-2 and stimulated with different concentrations of T21/DP107.

FIG. 6B further shows that monocyte migration in response to T21/DP107 can be inhibited by pretreatment of the cells with pertussis toxin ("PT") at 100 ng/ml for 30 min at 37° C. That is, the migration of monocytes and neutrophils in response to T21/DP107 was completely inhibited by pretreatment of the cells with pertussis toxin, but not by cholera toxin or herbimycin A, proving that a G-protein of the Gi type coupled receptor was involved. (Prossnitz and Ye, *Pharmacol. Ther.* 74: 73 (1997); Murphy, *The N-formyl peptide chemotactic receptors, Chemoattractant ligands and their receptors.* CRC Press, Boca Raton, p. 269 (1996); Murphy and McDermott, *J. Biol. Chem.* 266: 12560 (1991); Murphy, *Annu. Rev. Immuno.* 12: 593 (1994); Oppenheim et al., *Annu. Rev. Immunol.* 9: 617 (1991); and Gao et al., *J. Exp. Med.* 180: 2191(1994)).

The finding above was further supported by the potent induction of a dose-dependent, and pertussis toxin sensitive, calcium ($Ca^{++}$) mobilization in monocytes and neutrophils by T21/DP107. The $Ca^{++}$ mobilizing activity of T21/DP107 was significant at nM concentrations indicating that this synthetic peptide is a potent activator of human phagocytic cells. The possibility that byproduct(s) formed during peptide synthesis/purification might account for the activity of T21/DP107 was proven unlikely, since a fusion peptide (aa 517–532 of gp41) synthesized during the same period as T21/DP107 did not posses any chemotactic or Ca$^{++}$ mobilizing activity in phagocytes. In the following section, we discuss our discovery that T21/DP107 is a functional ligand for FPR members on phagocytic cells.

T21/DP107 is a Functional Ligand for FPR Members on Phagocytic Cells

In order to characterize the molecular nature of the receptor(s) on phagocytic cells which interact with T21/DP107, a series of cross-desensitization experiments were performed using a variety of chemoattractants. (FIGS. 7A, 7B1, 7B2, 7C, 8D1, and 8D2). Accordingly, human monocytes or neutrophils were loaded with Fura-2 and then were stimulated with various concentrations of T21/DP107. The ratio of fluorescence at 340 nm and 380 nm wave length was recorded and calculated using the FLWinLab program. The desensitization of T21/DP107 (1 $\mu$M) induced Ca2+ flux by fMLP (1 $\mu$M) in monocytes or neutrophils was then determined. In these experiments it was observed that T21/DP107 did not desensitize the Ca$^{++}$ flux in monocytes or neutrophils induced by chemokines such as MCP-1, RANTES, MCP-3, MIP-1$\alpha$, IL-8 and SDF-1. Therefore, T21/DP107 does not share a receptor with any of these chemokines. However, high concentrations ($\geqq$1 $\mu$M) of the bacterial chemotactic N-formylated peptide fMLP had a partial desensitizing effect on T21/DP107-induced Ca$^{++}$ mobilization in both monocytes and neutrophils. In contrast, T21/DP107 did not significantly desensitize the effect of fMLP. These results clearly established that T21/DP107 was interacting with a formyl peptide receptor and this interaction induced Ca$^{++}$ mobilization.

Figure 8A:
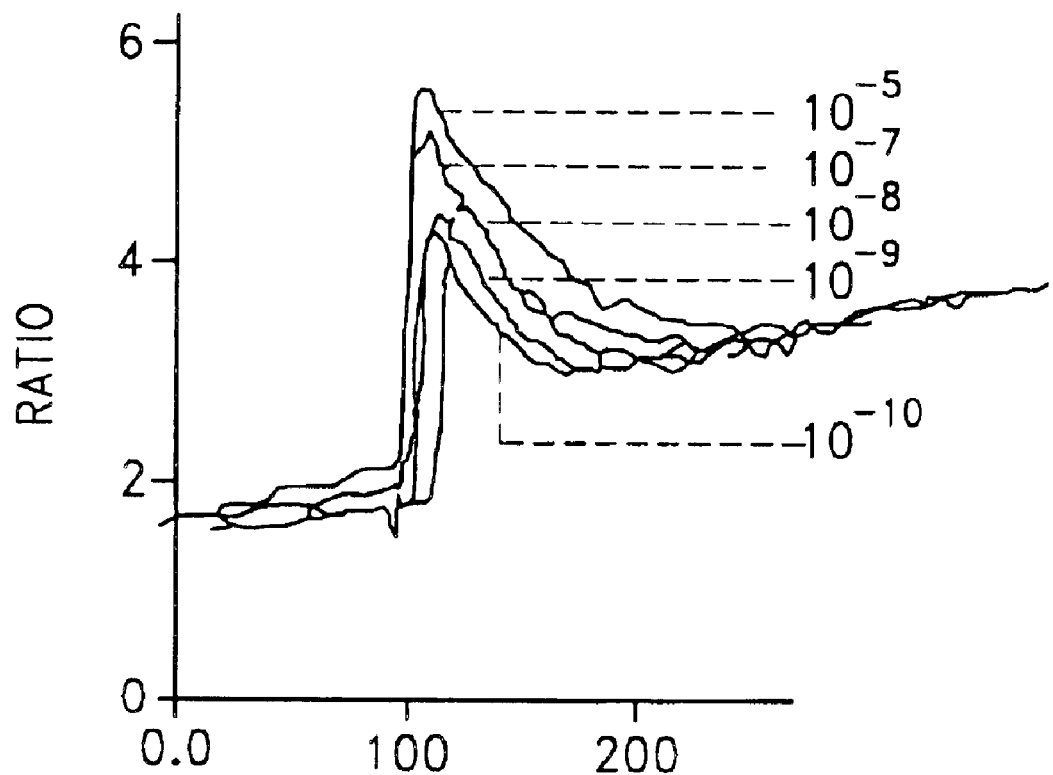
FIG. 8A shows the induction of calcium (Ca$^{++}$) mobilization in ETFR cells transfected to express FPR, loaded with Fura-2, and stimulated with fMLP.
Figure 8B:
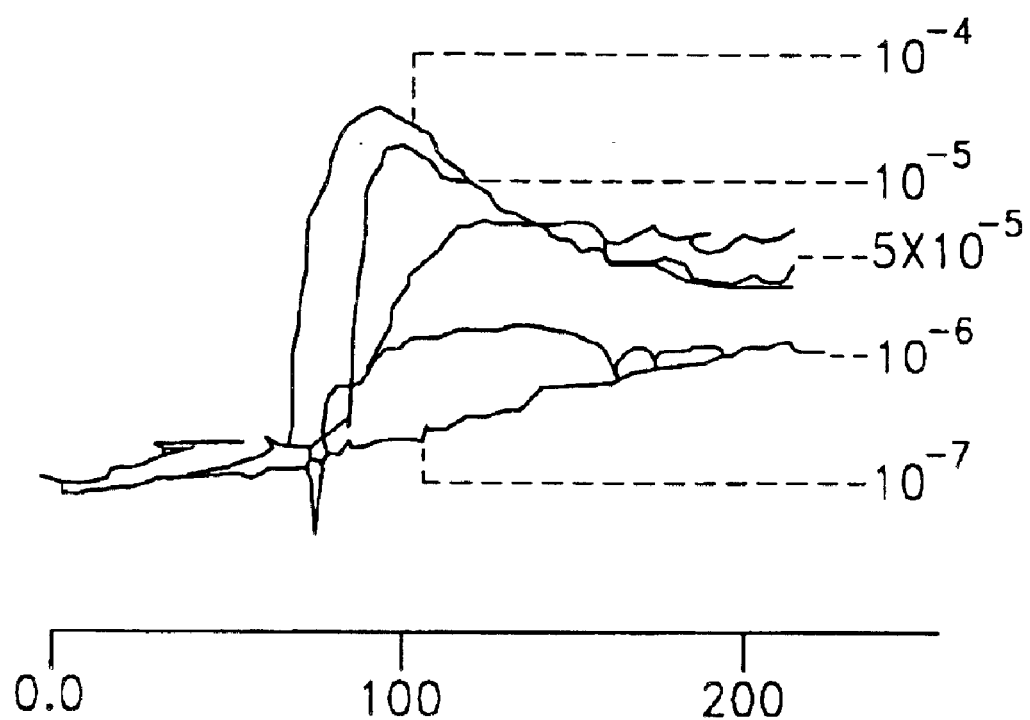
FIG. 8B shows the induction of calcium (Ca$^{++}$) mobilization in ETFR cells transfected to express FPR, loaded with Fura-2, and stimulated with T21/DP107.
Figure 8D:
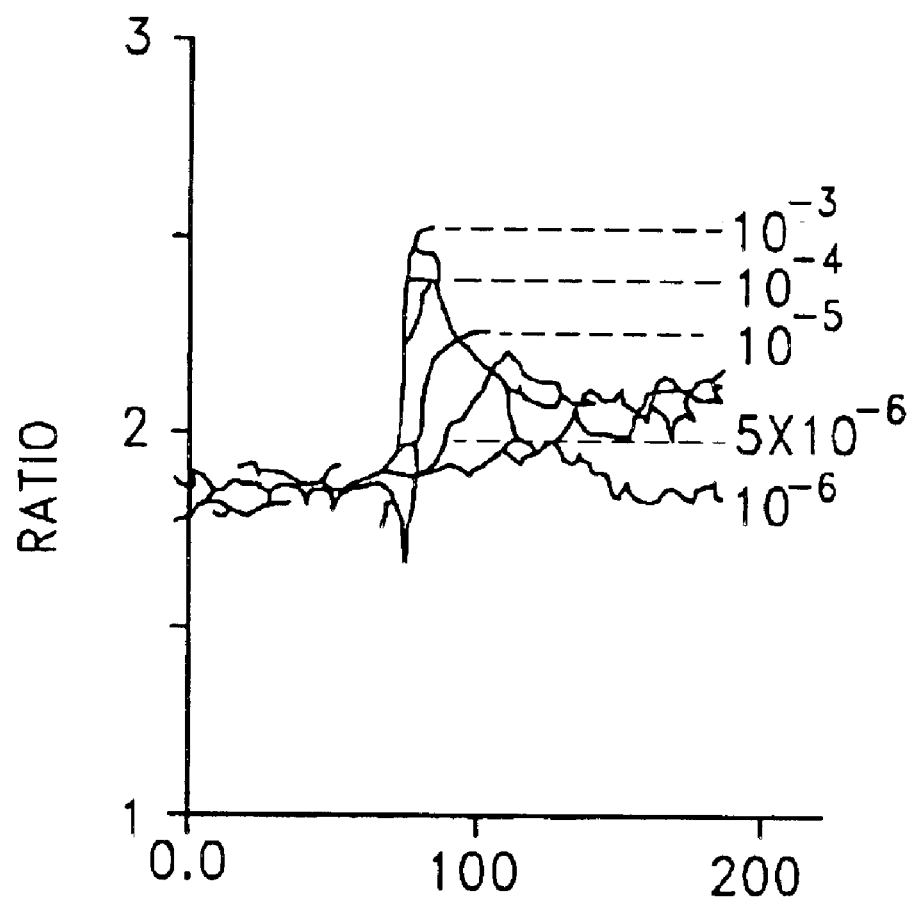
FIG. 8D shows the induction of calcium (Ca$^{++}$) mobilization in 293 cells transfected to express FPRL1, loaded with Fura-2, and stimulated with fMLP.
Figure 8E:
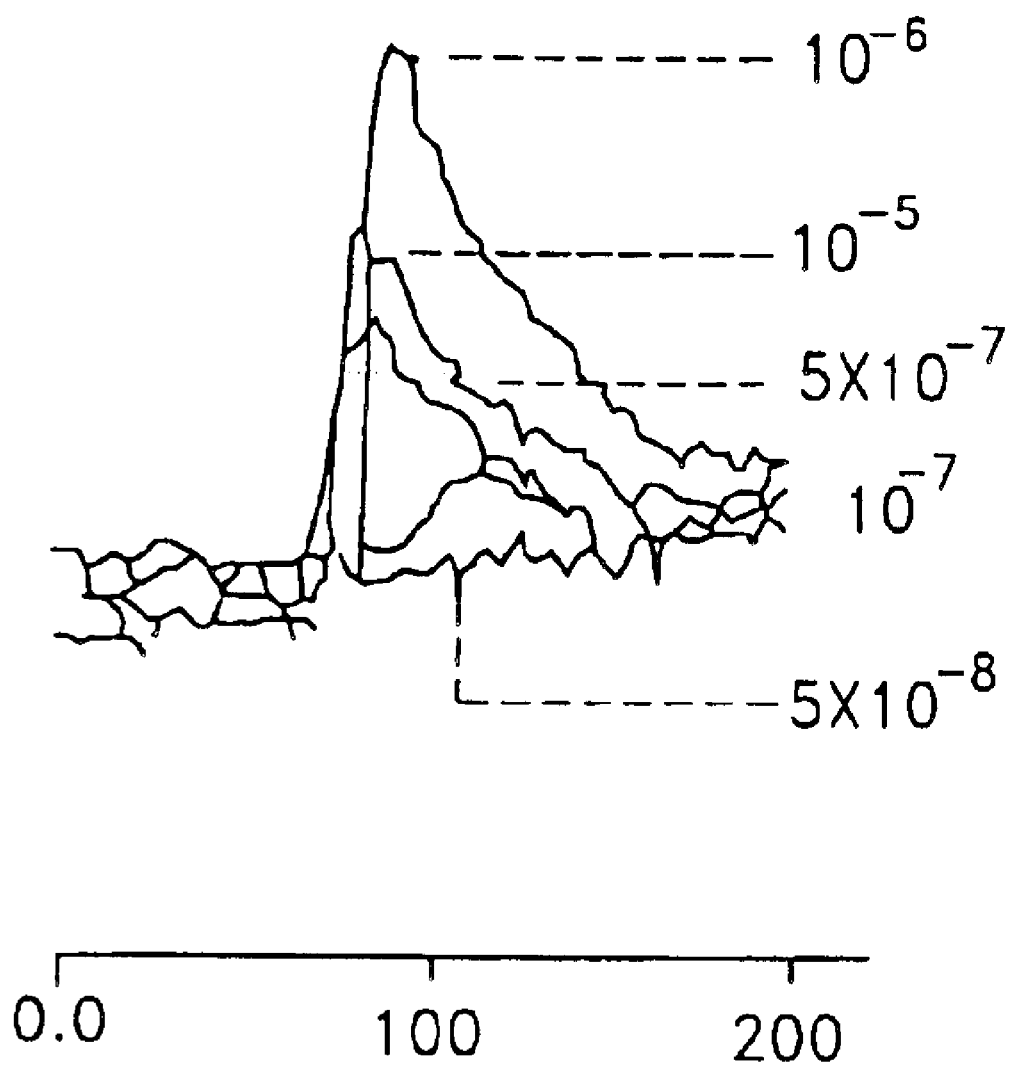
FIG. 8E shows the induction of calcium (Ca$^{++}$) mobilization in 293 cells transfected to express FPRL1, loaded with Fura-2, and stimulated with T21/DP107.

Since fMLP was known to induce Ca$^{++}$ mobilization in phagocytes through at least two seven transmembrane, G-protein-coupled receptors, both members of the FPR class (e.g., FPR and FPRL1), we tested the effect of T21/DP107 on FPR and FPRL1 expressing human cells that, prior to transfection with a nucleic acid encoding the receptors, were not responsive to fMLP stimulation. (Prossnitz and Ye, *Pharmacol. Ther.* 74: 73 (1997); Murphy, *The N-formyl peptide chemotactic receptors, Chemoattractant ligands and their receptors.* CRC Press, Boca Raton, p. 269 (1996); and Gao and M. Murphy, *J. Biol. Chem.* 268: 25395 (1993)). Over a wide range of concentrations, fMLP induced Ca$^{++}$ mobilization in FPR-transfected rat basophil leukemia cell line (ETFR cells), with a minimal effective dose being at low pM concentration range. (FIG. 8A). In contrast, the minimal effective concentration for fMLP to induce Ca$^{++}$ mobilization in FPRL1 transfected cells (FPRL1/293 cells) was at low $\mu$M range. (FIG. 8D). The synthetic T21/DP107 also induced Ca$^{++}$ mobilization in cells transfected with either of these receptors. (FIGS. 8B and 8E). However, the minimal effective dose for T21/DP107 to activate FPRL1 was at nM range as compared with low $\mu$M range on FPR, demonstrating that T21/DP107 activates FPRL1 with higher efficacy.

A comparison of the interaction of T21/DP107 and fMLP on the two receptors was next performed. In FPR expressing cells, a 10$^{-10}$ fMLP concentration versus a 10$^{-5}$ concentration of T21/DP107 were required to induce a change in the ratio of 2 at 340/380 nm wavelength fluorescence; whereas in FPRL1/293 cells, a 5×10$^{-5}$ fMLP concentration versus a 5×10$^{-7}$ T21/DP107 concentration were required to induce a change in the ratio of 0.6. These results established that T21/DP107 was a more potent agonist for FPRL1 than fMLP. This finding was further supported by results of cross-desensitization of Ca$^{++}$ flux between T21/DP107 and fMLP in both receptor transfectants. Although sequential stimulation of the cells expressing FPR or FPRL1 with T21/DP107 and fMLP resulted in bidirectional desensitization, a 1000-fold excess of fMLP was required to desensitize the effect of T21/DP107 in FPRL1/293 cells. (FIGS. 8C1, 8C2, 8F1, and 8F2). Conversely, a much higher concentration of T21/DP107 was necessary to completely abolish the fMLP response of cells expressing FPR. In control experiments, T21/DP107 and fMLP did not induce any Ca$^{++}$ mobilization in parental or mock transfected rat basophil cell line and HEK 293 cells. These results provide more evidence that FPR and FPRL1 are differentially activated by fMLP and T21/DP107.

Figure 9A:
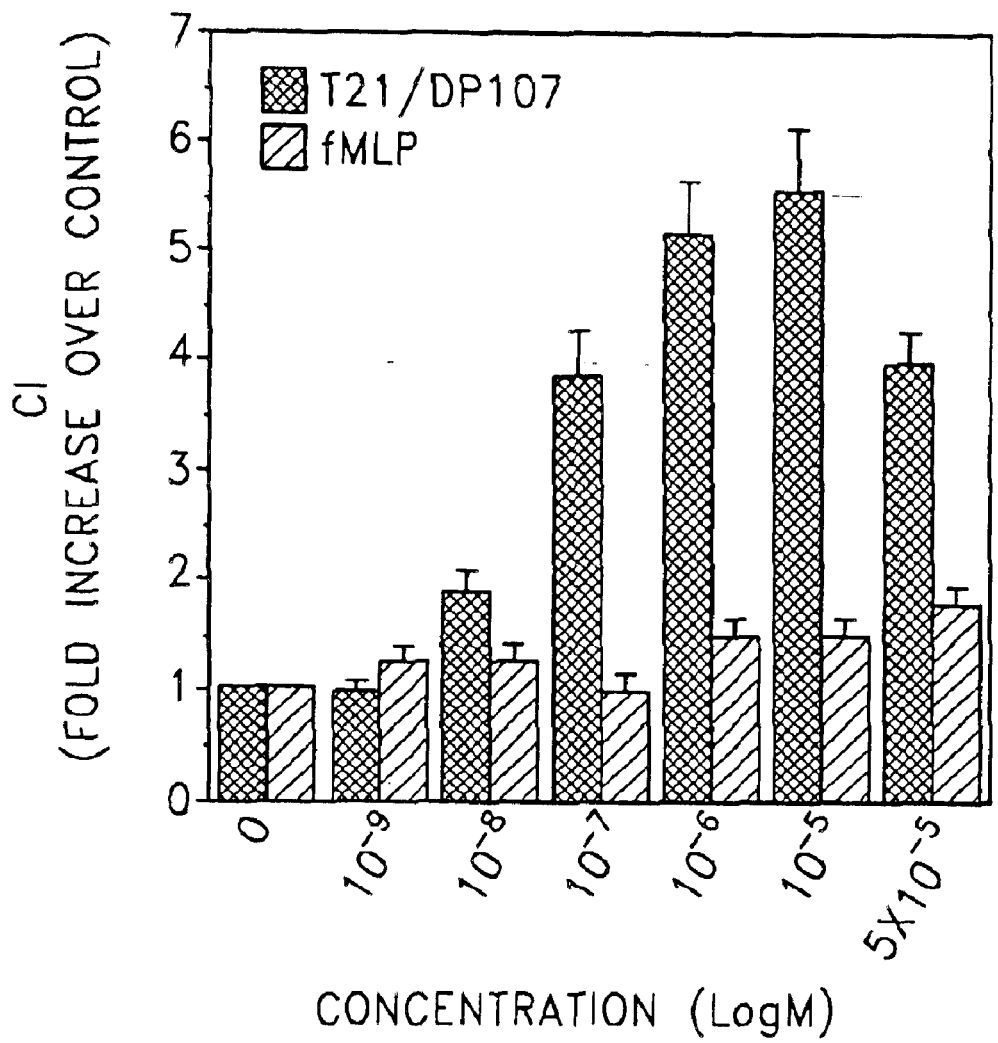
FIG. 9A shows the fold increase of 293 cells transfected to express FPRL1 in response to T21/DP107 over control medium (the CI or chemotaxis index).
Figure 9B:
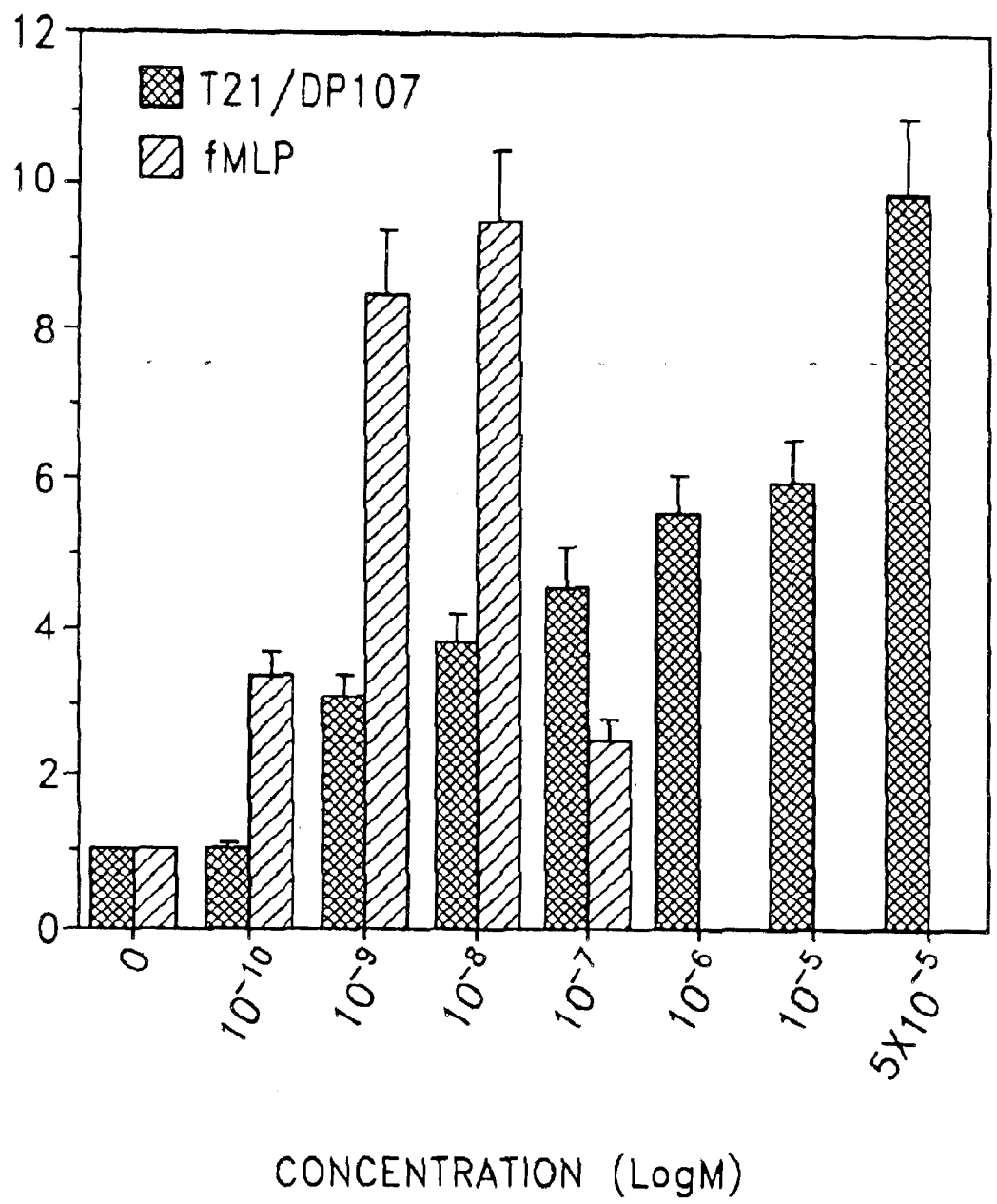
FIG. 9B shows the fold increase of ETFR cells transfected to express FPRL1 in response to T21/DP107 over control medium (the CI or chemotaxis index).

The chemotactic response of cells transfected with with a nucleic acid encoding FPR or FPRL1 was tested as another sensitive parameter to assess the receptor targets of T21/DP107. (Gong et al., *J. Biol. Chem.* 273: 4289 (1998); Gong et al., *J. Biol. Chem.* 272:11682 (1997); and Ben-Baruch et al., *J. Biol. Chem.* 270: 22123 (1995)). Accordingly, different concentrations of T21/DP107 were placed in the lower wells of a chemotaxis chamber and a cell suspension was placed in the upper wells. The upper and lower wells were separated by polycarbonate filters precoated with mouse collagen type I. After incubation, the cells that migrated across the filters were stained and counted. FPRL1/293 cells showed a marked migratory response to T21/DP107 when compared to FPRL1/293 cells contacted with medium alone. The CI (chemotaxis index), which represents the fold increase of leukocyte migration in response to T21/DP107 over control medium, was also determined. FIG. 9A shows that FPRL1/293 cells migrated in response to stimulation with T21/DP107 with an EC50 of 50 nM, but these cells failed to migrate in response to a wide range of concentrations of fMLP. In contrast, ETFR cells were induced to migrate by fMLP at nM range concentrations, but much higher concentrations of T21/DP107 were required to induce the migration of the same cells. (FIG. 9B). These chemotaxis experiments prove that fMLP is only a partial agonist for FPRL1 since it did not induce FPRL1 expressing cells to migrate. T21/DP107, on the other hand is an efficient agonist on both FPR and FPRL1, although the efficacy for FPR expressing cells was much lower than for FPRL1 expressing cells. In the following, we discuss in greater detail our experiments and findings that prove that T20/DP178 and T21/DP107 modulate an inflammatory response.

T20/DP178 and T21/DP107 Modulate an Inflammatory Response

The findings above demonstrate that different gp41 domains activate multiple chemoattractant receptors which are not used by HIV-1 as fusion cofactors but play an important role in the recruitment and activation of phagocytic cells thus promoting host inflammatory and innate immune responses. (Dimitrov and Broder, *HIV and Membrane Receptors, HIV and membrane fusion.* Medical Intelligence Unit, Landes Bioscience, Austin, Tex. (1997); Berger, *AIDS* 11, Suppl A: S3 (1997); Prossnitz et al., *Pharmacol Ther* 74:73 (1997); Murphy and McDermott, *J. Biol. Chem.* 266: 12560 (1991); Murphy, *Annu. Rev. Immuno.* 12: 593 (1994); Murphy, *The N-formyl peptide chemotactic receptors, Chemoattractant ligands and their receptors.* CRC Press, Boca Raton, p. 269 (1996); and Gao et al., *J. Exp. Med.* 180: 2191 (1994)). Notably, the experiments above provide novel evidence that HIV-1 envelope gp41 contains domains that interact with a classical non-chemokine chemoattractant receptor on host phagocytes. Although envelope gp41 mediates viral fusion, regions of this protein T20/DP178 and T21/DP107 also interact with FPR members, activate phagocytic cells, induce a Ca$^{++}$ flux, induce cell migration, and thereby up-regulate an inflammatory response. Additionally, we have shown that fragments of T20/DP178 interact with FPR members and act as antagonists which prevent activation of phagocytic cells and induction of cell migration and, thereby, down-regulates an inflammatory response. Further, we contemplate that fragments of T21/DP107 act as antagonists to bind phagocytic cells but not induce cellular signaling.

Leukocyte infiltration at the sites of inflammation in vivo is considered to be based on migration of cells toward a gradient of chemoattractant(s), either derived from microorganisms or the local tissue. The discovery of synthetic N-formyl oligopeptide chemoattractants for phagocytes represented a major advance in the study of leukocyte locomotion. (Schiffmann et al., *Proc. Natl. Acad. Sci. U.S.A.* 72: 1059 (1975)). Several natural N-formyl peptide chemoattractants, including the prototype fMLP, have since been purified from bacterial supernatants, providing evidence that they are biologically relevant ligands for FPR. Mitochondrial proteins are also N-formylated and are chemotactic for neutrophils bearing FPR, representing a possible source of endogenous agonist(s). (Carp, H., *J. Exp. Med.* 155: 264 (1982)). Although early studies indicated that the N-formyl group was essential for optimal agonist potency, more recent studies have shown that non-formylated peptides may also bind the FPR and activate phagocyte function. (Prossnitz et al., *Pharmacol Ther* 74:73 (1997); Murphy, *The N-formyl peptide chemotactic receptors, Chemoattractant ligands and their receptors.* CRC Press, Boca Raton, p. 269 (1996); Freer et al., *Biochemistry* 21: 257 (1982); Prossnitz et al., *Pharmacol Ther* 74:73 (1997); Murphy, *The N-formyl peptide chemotactic receptors, Chemoattractant ligands and their receptors.* CRC Press, Boca Raton, p. 269 (1996); and Gao et al., *J. Exp. Med.* 180: 2191 (1994)).

The synthetic pentapeptide Met-Ile-Leu-Phe-Phe (SEQ ID NO:1), either N-formylated or N-acetylated, for example, is more potent than the parental prototype fMLP in the induction of $Ca^{++}$ flux in human neutrophils. (Gao et al., *J. Exp. Med.* 180: 2191 (1994)). Amino terminal urea-substituted and carbonate-modified peptides are also potent agonists for the FPR. (Higgins et al., *J. Med. Chem.* 39: 1013 (1996); and Derian et al., *Biochemistry* 35: 1265 (1996)). In addition, altering the amino acid composition of these peptides can convert an agonist to an antagonist. In the experiments presented above, the non-N-formylated T20/DP178 does not bear any sequence identity to the reported FPR agonists yet showed potent FPR stimulating activity. Furthermore, the non-acetylated T20/DP178 was equally active as the acetylated form, proving that acetylation is not a requirement for T20/DP178 to stimulate FPR. Structural analysis of FPR revealed that the binding pocket of this receptor is able to accommodate an amino terminal group larger than a formyl group. (Higgins et al., *J. Med. Chem.* 39: 1013 (1996); and Derian et al., *Biochemistry* 35: 1265 (1996)). A large binding pocket would enable many different ligands to bind to this receptor, and we have demonstrated that truncated mutants—deletion of several amino acids from the N-terminus of T20/DP178—yielded antagonists of FPR, some of which still maintained significant anti-HIV-1 fusion efficacy. (Lawless et al., *Biochemistry* 35: 13697 (1996)). Thus, the spectrum of interaction between FPR and its agonists or antagonists is much broader than expected.

The binding of FPR by agonists, including fMLP, results in a cascade of G protein-mediated signaling events leading to phagocytic cell adhesion, chemotaxis, release of oxygen intermediates, enhanced phagocytosis and bacterial killing, as well as MAP kinase activation and gene transcription. (Krump et al., *J Biol Chem* 272:937 (1997); Prossnitz et al., *Pharmacol Ther* 74:73 (1997); Murphy, *Annu. Rev. Immuno.* 12: 593 (1994); and Murphy, *The N-formyl peptide chemotactic receptors Chemoattractant ligands and their receptors.* CRC Press, Boca Raton, p. 269 (1996)). Cell activation through FPR can also lead to desensitization of a subsequent cell response to other G-protein receptor ligands, including chemokines presumably by protein kinase mediated receptor phosphorylation. (Ali et al., *J. Biol. Chem.* 268: 24247 (1993); and Ali et al., *J. Biol. Chem.* 271: 3200 (1996)).

While fMLP is a high affinity agonist for FPR, it interacts with and induces Ca++ flux in FPRL1 only at high concentrations. (Gao and M. Murphy, *J. Biol. Chem.* 268: 25395 (1993); Ye et al., *Biochem. Biophys. Res. Commun.* 184: 582 (1992); and Durstin et al., *Biochem. Biophys. Res. Commun.* 201: 174 (1994)). In our study, fMLP failed to induce significant migration of FPRL1/293 cells at a concentrations as high as 50 $\mu$M (5×10–5 M), proving that fMLP is not a full agonist for FPRL1. In contrast, T21/DP107, although also activating both FPR and FPRL1 receptors, showed a much higher efficacy on FPRL1 and induces migration of FPRL1/293 cells at nM concentrations. Thus, compared to fMLP, T21/DP107 is a functionally more relevant agonist for FPRL1. It should be understood that T21/DP107 does not bear any significant sequence homology to fMLP. Although FPRL1 is mainly expressed in monocytes and neutrophils, cells other than phagocytes such as hepatocytes have also been shown to express FPRL1. (Prossnitz and Ye, *Pharmacol. Ther.* 74: 73 (1997)). Recently, the expression of this receptor has been reported to be highly inducible in epithelial cells by specific cytokines such as IL-13 and IFN-γ. (Gronert et al., *J. Exp. Med.* 187: 1285 (1998)). Therefore, FPRL1 may play an important role in inflammatory and immunological responses in many different types of human cells.

In addition to peptide and protein agonists, a lipid metabolite lipoxin A4 (LXA4) has been reported to be a high affinity ligand and potent agonist for FPRL1 (also termed LXA4R). (Fiore et al., *J. Exp. Med.* 180: 253 (1994)). LXA4 is an eicosanoid generated during a number of host reactions such as inflammation, thrombosis and atherosclerosis, and was initially discovered as an inhibitor of immune responses. (Reviewed in Samuelsson et al., *Science.* 237: 1171 (1987)). LXA4 was subsequently reported to inhibit neutrophil chemotaxis and transepithelial migration induced by chemotactic agents (Colgan et al., *J. Clin. Invest.* 92: 75 (1993) and Lee et al., *Biochem. Biophys. Res. Commun.* 180: 1416 (1991)). LXA4 bound to CHO cells transfected with FPRL1 increased GTPase activity and the release of esterified arachidonate. (Fiore et al., *J. Exp. Med.* 180: 253 (1994)). Thus, LXA4 has been proposed to be an endogenously produced ligand for FPRL1. (Fiore et al., *J. Exp. Med.* 180: 253 (1994) and Takano et al., *J. Exp. Med.* 185: 1693 (1997)). Although LXA4 has not been documented to induce $Ca^{++}$ mobilization in neutrophils or FPRL1 transfected cells, it was reported to induce $Ca^{++}$ flux and chemotaxis in monocytes. (Fiore et al., *J. Exp. Med.* 180: 253 (1994); Romano et al., *J. Immunol.* 157: 2149 (1994); and Maddox et al., *J. Biol. Chem.* 272: 6972 (1997)). In our experiments, however, we did not detect significant induction of $Ca^{++}$ flux or chemotaxis in FPRL1/293 cells using commercially available LXA4 (Biomol, Plymouth Meeting, Pa.), nor did we observe inhibition of T21/DP107 signaling using LXA4 in either phagocytes or FPRL1/293 cells.

Although the signal transduction pathways mediated by FPRL1 has not been extensively studied, the high level of homology to FPR, sensitivity to pertussis toxin, and mediation of potent phagocyte migration and activation by its agonists provides substantial evidence that FPRL1 and FPR share many signal transduction steps following activation. The binding of FPR by agonists results in a G protein-mediated signaling cascade leading to cell adhesion, chemotaxis, release of oxygen intermediates, enhanced phagocytosis and bacterial killing, as well as MAP kinase activation leading to gene transcription. (Prossnitz and Ye, *Pharmacol. Ther.* 74: 73 (1997); Murphy, *The N-formyl peptide chemotactic receptors, Chemoattractant ligands and their receptors*. CRC Press, Boca Raton, p. 269 (1996)). Activation by fMLP can also lead to heterologous desensitization of the subsequent cell response to other G-protein receptor ligands including chemokines. (Ali et al., *J. Biol. Chem.* 268: 24247 (1993); and Ali et al., *J. Biol. Chem.* 268: 24247 (1993)). We contemplate that activation of FPRL1 also activates signaling events that cause desensitization of other G-protein coupled chemotactic receptors.

It has been reported that gp41 antigen could be detected in brain tissues of AIDS dementia (Adamson et. al., *Science* 274: 1917 (1996)), and antibodies recognizing various epitopes of gp41 appear at early stages of HIV-1 infection. (Nara et al., *FASEB J.* 5: 2437 (1991)). In fact, we found that both synthetic T21/DP107 and T20/DP178 epitopes of gp41 were recognized by sera from AIDS patients by immunoblotting proving that gp41 and its epitopes are accessible to host cells including antigen presenting cells. Therefore, although the receptors for FPR members are not used by HIV-1 for fusion, we contemplate that they participate in the regulation of host innate immune and inflammatory responses seen in AIDS patients characterized by an initial stimulation of immune system in the early stage of the disease followed by progressive immunosuppression.

In the discussion below, we describe several methods of molecular modeling and rational drug design for the identification of homologous ligands which interact with FPR members and thereby modulate an inflammatory response.

Methods of Rational Drug Design

In some embodiments, search programs are employed to compare regions of T20/DP178, T21/DP107, and fragments thereof which modulate an inflammatory response with other molecules, such as peptides, peptidomimetics, and chemicals, so that therapeutic interactions of new molecules (e.g., ligands for FPR members) can be predicted. (Schneider, *Genetic Engineering News* December: page 20 (1998), Tempczyk et al., *Molecular Simulations Inc. Solutions* April (1997) and Butenhof, *Molecular Simulations Inc. Case Notes* (August 1998)). This process is referred to as "rational drug design". One goal of rational drug design is to produce structural or functional analogs of biologically active polypeptides of interest or of small molecules with which they interact (e.g., agonists, antagonists, null compounds) in order to fashion drugs which are, for example, more or less potent forms of the ligand. (See, e.g., Hodgson, *Bio. Technology* 9:19–21 (1991)). An example of rational drug design is the development of HIV protease inhibitors. (Erickson et al., *Science* 249:527–533 (1990)).

By starting with the sequence or protein models of T20/DP178, T21/DP107, and/or fragments thereof ligands having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides are aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{length of the longer sequence within the matched span} + \text{number of gaps introduced into the longer sequence in order to align the two sequences}]} \times 100$$

Accordingly, the protein sequence corresponding to T20/DP178 and T21/DP107 is compared to known sequences on a protein basis. Protein sequences corresponding to T20/DP178 and T21/DP107 are compared, for example, to known amino acid sequences found in Swissprot release 35, PIR release 53 and Genpept release 108 public databases using BLASTP with the parameter W=8 and allowing a maximum of 10 matches. In addition, the protein sequences encoding T20/DP178 and T21/DP107 are compared to publicly known amino acid sequences of Swissprot using BLASTX with the parameter E=0.001. The candidate ligands desirably have at least 50% homology and preferably have 60% or 70% or 80% or 90% or greater homology to T20/DP178 and T21/DP107. The candidate ligands may have the following degrees of homology to T20/DP178 and T21/DP107, for example: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. The candidate ligands having greater than or equal to 50% homology are identified and are subsequently examined using the functional assays described herein. Candidate ligands which can interact with an FPR member and thereby modulate an inflammatory response are, thus, identified.

Additionally, a search program is used to compare the three-dimensional structure of T20/DP178 and T21/DP107 with other known sequences so as to identify candidate ligands which can interact with an FPR member and thereby modulate an inflammatory response. In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure may be determined through the use of techniques of neutron diffraction, or by nuclear magnetic resonance (NMR). (See, e.g., Moore, W. J., Physical Chemistry, 4$^{th}$ Edition, Prentice-Hall, N.J. (1972)).

Alternatively, the protein model embodiments of the present invention are constructed using computer-based protein modeling techniques. By one approach, the protein folding problem is solved by finding target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of a ligand of interest. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON which constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins: Structure, Function, and Genetics, Supplement 1:38–42 (1997)).

In one approach, a three-dimensional structure of a ligand of interest (e.g., T20/DP178, T21/DP107, and/or fragments thereof) is determined by x-ray crystallography, NMR, or neutron diffraction and computer modeling, as described above. Useful protein models of the ligand may also be gained by computer modeling alone. Combinatorial chemistry is then employed to design derivatives of the ligand of interest based on the three-dimensional models. The chemoattraction, cell migration, $Ca^{++}$ mobilization, and ligand binding competition assays, as well as, the immunohistochemistry and other assays described above (referred to collectively as "FPR class characterization assays") are then performed on the derivative ligands and groups of ligands based on the potency of inflammatory response are identified and recorded on a computer readable media. Further cycles of modeling and FPR class characterization assays are employed to more narrowly define the parameters needed in a ligand which elicits a desired response.

In addition, a ligand peptide of interest (e.g., T20/DP178, T21/DP107, and fragments thereof) can be analyzed by an alanine scan (Wells, Methods in Enzymol. 202:390–411 (1991)). In this technique, an amino acid residue is replaced by alanine, and its affect on the peptide's activity is measured by functional assays, such as the FPR class characterization assays described herein. Each of the amino acid residues of the peptide is analyzed in this manner and the regions important for a specific inflammatory response are identified. Subsequently, these functionally important regions are recorded on a computer readable medium, stored in a first database in a computer system, and a search program is employed to generate protein models of the functionally important regions. Once protein models of the functionally important regions have been generated, a second database comprising one or more libraries having peptides, chemicals, peptidomimetics and other agents is accessed by a search program and individual agents are compared to the protein models to identify agents which comprise homologous regions or domains which resemble the identified functionally important regions. Agents identified by the approach above are then tested in the FPR class characterization assays and are used to construct multimeric agents and/or are incorporated into pharmaceuticals, as detailed below.

In another embodiment, computer modeling and the sequence-to-structure-to-function paradigm is exploited to identify more ligands which modulate an inflammatory response through an FPR member. By this approach, first the structure of a protein ligand having a known response in a FPR class characterization assay (e.g., T20/DP178, T21DP107, and fragments thereof) is determined from its sequence using a threading algorithm, which aligns the sequence to the best matching structure in a structural database. Next, the protein's active site (i.e., the site important for a desired response in the FPR class characterization assay) is identified and a "fuzzy functional form" (FFF)—a three-dimensional descriptor of the active site of a protein—is created. (See e.g., Fetrow et al., J. Mol. Biol. 282:703–711 (1998) and Fetrow and Skolnick, J. Mol. Biol. 281: 949–968 (1998)).

The FFFs are built by itteratively superimposing the protein geometries from a series of functionally related proteins with known structures. The FFFs are not overly specific, however, and the degree to which the descriptors can be relaxed is explored. In essence, conserved and functionally important residues for a desired inflammatory response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained.

By using this computational protocol, genome sequence data bases such as maintained by various organizations including: www.tigr.org/tdb; www.genetics.wisc.edu; www.stanford.edu/~ball; hiv-web.lanl.gov; www.ncbi.nlm.nih.gov; www.ebi.ac.uk; pasteur.fr/other/biology; and www-genome.wi.mit.edu, can be rapidly screened for specific protein active sites and for identification of the residues at those active sites which resemble a desired ligand. Several other groups have developed databases of short sequence patterns or motifs designed to identify a given function or activity of a protein. These databases, notably Prosite (expasy.hcuge.ch/sprot/prosite.html; Blocks (www.blocks.fhcrc.org); and prints (www.biochem.ucl.ac.uk/bsm/dbbrowser/PRINTS/PRINTS.html), use short stretches of sequence information to identify sequence patterns that are specific for a given function; thus they avoid the problems arising from the necessity of matching entire sequences. In this manner, new ligands are rationally selected for further identification by FPR class characterization assays, as described above. Rounds or cycles of functional assays on the molecules and derivatives thereof and further FFF refinement and database searching allows an investigator to more narrowly define classes of ligands which produce desirable inflammatory responses.

Many computer programs and databases may be used with embodiments of the invention to identify agents which modulate an inflammatory response. The following list is intended not to limit the invention but to provide guidance to programs and databases which are useful with the approaches discussed above. The programs and databases which may be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA,* 85: 2444 (1988)), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Libraries of information on ligands with their corresponding inflammatory response can be generated by performing the rational drug design approaches above in conjunction with FPR class characterization assays. A record of the results for each ligand is generated and groups of ligands are identified and stored on a computer readable media. Databases of this information would be valuable to investigators and clinicians for selecting the type of ligand-based pharmaceutical to treat or elicit a particular inflammatory response. Preferable libraries are created by performing the assays above on the ligands T20/DP178, T21/DP107, and fragments thereof.

In several embodiments of the present invention, T20/DP178, T21/DP107, and fragments thereof are incorporated into biotechnological tools and pharmaceuticals for therapeutic and prophylactic application. Preferably, the peptides T20/DP178, T21/DP107, and fragments thereof correspond to the sequences listed in Example 1 and Example 2. The peptides T20/DP178, T21/DP107, and fragments thereof can be longer or shorter than the peptides listed in Example 1 and 2, however, and desirable peptides are between three amino acids and 100 amino acids in length and have at least some portion of the sequence which corresponds to the peptides T20/DP178 and T21/DP107. Additionally, peptidomimetics which resemble the peptides T201DP178, T21/DP107, and fragments thereof or peptides of between three and 100 amino acids having sequence which corresponds to the peptides T20/DP178 and T21/DP107, are embodiments of the present invention. For example, an oligopeptide for use in aspects of the present invention may have three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty nine, or forty or fifty or sixty or seventy or eighty or ninety or one-hundred amino acids. Similarly, peptidomimetics of the present invention may have structures that resemble three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty nine, or forty or fifty or sixty or seventy or eighty or ninety or one-hundred amino acids.

Peptides for use in aspects of the present invention may also be modified, e.g., the peptides may have substituents not normally found on a peptide or the peptides may have substituents that are normally found on the peptide but are incorporated at regions of the peptide that are not normal. The peptides for use in aspects of the present invention may be acetylated, acylated, or aminated, for example. Substituents which may be included on the peptide so as to modify it include, but are not limited to, H, alkyl, aryl, alkenyl, alkynl, aromatic, ether, ester, unsubstituted or substituted amine, amide, halogen or unsubstituted or substituted sulfonyl or a 5 or 6 member aliphatic or aromatic ring. As used throughout this disclosure, the term "peptide agent" refers to a modified or unmodified peptide and a chemical or a peptidomimetic which structurally (three-dimensionally or two-dimensionally) resembles a modified or unmodified T20/DP178, T21/DP107, and/or a fragment thereof Peptide agents include, but are not limited to, ligands identified by the methods of rational drug design detailed above by virtue of structural relatedness to T20/DP178, T21/DP107, or a fragment of T20/DP178, T21/DP107, or a peptidomimetic which resembles T20/DP178, T21/DP107, and a fragment thereof.

The peptides T20/DP178, T21/DP107, and fragments or derivatives thereof, include but are not limited to, those containing as a primary amino acid sequence all or part of the amino acid sequence substantially as depicted in Examples 1 and 2 including altered sequences in which functionally equivalent amino acid residues are substituted for residues within the sequence resulting in a silent change. Accordingly, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine. In other aspects of the invention, T20/DP178, T21/DP107, and fragments or derivatives thereof, which are differentially modified during or after translation, e.g., by phosphorylation, glycosylation, cross-linking, acylation, proteolytic cleavage, linkage to an antibody molecule, membrane molecule, or other ligand, are contemplated. (Ferguson et al., *Ann. Rev. Biochem.* 57:285–320 (1988)).

```
Carboxy truncations of T20/DP178 include:

-YTS-

-YTSL-                                         SEQ ID NO:2

-YTSLI-                                        SEQ ID NO:3

-YTSLIH-                                       SEQ ID NO:4

-YTSLIHS-                                      SEQ TD NO:5

-YTSLIHSL-                                     SEQ ID NO:6

-YTSLIHSLI-                                    SEQ ID NO:7

-YTSLIHSLIE-                                   SEQ ID NO:8

-YTSLIHSLIEE-                                  SEQ ID NO:9

-YTSLIHSLIEES-                                 SEQ ID NO:10

-YTSLIHSLIEESQ-                                SEQ ID NO:11

-YTSLIHSLIEESQN-                               SEQ ID NO:12

-YTSLIHSLIEESQNQ-                              SEQ ID NO:13

-YTSLIHSLIEESQNQQ-                             SEQ ID NO:14

-YTSLIHSLIEESQNQQE-                            SEQ ID NO:15

-YTSLIHSLIEESQNQQEK-                           SEQ ID NO:16

-YTSLIHSLIEESQNQQEKN-                          SEQ ID NO:17

-YTSLIHSLIEESQNQQEKNE-                         SEQ ID NO:18

-YTSLTHSLIEESQNQQEKNEQ-                        SEQ ID NO:19

-YTSLIHSLIEESQNQQEKNEQE-                       SEQ ID NO:20

-YTSLIHSLIEESQNQQERNEQEL-                      SEQ ID NO:21

-YTSLIHSLIEESQNQQEKNEQELL-                     SEQ ID NO:22

-YTSLIHSLIEESQNQQEKNEQELLE-                    SEQ ID NO:23

-YTSLIHSLIEESQNQQEKNEQELLEL-                   SEQ ID NO:24

-YTSLIHSLIEESQNQQEKNEQELLELD-                  SEQ ID NO:25

-YTSLIHSLIEESQNQQEKNEQELLELDK-                 SEQ ID NO:26

-YTSLIHSLIEESQNQQEKNEQELLELDKW-                SEQ ID NO:27

-YTSLIHSLIEESQNQQEKNEQELLELDKWA-               SEQ ID NO:28

-YTSLIHSLIEESQNQQEKNEQELLELDKWAS-              SEQ ID NO:29

-YTSLIHSLIEESQNQQEKNEQELLELDKWASL-             SEQ ID NO:30

-YTSLIHSLIEESQNQQEKNEQELLELDKWASLW-            SEQ ID NO:31

-YTSLIHSLIEESQNQQEKNEQELLELDKWASLWN-           SEQ ID NO:32

-YTSLIHSLIEESQNQQEKNEQELLELDKWASLWNW-          SEQ ID NO:33

-YTSLIHSLIEESQNQQEKNEQELLELDKWASLWNWF-         SEQ ID NO:34
```

-continued

Amino truncations of T20/DP17S include:

-NWF-

-WNWF-                                                              SEQ ID NO:35

-LWNWF-                                                             SEQ ID NO:36

-SLWNWF-                                                            SEQ ID NO:37

-ASLWNWF-                                                           SEQ ID NO:38

-WASLWNWF-                                                          SEQ ID NO:39

-KWASLWNWF-                                                         SEQ ID NO:40

-DKWASLWNWF-                                                        SEQ ID NO:41

-LDKWASLWNWF-                                                       SEQ ID NO:42

-ELDKWASLWNWF-                                                      SEQ ID NO:43

-LELDKWASLWNWF-                                                     SEQ ID NO:44

-LLELDKWASLWNWF-                                                    SEQ ID NO:45

-ELLELDKWASLWNWF-                                                   SEQ ID NO:46

-QELLELDKWASLWNWF-                                                  SEQ ID NO:47

-EQELLELDKWASLWNWF-                                                 SEQ ID NO:48

-NEQELLELDKWASLWNWF-                                                SEQ ID NO:49

-KNEQELLELDKWASLWNWF-                                               SEQ ID NO:50

-EKNEQELLELDKWASLWNWF-                                              SEQ ID NO:51

-QEKNEQELLELDKWASLWNWF-                                             SEQ ID NO:52

-QQEKNEQELLELDKWASLWNWF-                                            SEQ ID NO:53

-NQQEKNEQELLELDKWASLWNWF-                                           SEQ ID NO:54

-QNQQEKNEQELLELDKWASLWNWF-                                          SEQ ID NO:55

-SQNQQEKNEQELLELDKWASLWNWF-                                         SEQ ID NO:56

-ESQNQQEKNEQELLELDKWASLWNWF-                                        SEQ ID NO:57

-EESQNQQEKNEQELLELDKWASLWNWF-                                       SEQ ID NO:58

-IEESQNQQEKNEQELLELDKWASLWNWF-                                      SEQ ID NO:59

-LIEESQNQQEKNEQELLELDKWASLWNWF-                                     SEQ ID NO:60

-SLIEESQNQQEKNEQELLELDKWASLWNWF-                                    SEQ ID NO:61

-HSLIEESQNQQEKNEQELLELDKWASLWNWF-                                   SEQ ID NO:62

-IHSLIEESQNQQEKNEQELLELDKWASLWNWF-                                  SEQ ID NO:63

-LIHSLIEESQNQQEKNEQELLELDKWASLWNWF-                                 SEQ ID NO:64

-SLIHSLIEESQNQQEKNEQELLELDKWASLWNWF-                                SEQ ID NO:65

-TSLIHSLIEESQNQQEKNEQELLELDKWASLWNWF-                               SEQ ID NO:66

-YTSLIHSLIEESQNQQEKNEQELLELDKWASLWNWF-                              SEQ ID NO:67

Internal truncations of T20/DP 178 include:

-TSL- and -TSL-5-36 wherein
5-36 means I, IH, IHS, . . . IHSLIEESQNQQEKNEQELLELDKWASLWNWF-       SEQ ID NO:68

-SLI- and -SLI-6-36 wherein
6-36 means H, HS, HSL, . . . HSLIEESQNQQEKNEQELLELDKWASLWNWF-        SEQ ID NO:69

-LIH- and -LIH-7-36 wherein

-continued

```
7-36 means S, SL, SLI, . . . SLIEESQNQQEKNEQELLELDKWASLWNWF-        SEQ ID NO:70

-IHS- and -IHS-8-36 wherein
8-36 means L, LI, LIE, . . . LIEESQNQQEKNEQELLELDKWASLWNWF-         SEQ ID NO:71

-HSL- and -HSL-9-36 wherein
9-36 means I, IE, IEE, . . . IEESQNQQEKNEQELLELDKWASLWNWF-          SEQ ID NO:72

-SLI- and -SLI-10-36 wherein
10-36 means E, EE, EES, . . . EESQNQQEKNEQELLELDKWASLWNWF-          SEQ ID NO:73

-LIE- and -LIE-11-36 wherein
11-36 means E, ES, ESQ, . . . ESQNQQEKNEQELLELDKWASLWNWF-           SEQ ID NO:74

-IEE- and -IEE-12-36 wherein
12-36 means S, SQ, SQN, . . . SQNQQEKNEQELLELDKWASLWNWF-            SEQ ID NO:75

-EES- and -EES-13-36 wherein
13-36 means Q, QN, QNQ, . . . QNQQEKNEQELLELDKWASLWNWF-             SEQ ID NO:76

-ESQ- and -ESQ-14-36 wherein
14-36 means N, NQ, NQQ, . . . NQQEKNEQELLELDKWASLWNWF-              SEQ ID NO:77

-SQN- and -SQN-15-36 wherein
15-36 means Q, QQ, QQE, . . . QQEKNEQELLELDKWASLWNWF-               SEQ ID NO:78

-QNQ- and -QNQ-16-36 wherein
16-36 means Q, QE, QEK, . . . QEKNEQELLELDKWASLWNWF-                SEQ ID NO:79

-NQQ- and -NQQ-17-36 wherein
17-36 means E, EK, EKN, . . . EKNEQELLELDKWASLWNWF-                 SEQ ID NO:80

-QQE- and -QQE-18-36 wherein
18-36 means K, KN, KNE, . . . KNEQELLELDKWASLWNWF-                  SEQ ID NO:81

-QEK- and -QEK-19-36 wherein
19-36 means N, NE, NEQ, . . . NEQELLELDKWASLWNWF-                   SEQ ID NO:82

-EKN- and -EKN-20-36 wherein
20-36 means E, EQ, EQE, . . . EQELLELDKWASLWNWF-                    SEQ ID NO:83

-KNE- and -KNE-21-36 wherein
21-36 means Q, QE, QEL, . . . QELLELDKWASLWNWF-                     SEQ ID NO:84

-NEQ- and -NEQ-22-36 wherein
22-36 means E, EL, ELL, . . . ELLELDKWASLWNWF-                      SEQ ID NO:85

-EQE- and -EQE-23-36 wherein
23-36 means L, LL, LLE, . . . LLELDKWASLWNWF-                       SEQ ID NO:86

-QEL- and -QEL-24-36 wherein
24-36 means L, LE, LEL, . . . LELDKWASLWNWF-                        SEQ ID NO:87

-ELL- and -ELL-25-36 wherein
25-36 means E, EL, ELD, . . . ELDKWASLWNWF-                         SEQ ID NO:88

-LLE- and -LLE-26-36 wherein
26-36 means L, LD, LDK, . . . LDKWASLWNWF-                          SEQ ID NO:89

-LEL- and -LEL-27-36 wherein
27-36 means D, DK, DKW, . . . DKWASLWNWF-                           SEQ ID NO:90

-ELD- and -ELD-28-36 wherein
28-36 means K, KW, KWA, . . . KWASLWNWF-                            SEQ ID NO:91

-LDK- and -LDK-29-36 wherein
29-36 means W, WA, WAS, . . . WASLWNWF-                             SEQ ID NO:92

-DKW- and -DKW-30-36 wherein
30-36 means A, AS, ASL, . . . ASLWNWF-                              SEQ ID NO:93

-KWA- and -KWA-31-36 wherein
31-36 means S, SL, SLW, . . . SLWNWF-                               SEQ ID NO:94

-WAS- and -WAS-32-36 wherein
32-36 means L, LW, LWN, . . . LWNWF-                                SEQ ID NO:95

-ASL- and -ASL-33-36 wherein
33-36 means W, WN, WNW, . . . WNWF-                                 SEQ ID NO:96
```

-SLW- and -SLW-34-36 wherein
34-36 means N, NW, or NWF-

-LWN- and -LWN-35-36 wherein
35-36 means W or WF-
-WNW- and -WNWF- SEQ ID NO:96

Carboxy truncations of T21/DP107 include:

-NNL

-NNLL- SEQ ID NO:97

-NNLLR- SEQ ID NO:98

-NNLLRA- SEQ ID NO:99

-NNLLRAI- SEQ ID NO:100

-NNLLRAIE- SEQ ID NO:101

-NNLLRAIEA- SEQ ID NO:102

-NNLLRAIEAQ- SEQ ID NO:103

-NNLLRAIEAQQ- SEQ ID NO:104

-NNLLRAIEAQQH- SEQ ID NO:105

-NNLLRAIEAQQHL- SEQ ID NO:106

-MNLLRAIEAQQHLL- SEQ ID NO:107

-NNLLRAIEAQQHLLQ- SEQ ID NO:108

-NNLLRAIEAQQHLLQL- SEQ ID NO:109

-NNLLRAIEAQQHLLQLT- SEQ ID NO:110

-NNLLRAIEAQQHLLQLTV- SEQ ID NO:111

-NNLLRAIEAQQHLLQLTVW- SEQ ID NO:112

-NNLLRAIEAQQHLLQLTVWG- SEQ ID NO:113

-NNLLRAIEAQQHLLQLTVWGI- SEQ ID NO:114

-NNLLRAIEAQQHLLQLTVWGIK- SEQ ID NO:115

-NNLLRAIEAQQHLLQLTVWGIKQ- SEQ ID NO:116

-NNLLRAIEAQQHLLQLTVWGIKQL- SEQ ID NO:117

-NNLLRAIEAQQHLLQLTVWGIKQLQ- SEQ ID NO:118

-NNLLRAIEAQQHLLQLTVWGIKQLQA- SEQ ID NO:119

-NNLLRAIEAQQHLLQLTVWGIKQLQAR- SEQ ID NO:120

-MNLLRAIEAQQHLLQLTVWGIKQLQARI- SEQ ID NO:121

-NNLLRAIEAQQHLLQLTVWGIKQLQARIL- SEQ ID NO:122

-NNLLRAIEAQQHLLQLTVWGIKQLQARILA- SEQ ID NO:123

-NNLLRAIEAQQHLLQLTVWGIKQLQARILAV- SEQ ID NO:124

-NNLLRAIEAQQHLLQLTVWGIKQLQARILAVE- SEQ ID NO:125

-NNLLRAIEAQQHLLQLTVWGIKQLQARILAVER- SEQ ID NO:126

-NNLLRAIEAQQHLLQLTVWGIKQLQARILAVERY- SEQ ID NO:127

-NNLLRAIEAQQHLLQLTVWGIKQLQARILAVERYL- SEQ ID NO:128

-NNLLRAIEAQQHLLQLTVWGIKQLQARILAVERYLK- SEQ ID NO:129

-NNLLRAIEAQQHLLQLTVWGIKQLQARILAVERYLKD- SEQ ID NO:130

-NNLLRAIEAQQHLLQLTVWGIKQLQARILAVERYLKDQ- SEQ ID NO:203

-continued

Amino truncations of T21/DP107 include:

-KDQ

-LKDQ-                                                              SEQ ID NO:131

-YLKDQ-                                                             SEQ ID NO:132

-RYLKDQ-                                                            SEQ ID NO:133

-ERYLKDQ-                                                           SEQ ID NO:134

-VERYLKDQ-                                                          SEQ ID NO:135

-AVERYLKDQ-                                                         SEQ ID NO:136

-LAVERYLKDQ-                                                        SEQ ID NO:137

-ILAVERYLKDQ-                                                       SEQ ID NO:138

-RILAVERYLKDQ-                                                      SEQ ID NO:139

-ARILAVERYLKDQ-                                                     SEQ ID NO:140

-QARILAVERYLKDQ-                                                    SEQ ID NO:141

-LQARILAVERYLKDQ-                                                   SEQ ID NO:142

-QLQARILAVERYLKDQ-                                                  SEQ ID NO:143

-KQLQARILAVERYLKDQ-                                                 SEQ ID NO:144

-IKQLQARILAVERYLKDQ-                                                SEQ ID NO:145

-GIKQLQARILAVERYLKDQ-                                               SEQ ID NO:146

-WGIKQLQARILAVERYLKDQ-                                              SEQ ID NO:147

-VWGIKQLQARILAVERYLKDQ-                                             SEQ ID NO:148

-TVWGIKQLQARILAVERYLKDQ-                                            SEQ ID NO:149

-LTVWGIKQLQARILAVERYLKDQ-                                           SEQ ID NO:150

-QLTVWGIKQLQARILAVERYLKDQ-                                          SEQ ID NO:151

-LQLTVWGIKQLQARILAVERYLKDQ-                                         SEQ ID NO:152

-LLQLTVWGIKQLQARILAVERYLKDQ-                                        SEQ ID NO:153

-HLLQLTVWGIKQLQARILAVERYLKDQ-                                       SEQ ID NO:154

-QHLLQLTVWGIKQLQARILAVERYLKDQ-                                      SEQ ID NO:155

-QQHLLQLTVWGIKQLQARILAVERYLKDQ-                                     SEQ ID NO:156

-AQQHLLQLTVWGIKQLQARILAVERYLKDQ-                                    SEQ ID NO:157

-EAQQHLLQLTVWGIKQLQARILAVERYLKDQ-                                   SEQ ID NO:158

-IEAQQHLLQLTVWGIKQLQARILAVERYLKDQ-                                  SEQ ID NO:159

-AIEAQQHLLQLTVWGIKQLQARILAVERYLKDQ-                                 SEQ ID NO:160

-RAIEAQQHLLQLTVWGIKQLQARILAVERYLKDQ-                                SEQ ID NO:161

-LRAIEAQQHLLQLTVWGIKQLQARILAVERYLKDQ-                               SEQ ID NO:162

-LLRAIEAQQHLLQLTVWGIKQLQARILAVERYLKDQ-                              SEQ ID NO:163

-NLLRAIEAQQHLLQLTVWGIKQLQARILAVERYLKDQ-                             SEQ ID NO:164

-NNLLRAIEAQQHLLQLTVWGIKQLQARILAVERYLKDQ-                            SEQ ID NO:165

Internal truncations of T21/DP107 include:

-NLL- and -NLL-5-38 wherein
5-38 means R, RA, RAI, . . . RAIEAQQHLLQLTVWGIKQLQARILAVERYLKDQ-    SEQ ID NO:166

```
                                  -continued
-LLR- and -LLR-6-38 wherein
6-38 means A, AI, AIE, . . .    AIEAQQHLLQLTVWGIKQLQARILAVERYLKDQ-       SEQ ID NO:167

-LRA- and-LRA-7-38 wherein
7-38 means I, IE, IEA, . . .    IEAQQHLLQLTVWGIKQLQARILAVERYLKDQ-        SEQ ID NO:168

-RAI- and -RAI-8-38 wherein
8-38 means E, EA, EAQ, . . .    EAQQHLLQLTVWGIKQLQARILAVERYLKDQ-         SEQ ID NO:169

-AIE- and -AIE-9-38 wherein
9-38 means A, AQ, AQQ, . . .    AQQHLLQLTVWGIKQLQARILAVERYLKDQ-          SEQ ID NO:170

-IEA- and -IEA-10-38 wherein
10-38 means Q, QQ, QQH, . . .   QQHLLQLTVWGIKQLQARILAVERYLKDQ-           SEQ ID NO:171

-EAQ- and -EAQ-11-38 wherein
11-38 means Q, QH, QHL, . . .   QHLLQLTVWGIKQLQARILAVERYLKDQ-            SEQ ID NO:172

-AQQ- and -AQQ-12-38 wherein
12-38 means H, HL, HLL, . . .   HLLQLTVWGIKQLQARILAVERYLKDQ-             SEQ ID NO:173

-QQH- and -QQH-13-38 wherein
13-38 means L, LL, LLQ, . . .   LLQLTVWGIKQLQARILAVERYLKDQ-              SEQ ID NO:174

-QHL- and -QHL-14-38 wherein
14-38 means L, LQ, LQL, . . .   LQLTVWGIKQLQARILAVERYLKDQ-               SEQ ID NO:175

-HLL- and -HLL-15-38 wherein
15-38 means Q, QL, QLT, . . .   QLTVWGIKQLQARILAVERYLKDQ-                SEQ ID NO:176

-LLQ- and -LLQ-16-38 wherein
16-38 means L, LT, LTV, . . .   LTVWGIKQLQARILAVERYLKDQ-                 SEQ ID NO:177

-LQL- and -LQL-17-38 wherein
17-38 means T, TV, TVW, . . .   TVWGIKQLQARILAVERYLKDQ-                  SEQ ID NO:178

-QLT- and -QLT-18-38 wherein
18-38 means V, VW, VWG, . . .   VWGIKQLQARILAVERYLKDQ-                   SEQ ID NO:179

-LTV- and -LTV-19-38 wherein
19-38 means W, WG, WGI, . . .   WGIKQLQARILAVERYLKDQ-                    SEQ ID NO:180

-TVW- and -TVW-20-38 wherein
20-38 means G, GI, GIK, . . .   GIKQLQARILAVERYLKDQ-                     SEQ ID NO:181

-VWG- and -VWG-21-38 wherein
21-38 means I, IK, IKQ, . . .   IKQLQARILAVERYLKDQ-                      SEQ ID NO:182

-WGI- and -WGI-22-38 wherein
22-38 means K, KQ, KQL, . . .   KQLQARILAVERYLKDQ-                       SEQ ID NO:183

-GIK- and -GIK-23-38 wherein
23-38 means Q, QL, QLQ, . . .   QLQARILAVERYLKDQ-                        SEQ ID NO:184

-IKQ- and -IKQ-24-38 wherein
24-38 means L, LQ, LQA, . . .   LQARILAVERYLKDQ-                         SEQ ID NO:185

-KQL- and -KQL-25-38 wherein
25-38 means Q, QA, QAR, . . .   QARILAVERYLKDQ-                          SEQ ID NO:186

-QLQ- and -QLQ-26-38 wherein
26-38 means A, AR, ARI, . . .   ARILAVERYLKDQ-                           SEQ ID NO:187

-LQA- and -LQA-27-38 wherein
27-38 means Q, RI, RIL, . . .   RILAVERYLKDQ-                            SEQ ID NO:188

-QAR- and -QAR-28-38 wherein
28-38 means I, IL, ILA, . . .   ILAVERYLKDQ-                             SEQ ID NO:189

-ARI- and -ARI-29-38 wherein
29-38 means L, LA, LAV, . . .   LAVERYLKDQ-                              SEQ ID NO:190

-RIL- and -RIL-30-38 wherein
30-38 means A, AV, AVE, . . .   AVERYLKDQ-                               SEQ ID NO:191

-ILA- and -ILA-31-38 wherein
31-38 means VE, VE, VER, . . .  VERYLKDQ-                                SEQ ID NO:192

-LAV- and -LAV-32-38 wherein
32-38 means E, ER, ERY, . . .   ERYLKDQ-                                 SEQ ID NO:193
```

```
-AVE- and -AVE-33-38 wherein
33-38 means R, RY, RYL, . . . RYLKDQ-                               SEQ ID NO:194

-VER- and -VER-34-38 wherein
34-38 means Y, YL, YLK, . . . YLKDQ-                                SEQ ID NO:195

-ERY- and -ERY-35-38 wherein
35-38 means L, LK, LKD, . . . LKDQ-                                 SEQ ID NO:196

-RYL- and -RYL-36-38 wherein
36-38 means K, KD, or KDQ-

-YLK- and -YLK-37-38 wherein
37-38 means D or DQ-
LKD- and -LKDQ-                                                     SEQ ID NO:196
```

The invention includes T20/DP178 and fragments having at least one acidic amino acid substitution selected from the group consisting of:

E10Z, E11Z, E17Z, E20Z, E22Z E25Z, D27Z, where Z is an acidic amino acid.

The invention includes T20/DP178 and fragments having at least one basic amino acid substitution selected from the group consisting of:

H6B, K18B, K28B, where B is a basic amino acid.

The invention includes T20/DP178 and fragments having at least one non-polar amino acid substitution selected from the group consisting of:

L4J, I5J L8J, I9J, L23J, L24J, L26J, W29J, A30J, L32J, W33J, W35J, F36J, where J is a non-polar amino acid.

The invention includes T20/DP178 and fragments having at least one uncharged polar amino acid substitution selected from the group consisting of:

Y1U, T2U, S3U, S7U, S12U, Q13U, N14U, Q15U, Q16U, N19U, Q21U, S 31U, N34U, where U is an uncharged polar amino acid.

The invention includes T20/DP178 and fragments having at least one aromatic amino acid substitution selected from the group consisting of:

Y1X, T2X, F36X, where X is an aromatic amino acid.

The invention includes T21/DP107 and fragments having at least one acidic amino acid substitution selected from the group consisting of:

E8Z, E32Z, D37Z, where Z is an acidic amino acid.

The invention includes T21/DP107 and fragments having at least one basic amino acid substitution selected from the group consisting of:

R5B, H12B, K22B, R27B, R33B, K36B, where B is a basic amino acid.

The invention includes T21/DP107 and fragments having at least one non-polar amino acid substitution selected from the group consisting of:

L3J, L4J, A6J, I7J, A9J, L13J, L14J, L16J, V18J, W19J, I21J, L24J, A26J, I28J, L29J, A30J, V31J, L35J, where J is a non-polar amino acid.

The invention includes T21/DP107 and fragments having at least one uncharged polar amino acid substitution selected from the group consisting of:

N1U, N2U, Q10U, Q11U, Q15U, T17U, G20U, Q23U, Q25U, Y34U, Q38U, where U is an uncharged polar amino acid.

The invention includes T21/DP107 and fragments having at least one aromatic amino acid substitution selected from the group consisting of:

T17X, Y34X, where X is an aromatic amino acid.

In many embodiments, we use isolated or purified T20/DP178, T21/DP107, or fragments thereof. The term "isolated" requires that a material be removed from its original environment (e.g., the natural environment if it is naturally occurring). For example, a naturally occurring polynucleotide or polypeptide present in a living cell is not isolated, but the same polynucleotide or polypeptide, separated from some or all of the coexisting materials in the natural system, is isolated.

The term "purified" does not require absolute purity; rather it is intended as a relative definition, with reference to the purity of the material in its natural state. Purification of natural material to at least one order of magnitude, preferably two or three magnitudes, and more preferably four or five orders of magnitude is expressly contemplated.

The term "enriched" means that the concentration of the material is at least about 2, 5, 10, 100, or 1000 times its natural concentration (for example), advantageously 0.01% by weight. Enriched preparations of about 0.5%, 1%, 5%, 10%, and 20% by weight are also contemplated.

In the disclosure below, we teach the preparation of multimeric supports having peptide agents which interact with an FPR member and thereby modulate an inflammatory response. These multimeric supports have many uses including, but not limited to, the manufacture of biotechnological tools and components for pharmaceuticals, therapeutic and prophylactic agents.

Preparation of Multimeric Supports and Multimerized Ligands

In order to be useful as a biotechnological tool or a component to a prophylactic or therapeutic agent, it is desirable to provide the peptide agent in such a form or in such a way that a sufficient affinity for an FPR member is obtained. While a natural monomeric peptide agent (e.g., T20/DP178, T21/DP107, and fragments thereof appearing as discrete units of the peptide each carrying only one binding epitope) is sufficient to interact with an FPR member and thereby modulate an inflammatory response, synthetic ligands or multimeric ligands (e.g., T20/DP178, T21/DP107, and fragments thereof appearing as multiple units of the peptide agent with several binding epitopes) may have far greater ability to interact with an FPR member and thereby modulate an inflammatory response. It should be noted that the term "multimeric" is meant to refer to the presence of more than one unit of a ligand, for example several individual molecules of T20/DP178, T21/DP107, or fragments thereof, as distinguished from the term "multimerized" which refers to the presence of more than one ligand joined as a single discrete unit, for example several molecules of T20/DP178, T211DP107, or fragments thereof joined in tandem.

A multimeric agent (synthetic or natural) which modulates an immune response through an FPR member may be obtained by coupling a T20/DP178, T21/DP107, a fragment of T20/DP178, T21/DP107, or a peptidomimetic which resembles T20/DP178, T21/DP107, or a fragment thereof to a macromolecular support. A "support" may also be termed a carrier, a resin or any macromolecular structure used to attach or immobilize a peptide agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, artificial cells and others. The macromolecular support may have a hydrophobic surface which interacts with a portion of the peptide agent by hydrophobic non-covalent interaction. The hydrophobic surface of the support may also be a polymer such as plastic or any other polymer in which hydrophobic groups have been linked such as polystyrene, polyethylene or polyvinyl. Alternatively, the peptide agent can be covalently bound to carriers including proteins and oligo/polysaccharides (e.g. cellulose, starch, glycogen, chitosane or aminated sepharose). In these later embodiments, a reactive group on the peptide agent, such as a hydroxy or an amino group, may be used to join to a reactive group on the carrier so as to create the covalent bond. The support may also have a charged surface which interacts with the peptide agent. Additionally, the support may have other reactive groups which can be chemically activated so as to attach a peptide agent. For example, cyanogen bromide activated matrices, epoxy activated matrices, thio and thiopropyl gels, nitrophenyl chloroformate and N-hydroxy succinimide chlorformate linkages, and oxirane acrylic supports are common in the art. (Sigma).

The support may also comprise an inorganic carrier such as silicon oxide material (e.g. silica gel, zeolite, diatomaceous earth or aminated glass) to which the peptide agent is covalently linked through a hydroxy, carboxy or amino group and a reactive group on the carrier. Furthermore, in some embodiments, a liposome or lipid bilayer (natural or synthetic) is contemplated as a support and peptide agents are attached to the membrane surface or are incorporated into the membrane by techniques in liposome engineering. By one approach, liposome multimeric supports comprise a peptide agent that is exposed on the surface of the bilayer and a second domain which anchors the peptide agent to the lipid bilayer. The anchor may be constructed of hydrophobic amino acid residues, resembling known transmembrane domains, or may comprise ceramides that are attached to the first domain by conventional techniques.

Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorb® (Johns-Manville Products, Denver Co.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042–1045 (1995)). For some embodiments, a "naked" carrier (i.e., lacking an attached peptide agent) which has the capacity to attach a peptide agent in the body of a subject is administered. By this approach, a "prodrug-type" therapy is envisioned in which the naked carrier is administered separately from the peptide agent and, once both are in the body of the subject, the carrier and the peptide agent are assembled into a multimeric complex.

The insertion of linkers, such as λ linkers, of an appropriate length between the peptide agent and the support are also contemplated so as to encourage greater flexibility of the peptide agent and thereby overcome any steric hindrance which may be presented by the support. The determination of an appropriate length of linker which allows for an optimal desired inflammatory response or lack thereof, can be determined by screening the peptide agents with varying linkers in the assays detailed in the present disclosure.

A composite support comprising more than one type of peptide agent is also envisioned. A "composite support" may be a carrier, a resin, or any macromolecular structure used to attach or immobilize two or more different peptide agents which modulate an inflammatory response through an FPR member. In some embodiments, a liposome or lipid bilayer (natural or synthetic) is contemplated for use in constructing a composite support and peptide agents are attached to the membrane surface or are incorporated into the membrane using techniques in liposome engineering.

As above, the insertion of linkers, such as X linkers, of an appropriate length between the peptide agent and the support is also contemplated so as to encourage greater flexibility in the molecule and thereby overcome any steric hindrance which may occur. The determination of an appropriate length of linker which allows for optimal binding to an FPR member, can be determined by screening the ligands with varying linkers in the assays detailed in the present disclosure.

In other embodiments of the present invention, the multimeric and composite supports discussed above may have attached multimerized ligands so as to create a "multimerized-multimeric support" and a "multimerized-composite support", respectively. A multimerized ligand may, for example, be obtained by coupling two or more peptide agents in tandem using conventional techniques in molecular biology. The multimerized form of the ligand may be advantageous for many applications because of the ability to obtain an agent with a better ability to bind to an FPR member and, thereby, modulate an inflammatory response. We further contemplate that the incorporation of linkers or spacers, such as flexible X linkers, between the individual domains which make-up the multimerized agent may be advantageous. The insertion of λ linkers of an appropriate length between protein binding domains, for example, may encourage greater flexibility in the molecule and can overcome steric hindrance. Similarly, the insertion of linkers between the multimerized ligand and the support may encourage greater flexibility and limit steric hindrance presented by the support. The determination of an appropriate length of linker which allows for optimal binding to a formyl peptide receptor and, thereby, modulates an inflammatory response, can be determined by screening the ligands with varying linkers in the assays detailed in this disclosure.

In preferable embodiments, the various types of supports discussed above are created using T20/DP178, T21/DP107, a fragment of T20/DP178, T21/DP107, or a peptidomimetic which resembles T20/DP178, T21/DP107, or a fragment thereof. The multimeric supports, composite supports, multimerized-multimeric supports, or multimerized-composite supports, collectively referred to as "support-bound agents", are also preferably constructed using T20/DP178, T21/DP107, a fragment of T20/DP178, T21/DP107, or a peptidomimetic which resembles T20/DP178, T21/DP107, or a fragment thereof.

In the discussion below, the present inventor describes several embodiments of the invention which have therapeutic and/or prophylactic application.

Therapeutic and Prophylactic Applications

In the therapeutic and prophylactic embodiments of the present invention, the peptide agents identified as upregulating or downregulating an inflammatory response are incorporated into a pharmaceutical product and are administered to a subject in need. The monomeric and multimeric peptide agents of the invention are suitable for treatment of subjects either as a preventive measure to avoid an inflammatory response or as a therapeutic to treat subjects in need of an anti-inflammatory agent. Additionally, in some prophylactic and/or therapeutic applications, the monomeric and multimeric agents are administered to elicit an inflammatory response.

One contemplated method of making a pharmaceutical involves the selection of a peptide agent which interacts with an FPR member, preferably T20/DP178, T21/DP107, a fragment of T20/DP178, T21/DP107, or a peptidomimetic which resembles T20/DP178, T21/DP107, or a fragment thereof, and incorporating the peptide agent into a pharmaceutical by conventional techniques. The pharmaceuticals of the present invention may be formulated with an adjuvant or may be free and desirable embodiments provide the peptide agent in a support-bound form. Optionally, the peptide agent can be provided in an aggregated form as created, for example, by heating.

In another method of making a pharmaceutical, we envision incorporating a peptide agent selected for its ability to block, inhibit, or prevent an inflammatory response in the FPR class characterization assays described above. Accordingly, a peptide agent which interacts with an FPR member blocks, inhibits, or prevents an inflammatory response is identified and is incorporated into a pharmaceutical by conventional techniques. Preferable peptide agents include, but are not limited to fragments of T20/DP178, T21/DP107, or peptidomimetics which resemble fragments of T20/DP178 or T21/DP107. A novel class of anti-inflammatory agents which bind an FPR member with high avidity but fail to induce an inflammatory response are designed using approaches in rational drug design, described above, and known in the art. These pharmaceuticals are formulated in adjuvant or free and are provided in the form of a support-bound agent, as well. As above, an aggregated form of this embodiment may be created by heating the proteins and can administered to subjects in need.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins. The ligands may also be administered in the form of a support-bound agent or in a pro-drug form which interacts with a support so as to create a support-bound agent in the body of the subject.

In another embodiment, therapeutic agents comprising the peptide agents of the disclosed invention are administered in conjunction with other therapeutic agents which modulate an inflammatory response. It is thus a preferred embodiment of the present invention that the peptide agents be given in combination with non-steroidal anti-inflammatory drugs (NSAID) such as aspirin, ketoprofen, flurbiprofen, ibuprofen, and naproxyn at doses and by methods known to those of skill in the art. Alternatively, it is desirable that the peptide agents be given in combination with agents which induce an inflammatory response such as vaccines, adjuvants, and histimine. Medicaments comprising the peptide agents of the present invention and conventional NSAIDs or conventional agents which induce an inflammatory response are also embodiments of the present invention.

The peptide agents can be administered alone or in combination with other peptides or with other NSAIDs or conventional agents which induce an inflammatory response and can be combined with physiologically acceptable carriers. Further, the manufacture of pharmaceuticals or therapeutic agents which deliver the peptide agent and/or a nucleic acid sequence encoding the peptide agent by several routes is another aspect of the invention. For example, and not by way of limitation, the use of DNA, RNA, and viral vectors having sequence encoding the peptide agent is contemplated. Nucleic acids encoding a desired peptide agent can be administered alone or in combination with peptide agents.

In the following disclosure, doses and methods of administration are provided.

Dosage and Methods of Administration

The effective dose and method of administration of a particular formulation of a peptide agent may vary based on the individual subject and the stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 10 grams, depending upon the route of administration. Guidance as to particular dosages and methods of delivery is provided in the literature. (See U.S. Pat. Nos. 4,657,760; 5,206,344; or 5,225,212.) More specifically, the dosage of the peptide agents of the present invention is one that provides sufficient peptide agent to attain a desirable effect including an up-regulation or a down regulation of an inflammatory response. A constant infusion of the peptide agent can also be provided so as to maintain a stable concentration in the tissues as measured by blood levels.

Routes of administration of the peptide agents include, but are not limited to, topical, transdermal, parenteral, gastrointestinal, transbronchial, and transalveolar. Topical administration is accomplished via a topically applied cream, gel, rinse, etc. containing a peptide agent. Transdermal administration is accomplished by application of a cream, rinse, gel, etc. capable of allowing the peptide agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of peptide agent-containing compounds suitable for topical application include, but not limited to, physiologically acceptable implants, ointments, creams, rinses, and gels. Any liquid, gel, or solid, pharmaceutically acceptable base in which the peptide agents are at least minimally soluble is suitable for topical use in aspects of the present invention. For topical application, there are also employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Compositions of the peptide agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al.

Compositions of the peptide agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the peptides. Additional embodiments for parenteral application include injectable, sterile, oily solutions, suspensions, emulsions, or implants, including suppositories. Ampoules are convenient unit dosages.

Compositions of the peptide agents suitable for transbronchial and transalveolar administration include, but not limited to, various types of aerosols for inhalation. Devices suitable for transbronchial and transalveolar administration of the peptide agents are also embodiments. Such devices include, but are not limited to, atomizers and vaporizers. Many forms of currently available atomizers and vaporizers can be readily adapted to deliver peptide agents.

Compositions of the peptide agents suitable for gastrointestinal administration include, but not limited to, pharmaceutically acceptable powders, tablets, pills, dragees, capsules, drops, or liquids for ingestion and suppositories for rectal administration. A syrup, elixir, or the like can be used wherein a sweetened vehicle is employed.

Sustained, pro-drugs, or directed release compositions can be formulated, e.g., liposomes or those wherein the active compound is protected with differentially degradable coatings, e.g., by microencapsulation, multiple coatings, etc. It is also possible to freeze-dry the ligands and use the lyophilizates obtained, for example, for the preparation of products for injection.

Aspects of the invention also include a coating for medical equipment. Alternatively, the peptides can be impregnated into a polymeric medical device such as catheters, stents and prosthetics. Coatings suitable for use in medical devices can be provided by a powder containing the peptides or by polymeric coating into which the peptides are suspended. Suitable polymeric materials for coatings or devices are those which are physiologically acceptable and through which a therapeutically effective amount of the peptide agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. which is incorporated herein by reference.

It will be appreciated that the actual preferred amounts of active compound in a specific case will vary according to the specific compound being utilized, the particular compositions formulated, the mode of application, and the particular situs and organism being treated. The materials and methods and the experiments presented above are detailed in Su et al., *Blood*, 93(11): 1–10 (1999) and Su et al., *J. Immunol.* 162: (1999) herein incorporated by reference. The example below discloses the materials and methods used to perform the experiments which determined that T20/DP178 and fragments thereof modulate an inflammatory response by interacting with an FPR member.

EXAMPLE 1

Cells and Reagents

The T20/DP178 and its analogs were synthesized and purified by the Department of Biochemistry, Colorado State University, Fort Collins, Colo., according to the published sequences. (See Lawless et al., *Biochemistry* 35: 13697 (1996), herein expressly incorporated by reference).

```
T20/DP178:
YTSLIHSLIEESQNQQEKNEQELLELDKWASLWNWF    SEQ ID NO:197

T716:
   LIHSLIEESQNQQEKNEQELLELDKWASLWNWF    SEQ ID NO:198

T719:
      HSLIEESQNQQEKNEQELLELDKWASLWNWF    SEQ ID NO:199

T712:
        LIEESQNQQEKNEQELLELDKWASLWNWF    SEQ ID NO:200

T914:
              QNQQEKNEQELLELDKWASLWNWF    SEQ ID NO:201
```

Some embodiments were acylated. The purity was 90% or more and the amino acid composition was confirmed by mass-spectrometer. The endotoxin levels in dissolved peptides were undetectable. The chemotactic peptide formyl-methionyl-leucyl-phenylalanine (fMLP) was purchased from Sigma (St. Louis, Mo.). The human peripheral blood mononuclear cells were isolated from leukopacks through the courtesy of Transfusion Medicine Department, NIH Clinical Center, Bethesda, Md. Monocytes were further purified (purity >90%). Human neutrophils were purified from the same leukopacks with 3% dextran sedimentation with a purity of >98%. Rat basophilic leukemia cells stably transfected with an epitope tagged receptor for chemotactic formyl peptides, FPR, (Ali et al., *J. Biol. Chem.* 268: 24247 (1993)) were a kind gift of Drs. H. Ali, R. Richardson and R. Snyderman, Duke University, N.C. The cells were designated ETFR and were grown in DMEM, 10% FCS and 0.8 mg/ml geneticin (G418) to maintain selection pressure.

Chemotaxis Assays

Cell migration was assessed using a 48-well microchemotaxis chamber. Different concentrations of stimulants were placed in the wells of the lower compartment of the chamber (Neuro Probe, Cabin John, Mass.), the cell suspension was seeded in the wells of the upper compartment which was separated from the lower compartment by polycarbonate filters (Osmonics, Livermore, Calif.; 5 µm-pore size for monocytes and neutrophils, 10 µm pore-size for ETFR cells). The filter for ETFR cell migration were precoated with 50 µg/ml collagen type I (Sigma) to favor the attachment of the cells. After incubation at 37° C. (90 min for monocytes, 60 min for neutrophils and 300 min for ETFR cells), the filters were removed, stained and the cells migrating across the filters were counted by light microscopy after coding the samples. The experiments were performed at least 5 times with each cell type and the results are presented as the number of migrating cells per high power field or as chemotaxis indeces (CI) representing the fold increase in the number of migrating cells in response to stimuli, over the spontaneous cell migration (in response to control medium). The significance of the increase in cell migration was analysed with Student's t test and CI equals 2 and higher is statistically significant compared to medium control (at least p<0.05).

Calcium Mobilization

Calcium mobilization was assayed by incubating 107/ml of monocytes, neutrophils or ETFR cells in loading buffer containing 138 mM NaCl, 6 mM KCl, 1 mM CaCl2, 10 mM HEPES (pH 7.4), 5 mM glucose, 0.1% BSA with 5 µM Fura-2 (Sigma) at 37° C. for 30 min. The dye-loaded cells were washed and resuspended in fresh loading buffer. The cells were then transfered into quartz cuvettes (106 cells in 2 ml) which were placed in a luminescence spectrometer LS50 B (Perkin-Elmer Limited, Beaconsfield, England). Stimulants at different concentrations were added in a volume of 20 µl to the cuvettes at indicated time points. The ratio of fluorescence at 340 and 380 nm wavelength was calculated using the FL WinLab program (Perkin Elmer). The assays were performed at least 5 times and results from representative experiments are shown.

Phosphorylation of FPR and Measurement of MAP Kinase

Phosphorylation of FPR was examined by culturing [$^{32}$P]-orthophosphate (Amersham, Arlington Heights, Ill.) labeled ETFR cells (3×106) in 100-mm tissue culture dishes as described by Ali et al., *J. Biol. Chem.* 268: 24247 (1993). After stimulation with fMLP or T20/DP178, the cells were lysed and immunoprecipitation was performed by using an anti-HA antibody (12CA5) (Boehringer-Mannheim, Indianapolis, Ind.) and protein G sepharose (Pharmacia, Uppsala, Sweden). The immune complexes then were eluted with SDS-PAGE sample buffer (Novex, San Diego, Calif.) and subjected SDS-PAGE and autoradiography.

MAP kinase activation was measured as described previously. (Krump et al., *J. Biol. Chem.* 272: 937 (1997)). Briefly, following stimulation of human monocytes with T20/DP178, the cells were solubilized and a specific anti-p38 MAPK antibody (New England Biolabs, Beverly, Mass.) was added to the soluble fraction followed by addition of protein A-Sepharose (Pharmacia). The immune complexes bound to sepharose were eluted with SDS-PAGE loading buffer. After electrophoresis, the immune complexes were electrotransferred onto polyvinylidene difluoride (PVDF) membranes (Millipore Corporation, Bedford, Mass.) which were reacted with a mouse anti-phosphotyrosine antibody followed by a horseradish peroxidase-coupled anti-mouse antibody (New England Biolabs Inc., 1:5,000 dilution). The MAPK was finally detected by enhanced chemiluminescence (ECL; Amersham).

Binding Assays

Tritiated ($^3$H) fMLP was purchased from Dupont NEN (Boston, Mass.). A single concentration of $^3$H-fMLP (1 nCi) was added simultaneously with different concentrations of unlabeled agonists into 200 µl cell suspension (2×10$^6$ phagocytes or ETFR ells) in duplicate samples. The samples were incubated under constant rotation for 20 min at 37° C. After incubation, the samples were filtered onto Whatman GF/C fiber discs (Whatman International Ltd., Kent, UK) on a 12-well manifold followed by extensive washing with ice-cold PBS. The discs were air-dried at 65° C. and then were submerged in liquid scintillation cocktail and counted for β emision. The binding assays were performed 3 times. The rate of inhibition was calculated by the formula:

$$1 - \frac{\text{cpm obtained in the presence of unlabeled agonist}}{\text{cpm in the absence of unlabeled agonist}} \times 100\%$$

In the following example, we disclose the materials and methods used to perform the experiments which determined that T21/DP107 and fragments thereof modulate an inflammatory response by interacting with an FPR member.

EXAMPLE 2

Reagents and Cells

The T21/DP107 was synthesized and purified by the Department of Biochemistry, Colorado State University, Fort Collins, Co., according to the published sequence (aa 558–595 of gp41). (See Lawless et al., *Biochemistry* 35: 13697 (1996), herein expressly incorporated by reference).

T21/DP107: NNLLRAIEAQQHLLQLTVWGIKQLQARILAVERYLKDQ SEQ ID NO:202

Some embodiments were acylated. The purity was 90% or more and the amino acid composition was verified by mass-spectrometer. The endotoxin levels in dissolved peptide were undetectable. The synthetic formyl peptide fMLP was purchased from Sigma (St. Louis, Mo.). The human peripheral blood mononuclear cells were isolated from leukopacks through the courtesy of Transfusion Medicine Department, NIH Clinical Center, Bethesda, Md. Monocytes were further purified by ellutriation to yield >90% purity. Human polymorph neutrophils were purified from the same leukopacks by 3% dextran sedimentation with a purity of >98%. Rat basophilic leukemia cells stably transfected with Epitope tagged FPR (ETFR) were a kind gift of Drs. H. Ali and R. Snyderman, Duke University, N.C. The cells were designated ETFR and were grown in DMEM, 10% FCS and 0.8 mg/ml geneticin (G418) to maintain selection pressure. The FPR-like receptor 1 (FPRL1) cDNA was cloned and transfected into human embryonic kidney cells (HEK) 293 (designated FPRL1/293 cells) as reported previously. (Gao and M. Murphy, *J. Biol. Chem.* 268: 25395 (1993)). The cells were maintained in DMEM, 10% FCS and 2 mg/ml geneticin (G418).

Chemotaxis

Leukocytes, ETFR and FPRL1/293 cell migration was assessed using a 48-well microchemotaxis chamber technique as previously described. (Gong et al., *J. Biol. Chem.* 273: 4289 (1998); Gong et al., *J. Biol. Chem.* 272: 11682 (1997); and Kliger et al., *J. Biol. Chem.* 272: 13496 (1997)). Different concentrations of stimulants were placed in wells of the lower compartment of the chamber (Neuro Probe, Cabin John, Mass.), the cell suspension was seeded in wells of the upper compartment which was separated from the lower compartment by a polycarbonate filter (Osmonics, Livermore, Calif.; 5 μm-pore size for leukocytes, 10 μm pore-size for ETFR and FPRL1/293 cells). For CD3+ T lymphocytes, the filters were precoated with 20 μg/ml bovine fibronectin (Sigma). The filters for ETFR and FPRL1/293 cell migration were precoated with 50 μg/ml collagen type I (Collaborative Biomedical products, Bedford, Mass.) to favor the attachment of the cells. After incubation at 37° C. (90 min for monocytes, 60 min for neutrophils, 180 min for T cells and 300 min for ETFR or FPRL1/293 cells), the filters were removed, stained and the cells migrating across the filter were counted by light microscopy after coding the samples. The experiments were performed at least 5 times with each cell type and the results are presented as the chemotaxis indexes (CI) representing the fold increase in the number of migrating cells in response to stimuli, over the spontaneous cell migration (in response to control medium). The significance of the increase in cell migration was determined using Student's t test and CI≧2 was statistically significant compared to medium control (at least $p<0.05$).

Calcium Mobilization

Calcium mobilization was assayed by incubating 107/ml of monocytes, neutrophils, FPRL1 or ETFR transfectants in loading buffer containing 138 mM NaCl, 6 mM KCl, 1 mM $CaCl_2$, 10 mM HEPES (pH 7.4), 5 mM glucose, 0.1% BSA with 5 μM Fura-2 (Sigma) at 37° C. for 30 min. The dye-loaded cells were washed and resuspended in fresh loading buffer. The cells were then transferred into quartz cuvettes (106 cells in 2 ml) which were placed in a luminescence spectrometer LS50 B (Perkin-Elmer Limited, Beaconsfield, England). Stimulants at different concentrations were added in a volume of 20 μl to the cuvettes at indicated time points. The ratio of fluorescence at 340 and 380 nm wavelength was calculated using the FL WinLab program (Perkin Elmer).

Unless specified, all experiments were performed at least five times with similar results and the data shown were from representative experiments.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of screening for agonist and antagonists comprising:

providing a peptide agent having a sequencec corresponding to T20/DP178 of SEQ ID NO:197 or a carboxy truncation, amino truncation thereof having a sequence selected from the group consisting of SEQ ID NO:2–96;

providing a cell having thereon a formyl peptide receptor (FPR) menber that interacts with said peptide agent;

contacting said peptide agent with said cell under conditions that low said peptide agent to interact with said FPR member on said cell;

identifying the presence or absence of signal transduction generate in response to the interaction of said peptide agent with said FPR member; and charaterizing said peptide agent as being an antagonist if said signal transduction is identified as being absent or charaterizing said peptide agent as being an agonist if said signal traduction is identified as being present.

2. The method of claim 1, wherein said peptide agent is a carboxy truncation, amino truncation, or internal truncation of T20/DP178 having a sequence selected from the group consisting of SEQ ID NO:2–96.

3. The method of claim 1, wherein said peptide agent is the animo truncation of T20/DP178 that lacks 3, 5, 7, or 12 amino acids at the N-terminus having a sequence selected from the group consisting of SEQ ID NO: 55, 60, 62, and 64.

4. The method of claim 1, wherein s id peptide agent is T20/DP178 of SEQ ID NO:197.

5. The method of any claims 1, 2, 3, or 4 further comprising incorporating said agonist or antagonist into a composition.

* * * * *

UNITED STATES PATENT AND TRADEMARK OFFICE
CERTIFICATE OF CORRECTION

PATENT NO. : 6,830,893 B2  
APPLICATION NO. : 10/005305  
DATED : December 14, 2004  
INVENTOR(S) : Wang et al.

It is certified that error appears in the above-identified patent and that said Letters Patent is hereby corrected as shown below:

In Col. 121, Line 36, Claim 1, delete "agonist" and insert --agonists--, therefore.

In Col. 121, Line 36, Claim 1, delete "sequencec" and insert --sequence--.

In Col. 121, Line 40, Claim 1, after "amino truncation" insert --, or internal truncation--, therefore.

In Col. 121, Line 44, Claim 1, delete "menber" and insert --member--, therefore.

In Col. 121, Line 46 (approx.), Claim 1, delete "low" and insert --allow--, therefore.

In Col. 121, Line 50 (approx.), Claim 1, delete "generate" and insert --generated--, therefore.

In Col. 122, Line 35, Claim 1, delete "charaterizing" and insert --characterizing--, therefore.

In Col. 122, Line 36, Claim 1, delete "traduction" and insert --transduction--, therefore.

In Col. 122, Line 43, Claim 3, delete "animo" and insert --amino--, therefore.

In Col. 122, Line 46, Claim 4, delete "s id" and insert --said--, therefore.

In Col. 122, Line 49, Claim 5, after "of any" insert --of--.

Signed and Sealed this

Fifth Day of December, 2006

JON W. DUDAS  
*Director of the United States Patent and Trademark Office*